United States Patent
Kurup

(10) Patent No.: US 11,814,388 B1
(45) Date of Patent: Nov. 14, 2023

(54) SUBSTITUTED PYRROLO[2,3-D]PYRIMIDINES AND PYRAZOLO[3,4-D]PYRIMIDINES AS INHIBITORS FOR MULTI-RESISTANT CANCERS

(71) Applicant: FERRIS STATE UNIVERSITY, Big Rapids, MI (US)

(72) Inventor: Sonali Raghavan Kunjunni Kurup, Big Rapids, MI (US)

(73) Assignee: Ferris State University, Big Rapids, MI (US)

( * ) Notice: Subject to any disclaimer, the term of this patent is extended or adjusted under 35 U.S.C. 154(b) by 0 days.

(21) Appl. No.: 17/459,558

(22) Filed: Aug. 27, 2021

Related U.S. Application Data

(60) Provisional application No. 63/071,446, filed on Aug. 28, 2020.

(51) Int. Cl.
C07D 487/04 (2006.01)
(52) U.S. Cl.
CPC .................. C07D 487/04 (2013.01)
(58) Field of Classification Search
CPC .................................... C07D 487/04
USPC ................................. 544/262, 280
See application file for complete search history.

(56) References Cited

U.S. PATENT DOCUMENTS

| | | | |
|---|---|---|---|
| 6,180,636 B1 * | 1/2001 | Traxler | C07D 487/04 544/280 |
| 7,560,551 B2 | 7/2009 | Cee et al. | |
| 8,404,694 B2 | 3/2013 | White et al. | |
| 9,126,935 B2 | 9/2015 | Deak et al. | |
| 2004/0242600 A1 | 12/2004 | Bold et al. | |
| 2004/0248911 A1 | 12/2004 | Bold et al. | |
| 2006/0211678 A1 | 9/2006 | Ahmed et al. | |
| 2009/0111805 A1 | 4/2009 | Morris et al. | |
| 2010/0204197 A1 | 8/2010 | Diels et al. | |
| 2011/0160203 A1 | 6/2011 | Liu et al. | |
| 2015/0246923 A1 | 9/2015 | Wang et al. | |
| 2017/0121346 A1 | 5/2017 | Sprengeler et al. | |
| 2020/0165246 A1 | 5/2020 | Deng et al. | |

FOREIGN PATENT DOCUMENTS

| | | |
|---|---|---|
| CN | 109384782 A | 2/2019 |
| WO | 2013078254 A1 | 5/2013 |

OTHER PUBLICATIONS

Adel M, Serya Rat, Lasheen DS, Abouzid Kam. Identification of new pyrrolo[2,3-d]pyrimidines as potent VEGFR-2 tyrosine kinase inhibitors: Design, synthesis, biological evaluation and molecular modeling. Bioorg Chem. Dec. 2018;81:612-629.

Tim Fischer, Abdulkarim Najjar, Frank Totzke, Christoph Schachtele, Wolfgang Sippl, Christoph Ritter & Andreas Hilgeroth (2018) Discovery of novel dual inhibitors of receptor tyrosine kinases EGFR and PDGFR-β related to anticancer drug resistance, Journal of Enzyme Inhibition and Medicinal Chemistry, 33:1, 1-8.

Reiersølmoen AC, Han J, Sundby E, Hoff BH. Identification of fused pyrimidines as interleukin 17 secretion inhibitors. Eur J Med Chem. Jul. 15, 2018; 155:562-578.

Reiersølmoen AC, Aarhus TI, Eckelt S, Nørsett KG, Sundby E, Hoff BH. Potent and selective EGFR inhibitors based an 5-aryl-7H-pyrrolopyrimidin-4-amines. Bioorg Chem. Jul. 2019;88:102918.

Miyaura, Norio, Suzuki, Akira, "Palladium-Catalyzed Cross-Coupling Reactions of Organoboron Compounds", Chem. Rev. 1995, 95, 2457-2483.

Zhang, Chunming et al., "Palladium-Imidazol-2-ylidene Complexes as Catalysts for Facile and Efficient Suzuki Cross-Coupling Reactions of Aryl Chlorides with Arylboronic Acids", J. Org. Chem. 1999, 64, 3804-3805.

Zhao, Baoguang et al., "Modulation of kinase-inhibitor interactions by auxiliary protein binding: Crystallography studies an Aurora A interactions with VX-680 and with TPX2", Protein Science 2008, 17, 1791-1797.

(Continued)

*Primary Examiner* — Douglas M Willis
(74) *Attorney, Agent, or Firm* — WARNER NORCROSS + JUDD LLP

(57) ABSTRACT

Compounds are provided herein. In general, the compounds are substituted pyrrolo[2,3-d]pyrimidines. The compounds can be used as inhibitors for multi-resistant cancers. Also provided herein are methods of forming the compounds, methods for inhibiting aurora kinase A and/or aurora kinase B activity and epidermal growth factor activity, methods of treating, ameliorating, or preventing cancer, and uses of the compounds for inhibiting aurora kinase A and/or aurora kinase B activity and epidermal growth factor receptor kinase activity. The compounds are generally of the formulas as illustrated herein, including those of Formula (I) or a pharmaceutically acceptable salt thereof:

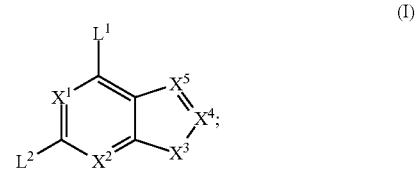

(I)

wherein: $X^1$ is N; $X^2$ is N; $X^3$ is —NH—; $X^4$ is N or $CR^2$; $X^5$ is CH or $CCH_3$; $L^1$ is —$NR^4$—$R^1$; $L^2$ is $NH_2$ or H; $R^1$ is:

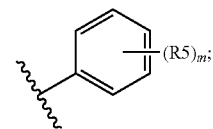

$R^2$ is a 5-membered heteroaryl; $R^4$ is H; R5 is as described herein; and m is 1, 2, 3, 4, or 5.

15 Claims, 18 Drawing Sheets

(56) References Cited

OTHER PUBLICATIONS

Yun, Cai-Hong et al., "The T790M mutation in EGFR kinase causes drug resistance by increasing the affinity for ATP", PNAS 2008, 105, 2070-2075.
Girdler, Fiona et al., "Molecular Basis of Drug Resistance in Aurora Kinases", Chemistry & Biology 2008, 15, 552-562.
Le Brazidec, Jean-Yves et al., "Structure-based design of 2,6,7-trisubstituted-7H-pyrrolo[2,3-d]pyrimidines as Aurora kinases inhibitors", Bioorganic & Medicinal Chemistry Letters 2012, 22, 4033-4037.
Radi, Marco et al., "Design, Synthesis, and Biological Evaluation of Pyrazolo[3,4-d]pyrimidines Active in Vivo on the Bcr-Abl T315I Mutant", Journal of Medicinal Chemistry 2013, 56, 5382-5394.
Gehringer, Matthias et al., "Novel Hinge-Binding Motifs for Janus Kinase 3 Inhibitors: A Comprehensive Structure-Activity Relationship Study on Tofacitinib Bioisosteres", ChemMedChem 2014, 9, 2516-2527.
Planken, Simon et al., "Discovery of N-((3R,4R)-4-Fluoro-1-(6-((3-methoxy-1-methyl-1H-pyrazol-4-yl)amino)-9-methyl-9H-purin-2-yl)pyrrolidine-3-acrylamide (PF-06747775) through Structure-Based Drug Design: A High Affinity Yreversible Inhibitor Targeting Oncogenic EGFR Mutants with Selectivity over Wild-Type Egfr", J. Med. Chern. 2017, 30, 3002-3019.
Kurup, Sonali et al., "Design, synthesis and biological activity of N4-phenylsubstituted-7H-pyrrolo[2,3-d]pyrimidin-4-amines as dual inhibitors of aurora kinase A and epidermal growth factor receptor kinase", Journal of Enzyme Inhibition and Medicinal Chemistry 2017, 33, 74-84.
Zhang, X., Zhou, Z., Kisliuk, R. L., Piraino, J., Cody, V., & Gangjee, A. (2011). Design, Synthesis, Biological Evaluation and X-ray Crystal Structure of Novel Classical 6,5,6-tricyclic Benzo[4,5]thieno[2,3-d]pyrimidines as Dual Thymidylate Synthase and Dihydrofolate Reductase Inhibitors. Bioorganic & Medicinal Chemistry, 19, 3585-3594.

\* cited by examiner a) Isopropanol, catalytic conc HCl, reflux, 10h; b) SOCl$_2$, reflux, 2h; c) 13, NEt$_3$, DMF, room temperature, 8h.; d) PyBOP, HOBt, DIEA, DMF, room temperature, 8h; e) CF$_3$COOH, CH$_2$Cl$_2$, 0 °C, 8h; f) isopropanol, catalytic conc HCl, reflux, 10h;

a) Pd/ligand, B$_2$Pin$_2$, EtOH, KOAc; b) aq LiOH; d) PyBOP, HOBt, DIEA, DMF, room temperature, 8h; e) CF$_3$COOH, CH$_2$Cl$_2$, 0 °C, 8h; f) isopropanol, catalytic conc HCl, reflux, 10h;

a) isopropanol, catalytic conc HCl, reflux, 10h; b) SOCl₂, reflux, 2h; c) 84, NEt₃, DMF, room temperature, 8h.; d) PyBOP, HOBt, DIEA, DMF, room temperature, 8h a) 99, isopropanol, catalytic conc HCl, reflux, 10h a) Ph₃Cl,NaH, DMF, r.t.12 h, N₂; b) R₄-B(OH)₂,Pd(PPh₃)₄,K₃PO₄, DMF, μwave, 3 h; c)4-aminobenzanilide, isopropanol, conc HCl, reflux 3 h; d) CF₃COOH,THF a) SEM-Cl,NaH, DMF, r.t.12 h, N₂; b) R₅-NH₂,Pd₂(dba)₃,Cs₂CO₃, Xantphos, 1,4-dioxane,N₂, μwave, 140 °C, 45 minutes; c)4-aminobenzanilide, , isopropanol, conc HCl, reflux 3 h; d) CF₃COOH, CH₂Cl₂ a) K₂CO₃, R-Br, DMSO, N₂, 12 h, 25 °C; b) Y-B(OH)₂, K₂CO₃, Pd(dppf)₂Cl₂, N₂,1,4-dioxane, 4h, 100 °C; c)Cs₂CO₃, t-amyl alcohol, 100 °C, N₂, 20h

SUBSTITUTED PYRROLO[2,3-D]PYRIMIDINES AND PYRAZOLO[3,4-D]PYRIMIDINES AS INHIBITORS FOR MULTI-RESISTANT CANCERS

CROSS-REFERENCE TO RELATED APPLICATIONS

This application claims priority to and all advantages of U.S. Provisional Pat. Appl. No. 63/071,446 filed on Aug. 28, 2020, the content of which is hereby incorporated by reference in its entirety.

TECHNICAL FIELD

The present disclosure generally relates to compounds useful as inhibitors for multi-resistant cancers. The present disclosure also relates to methods of forming the compounds, methods for inhibiting aurora kinase A and/or aurora kinase B activity and epidermal growth factor activity, methods of treating, ameliorating, or preventing cancer, and use of the compounds for inhibiting aurora kinase A and/or aurora kinase B activity and epidermal growth factor activity.

BACKGROUND

The EGFR (epidermal growth factor receptor) inhibitors were among the first kinase inhibitors that were developed as targeted agents. Although approved for use in NSCLC (non-small cell lung cancer), the efficacy of this class of compounds is short-lived due to multiple mutations in the ATP (adenosine triphosphate) pocket and redundant signaling cascades. The first-generation EGFR inhibitors, erlotinib and gefitinib have decreased therapeutic responses in tumors expressing wild-type EGFR (wt EGFR) as compared to EGFR with a sensitizing mutation which includes an exon-19 deletion (del19) or leucine to arginine (L858R) mutation in the catalytic site. Resistance to erlotinib and gefitinib has developed due to a threonine to methionine mutation (T790M) mutation in the ATP pocket. Newer generations of EGFR inhibitors continue to suffer from a short-lived effectiveness against mutant EGFR-positive tumors (mEGFR+), reducing their utility in clinical practice.

A cysteine to serine (C797S) mutation dramatically reduces therapeutic response to afatinib and osimertinib. A combination of erlotinib and osimertinib has been used in tumors expressing the L858R/T790M/C797S triple mutation; however, therapeutic outcomes have been inconsistent and poor.

The KRAS (Kirsten rat sarcoma virus) protein is a GTPase signaling protein in the RAS/MAP/ERK signaling cascade downstream of EGFR that interplays with multiple signaling pathways and plays a role in proliferation, differentiation and survival. In KRAS expressing NSCLC, it is wt EGFR and not sensitized L858R EGFR that colocalizes with KRAS. As a result, EGFR inhibitors have poorer outcomes in KRAS expressing tumors.

Additionally, KRAS mutations render the protein constitutively active. Persistent signaling mediated through mutant KRAS (mKRAS) leads to the activation of multiple downstream effector pathways irrespective of EGFR inhibition. Thus, EGFR inhibitors that work upstream of KRAS are rendered ineffective in mEGFR+ and mKRAS+NSCLC.

Newer therapeutic approaches that could address the resistance observed for EGFR inhibitors in mEGFR+ and mKRAS+NSCLC are needed.

Aurora kinase (AURK) inhibitors have been studied in combination with EGFR inhibitors for mEGFR+ and mKRAS+NSCLC. The mitosis-related aurora kinase A (AURKA) and aurora kinase B (AURKB) play a role in cell division and in pathways that drive tumorigenesis and metastasis. Erlotinib has demonstrated synergistic anticancer effects in combination with alisertib. It has also been shown that resistance to osimertinib was overcome if given in combination with alisertib in osimertinib-resistant NSCLC cells that were generated via osimertinib dose escalation. Osimertinib and alisertib were ineffective if given individually in the same cell lines. Mutant KRAS signaling in NSCLC was interrupted when erlotinib and ZM 447439 were utilized in combination.

Further, EGFR inhibitors used in combination with AURK inhibitors has been effective in mutant cancer cells derived from biopsy samples of lung cancer patients with disease progression on EGFR inhibitor therapy.

A Phase I study on the combination of erlotinib and alisertib was tolerated in NSCLC patients. A Phase II clinical trial is being planned to only include patients harboring KRAS mutations. A combination of erlotinib and barasertib also retards the development of the T790M EGFR mutation.

More recently, a Phase I/Ib study of alisertib in combination with osimertinib was initiated for metastatic EGFR-mutant positive lung cancer. Thus, the combination of AURK inhibitors with EGFR inhibitors has yielded promising results toward enhancing anticancer effects for EGFR inhibitors in NSCLC harboring mutant EGFR and mutant KRAS. Simultaneous inhibition of EGFR and AURK could provide an effective approach for circumventing resistance to EGFR inhibitors in NSCLC and improving therapeutic outcomes.

Dual-targeted EGFR/AURK inhibitors could provide advantages over a combination of single EGFR and single AURK inhibitors. Multi-targeted kinase inhibitors have shown several advantages over single kinase inhibitors by allowing for more predictable pharmacokinetics, reduced cost of therapy and improved patient compliance while maintaining the benefits of reduced incidence of resistance and enhanced anticancer effects.

Despite their promise, small molecule dual-targeted EGFR/AURK inhibitors are largely unexplored and the effectiveness of dual-targeted EGFR/AURK inhibitors against NSCLC is unknown.

Accordingly, it is desirable to provide compounds and methods for inhibiting aurora kinase A and/or aurora kinase B activity and epidermal growth factor activity. Furthermore, other desirable features and characteristics will become apparent from the subsequent summary and detailed description and the appended claims, taken in conjunction with the foregoing technical field and background.

SUMMARY OF THE INVENTION

A compound of Formula (I), Formula (II), or Formula (III), or pharmaceutically acceptable salts thereof, is provided herein. Formulas (I) to (III) are as follows:

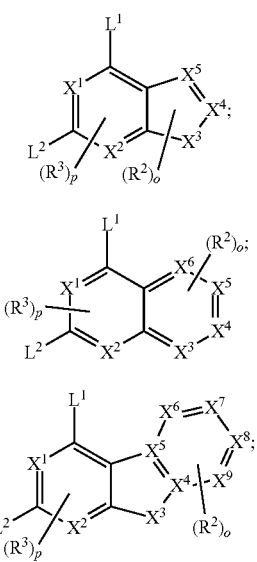

In Formulas (I) to (III) above: a) $L_1$ is —$CR^4_2$—$R^1$, —$NR^4$—$R^1$, —$OR^1$, or —$SR^1$, and $L_2$ is H; or b) $L_2$ is —$CR^4_2$—$R^1$, —$NR^4$—$R^1$, —$OR^1$, or —$SR^1$, and $L_1$ is H. Each of $X_1$ and $X_2$, independently, is $CR^3$ or N; $X_3$ is $CR^2_2$, $NR^2$, O, or S in Formula (I) or Formula (III), or is $CR^2$ or N in Formula (II). Each of $X_4$ and $X_5$, independently, is $CR^2$ or N in Formula (I) or Formula (II), or is C in Formula (III). Each of $X_6$, $X_7$, $X_8$, and $X_9$, independently, is $CR^2$ or N. Subscript "o" is 0 or 1, 2, 3, or 4. Subscript "p" is 0 or 1 or 2.

Each of $R^1$, $R^2$, $R^3$, and $R^4$, independently, is H, halo, alkylamino, arylamino, heteroalkylamino, heteroarylamino, alkylthio, arylthio, heteroalkylthio, heteroarylthio, heteroalkyloxy, heteroaryloxy, alkoxy, aryloxy, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $C(O)C_{1-6}$-alkyl, —NH-aryl-$C(O)NHC_{1-6}$-alkyl, —NH-heteroaryl-$C(O)NHC_{1-6}$-alkyl, —NH-alkyl-$C(O)NHC_{1-6}$-alkyl, —NH-aryl-$C(O)$ $NHC_{1-6}$-aryl, —NH-aryl-$C(O)NHC_{1-6}$-heteroaryl, —NH-aryl-$C(O)NHC_{1-6}$-heteroalkyl, —NH-arylNHC(O)$C_{1-6}$-alkyl, —NH-alkyl, —NH-aryl, —NH-heteroaryl, —NH-haloaryl, —NH-haloheteroaryl, —NH-aryl-$S(O)C_{1-6}$-alkyl, —NH-aryl-$S(O)_2NHC_{1-6}$-alkyl, —NH-alkyl-$S(O)_2NHC_{1-6}$-alkyl, —NH-heteroaryl-$S(O)_2NHC_{1-6}$-alkyl, —NH-heteroalkyl-$S(O)_2NHC_{1-6}$-alkyl, —NH-aryl-$S(O)_2NHC_{1-6}$-aryl, —NH-alkyl-$S(O)_2NHC_{1-6}$-aryl, —NH-heteroaryl-S $(O)_2NHC_{1-6}$-aryl, —NH-heteroalkyl-$S(O)_2NHC_{1-6}$-aryl, —NH-aryl-$S(O)_2NHC_{1-6}$-heteroaryl, —NH-alkyl-$S(O)_2$ $NHC_{1-6}$-heteroaryl, —NH-heteroaryl-$S(O)_2NHC_{1-6}$-heteroaryl, —NH-heteroalkyl-$S(O)_2NHC_{1-6}$-heteroaryl, —NH-aryl-NHC(O)—$C_{1-6}$-alkyl, —NH-heteroarylNHC(O)— $C_{1-6}$-alkyl, —NH-alkyl-NHC(O)—$C_{1-6}$-alkyl, —NH-aryl-NHC(O)—$C_{1-6}$-aryl, —NH-aryl-NHC(O)—$C_{1-6}$-heteroaryl, —NH-aryl-NHC(O)—$C_{1-6}$-heteroalkyl, —NH-arylNHC(O)—$C_{1-6}$-alkyl, —NH-alkyl, —NH-aryl, —NH-haloaryl, —NH-haloheteroaryl, —NH-aryl-$S(O)C_{1-6}$-alkyl; —NH-aryl-$NHS(O)_2C_{1-6}$-alkyl, —NH-alkyl-$NHS(O)_2C_{1-6}$-alkyl, —NH-heteroaryl-$NHS(O)_2C_{1-6}$-alkyl, —NH-heteroalkyl-$NHS(O)_2C_{1-6}$-alkyl, —NH-aryl-$NHS(O)_2C_{1-6}$-aryl, —NH-alkyl-$NHS(O)_2C_{1-6}$-aryl, —NH-heteroaryl-$NHS(O)_2C_{1-6}$-aryl, —NH-heteroalkyl-$NHS(O)_2C_{1-6}$-aryl, —NH-aryl-$NHS(O)_2C_{1-6}$-heteroaryl, —NH-alkyl-$NHS(O)_2$ $C_{1-6}$-heteroaryl, —NH-heteroaryl-$NHS(O)_2C_{1-6}$-heteroaryl, —NH-heteroalkyl-$NHS(O)_2C_{1-6}$-heteroaryl, —$NHS(O)_2$ $C_{1-10}$-alkyl or a fully saturated or partially or fully unsaturated 3-8 membered monocyclic or 6-12 membered bicyclic ring system, the ring system formed of carbon atoms optionally including 1-3 heteroatoms if monocyclic or 1-6 heteroatoms if bicyclic, the heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of the ring system is optionally substituted independently with 1-5 substituents of halo, haloalkyl, haloalkoxyl, CN, $NO_2$, $NH_2$, OH, oxo, $C_{1-6}$-alkyl, $C_{1-6}$-alkoxyl, $C_{3-6}$-cycloalkyl, $C_{1-10}$-alkylamino-, $C_{1-10}$-dialkylamino-, benzyl or phenyl, or is a multi-ring moiety comprising at least one substituted or unsubstituted aromatic ring or at least one substituted or unsubstituted nonaromatic ring, or comprises at least one substituted or unsubstituted heteroaromatic ring.

A method for inhibiting aurora kinase A and/or aurora kinase B activity—and epidermal growth factor activity—is also provided herein. In addition, a method of treating, ameliorating, or preventing cancer is provided herein.

DEFINITIONS

Figure 1A:
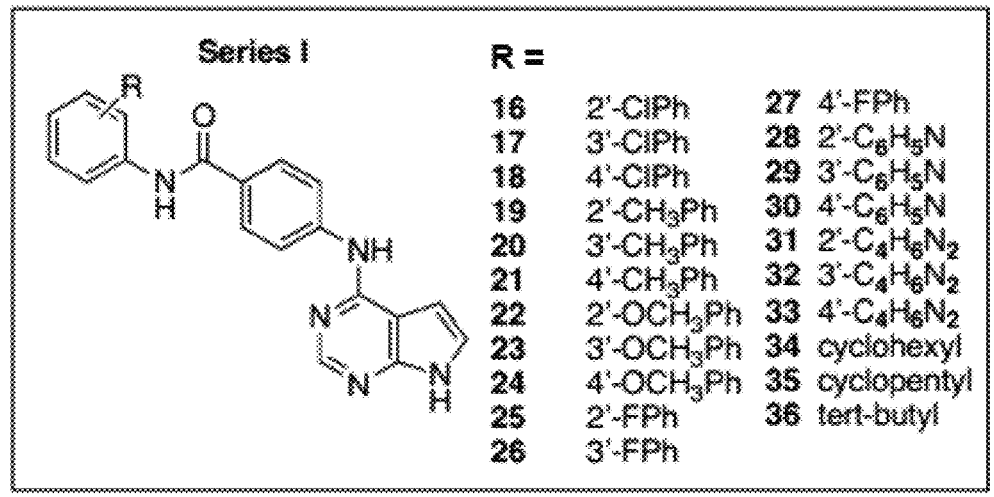
FIGS. 1A-1G are representations of chemical structures illustrating non-limiting embodiments of a compound.
Figure 1B:
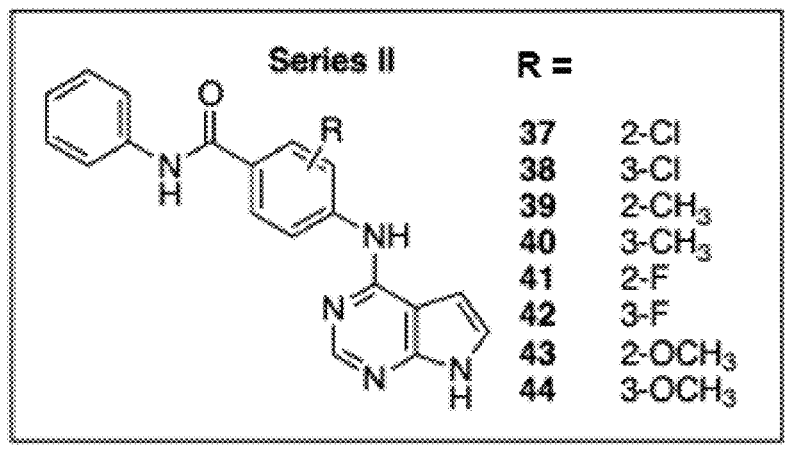
Figure 1C:
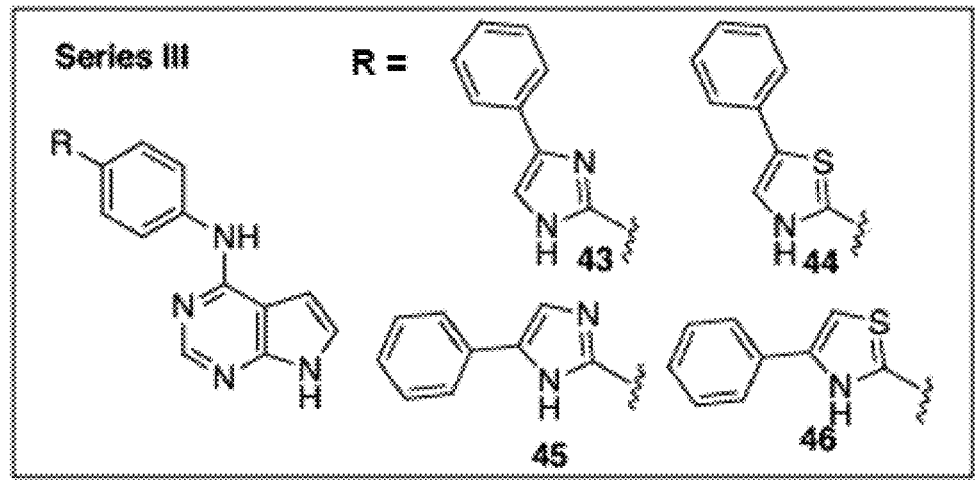
Figure 1D:
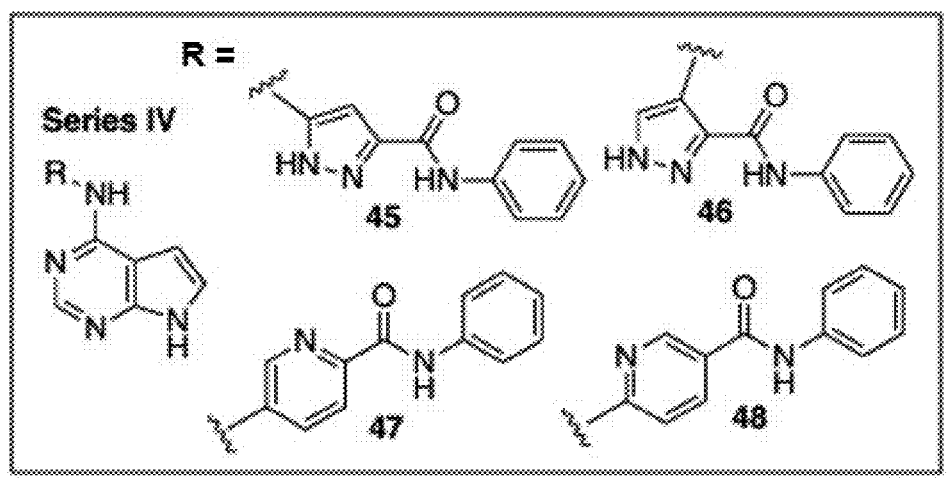
Figure 1E:
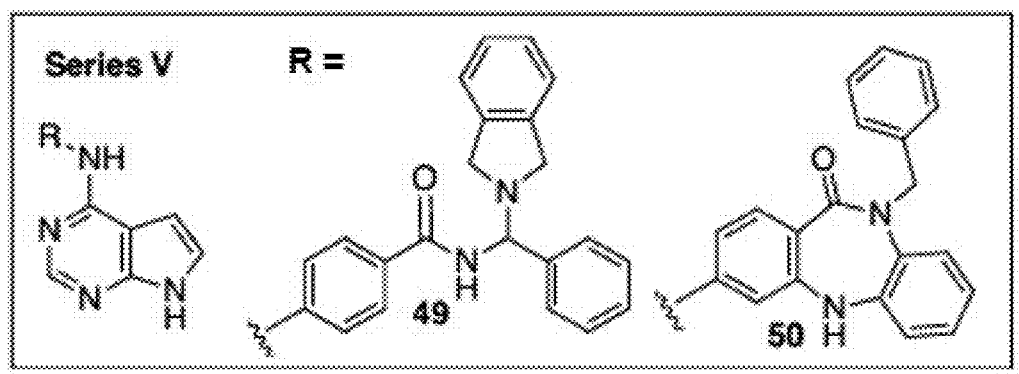
Figure 1F:
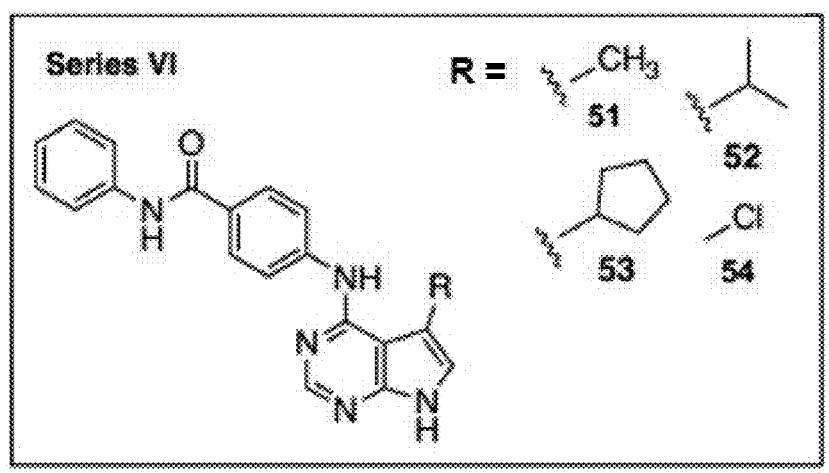
Figure 1G:
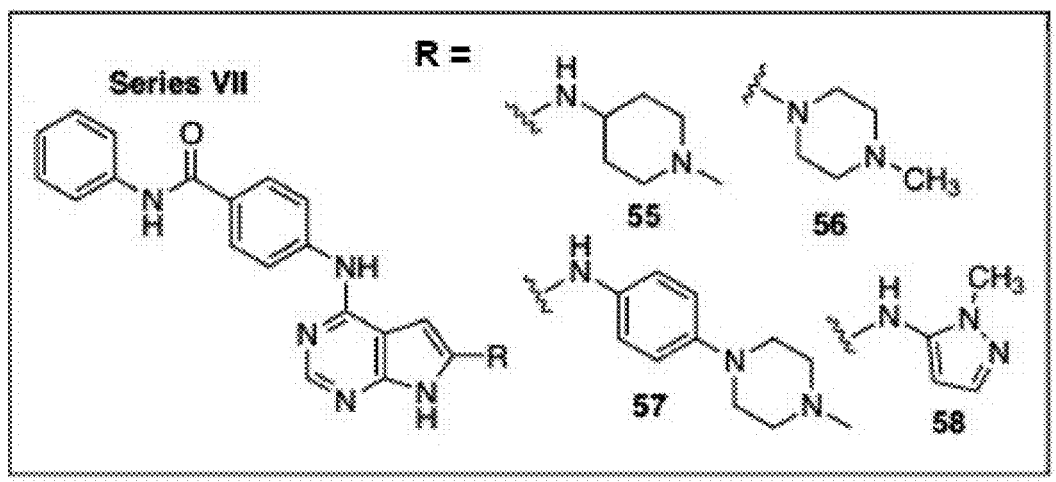
Figure 2A:
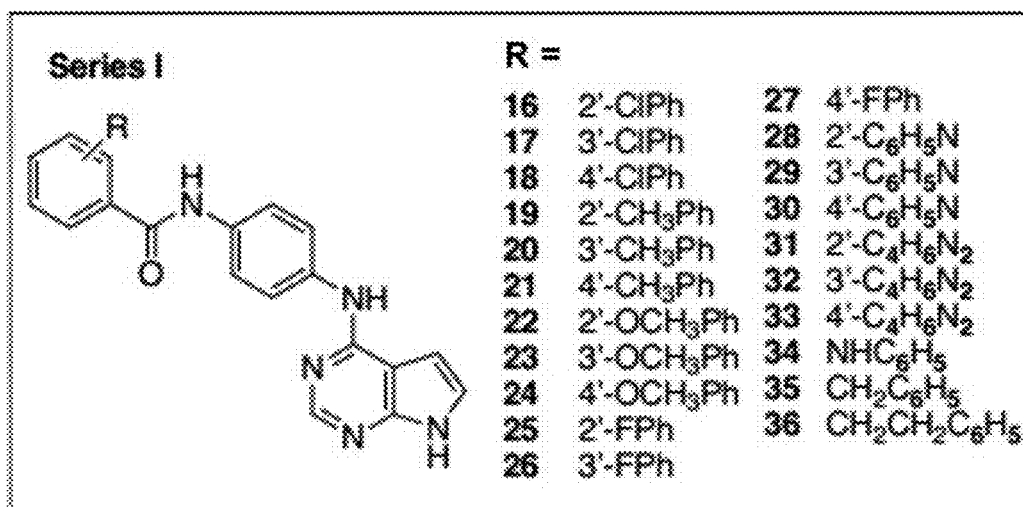
FIGS. 2A-2F are representations of chemical structures illustrating other non-limiting embodiments of the compound.
Figure 2B:
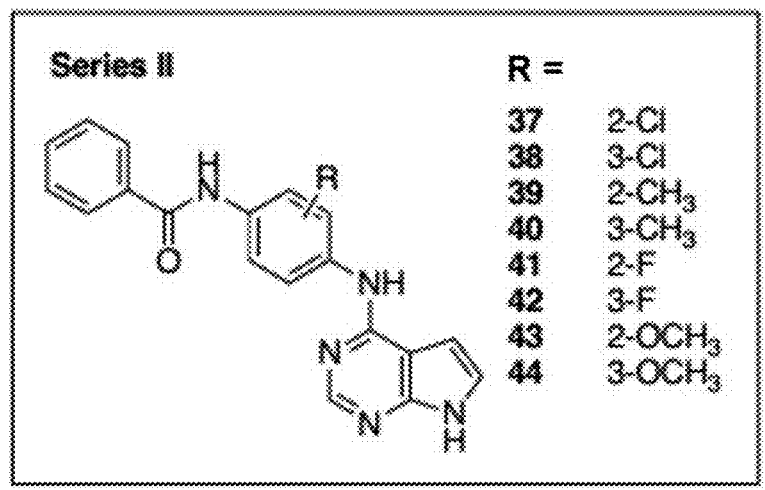
Figure 2C:
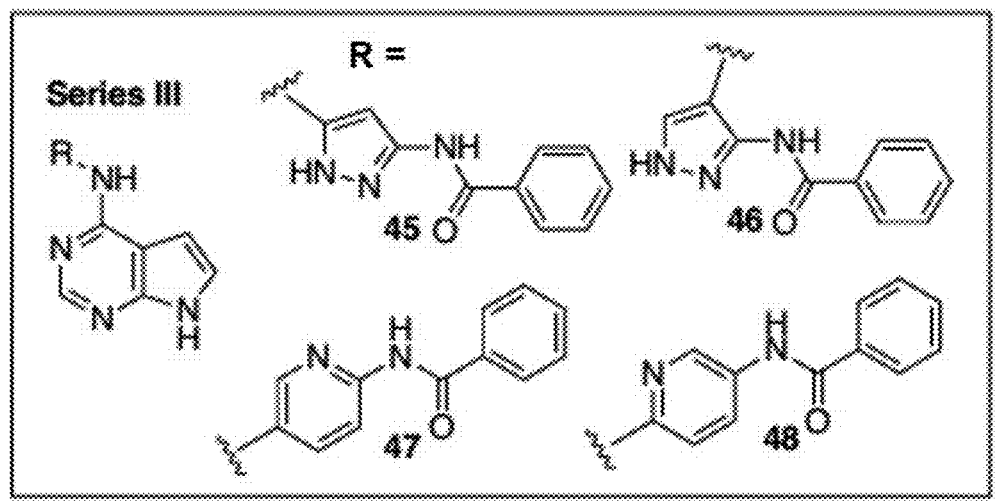
Figure 2D:
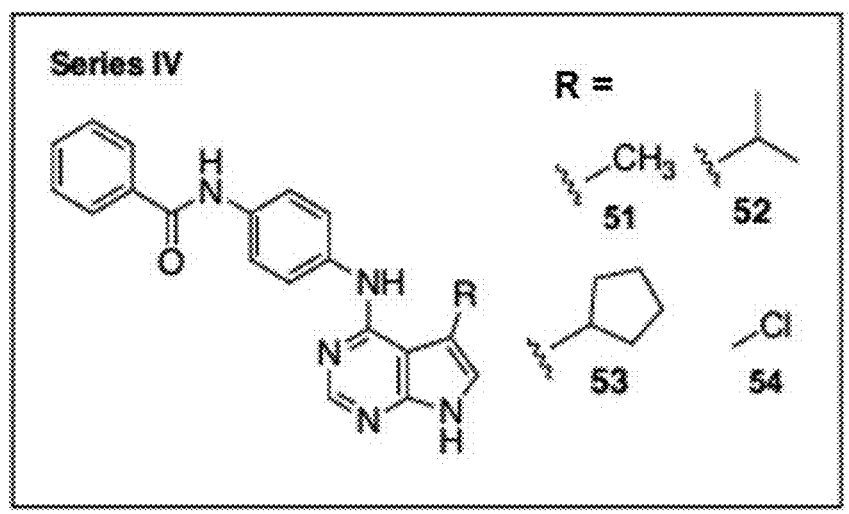
Figure 2E:
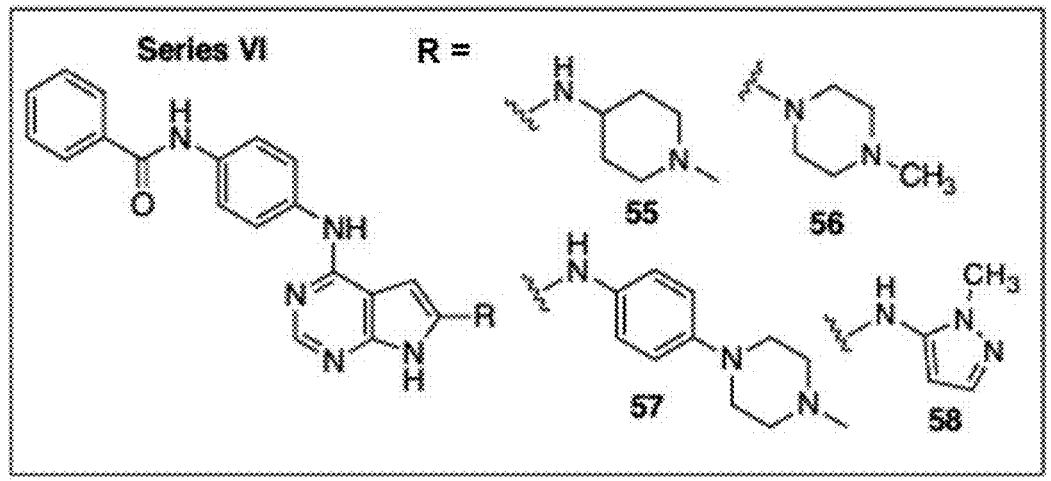
Figure 2F:
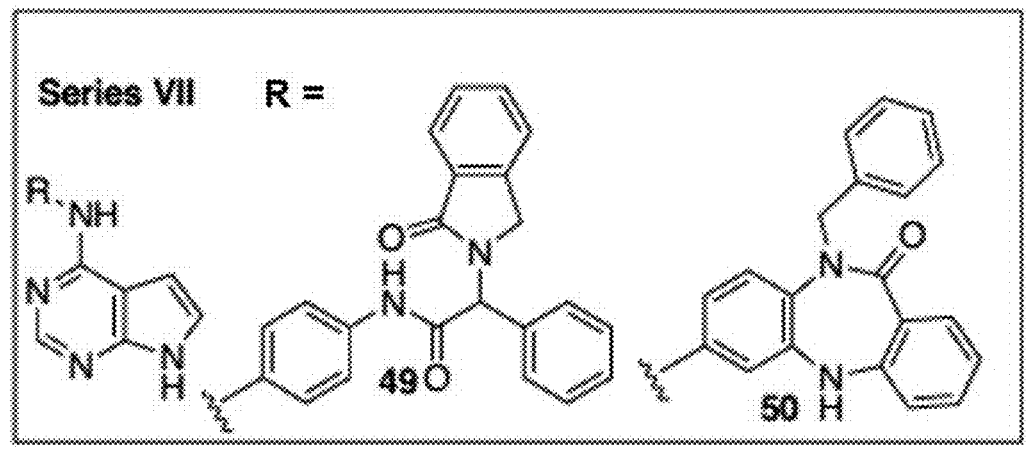
Figure 3A:
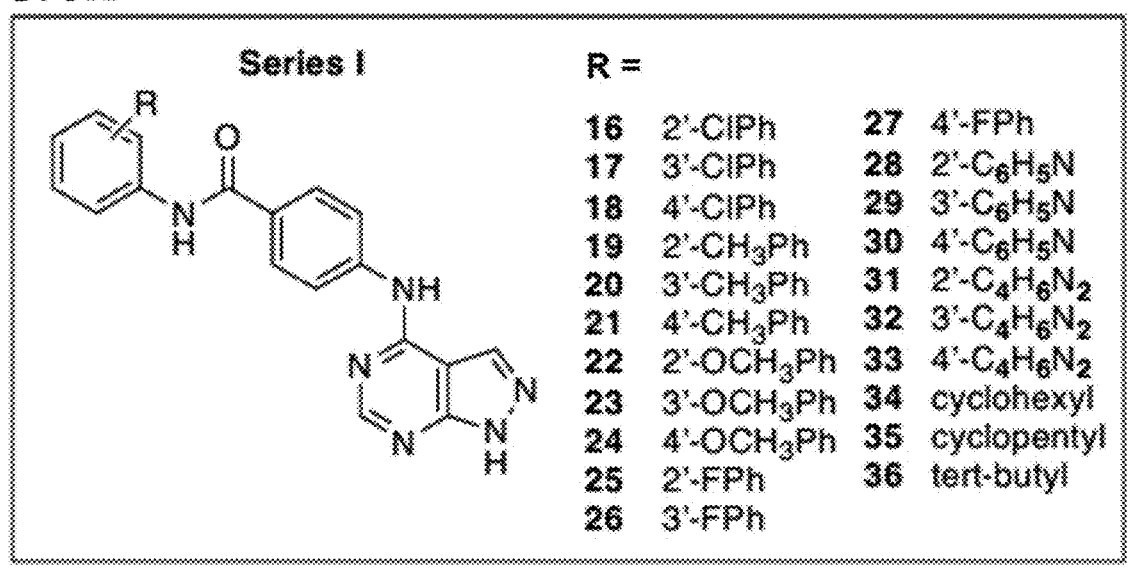
FIGS. 3A-3D are representations of chemical structures illustrating other non-limiting embodiments of the compound.
Figure 3B:
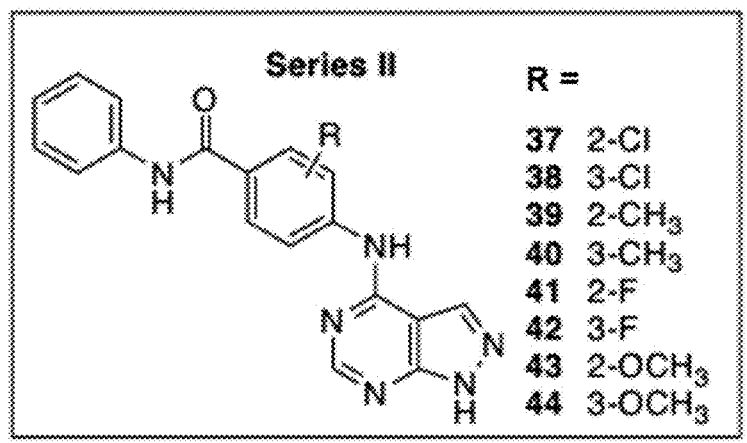
Figure 3C:
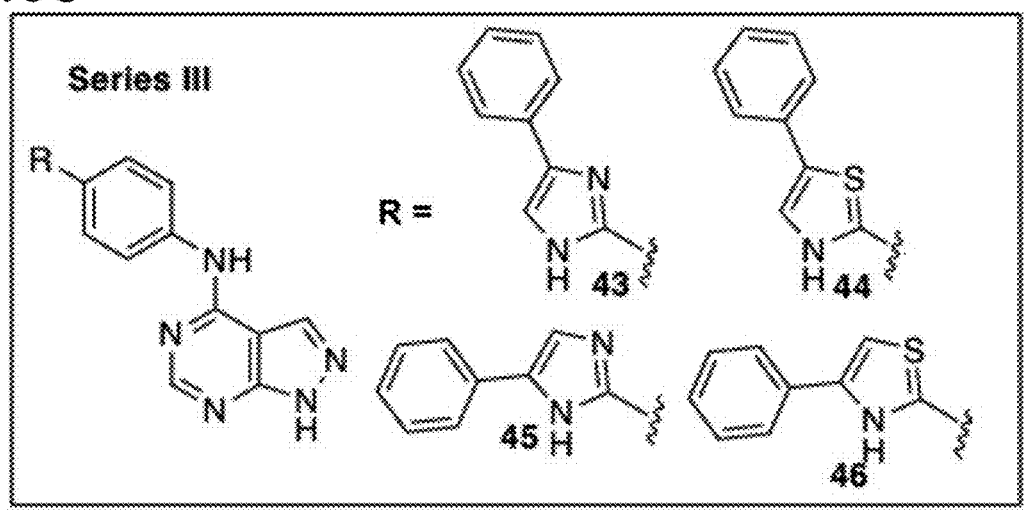
Figure 3D:
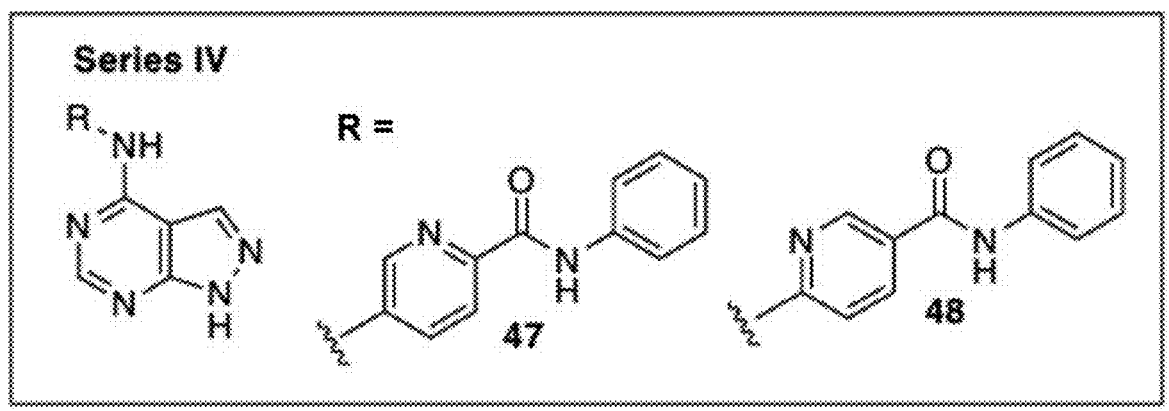
Figure 3E:
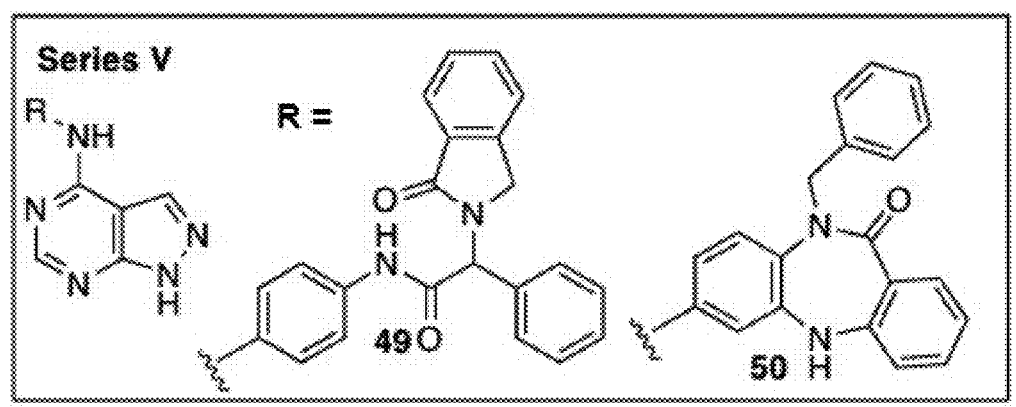
FIGS. 3E-3H are representations of chemical structures illustrating other non-limiting embodiments of the compound.
Figure 3F:
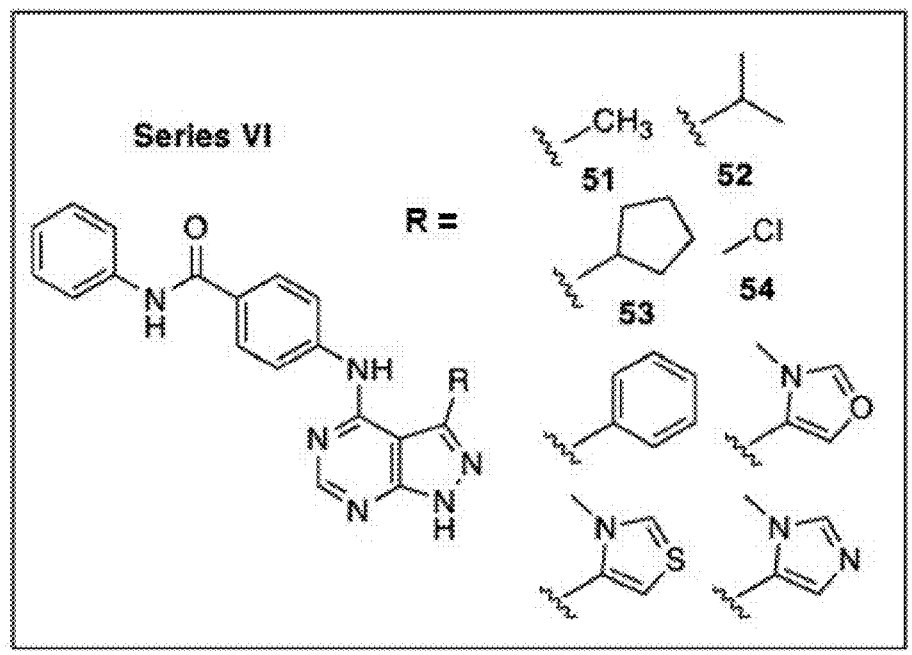
Figure 3G:
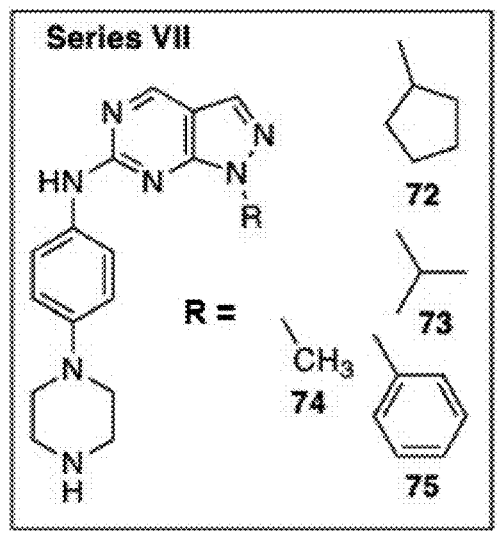
Figure 3H:
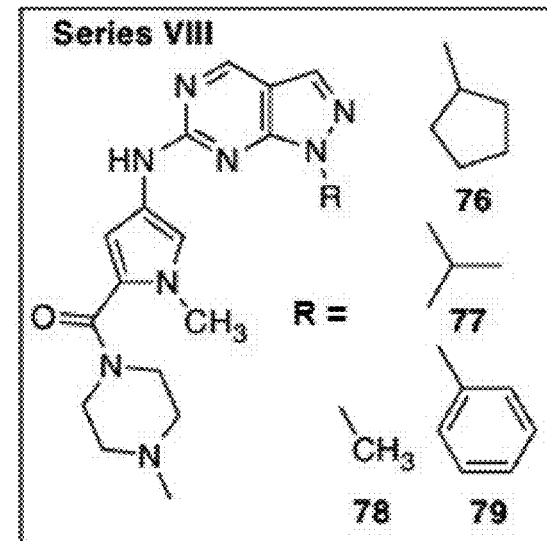
Figure 4A:
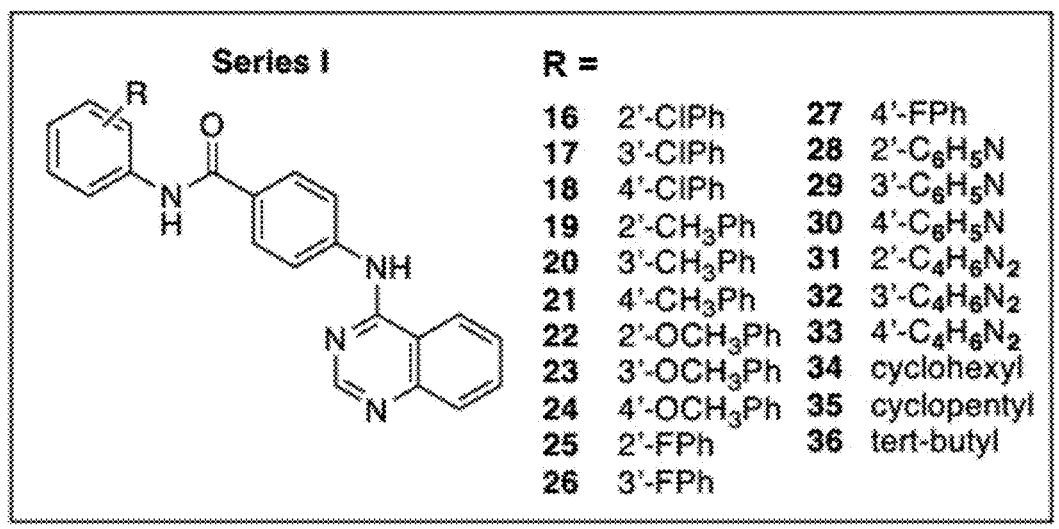
FIGS. 4A-4C are representations of chemical structures illustrating other non-limiting embodiments of the compound.
Figure 4B:
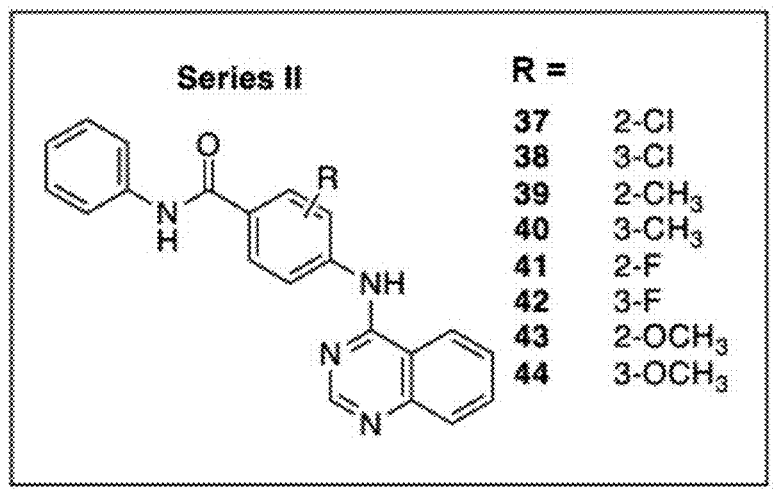
Figure 4C:
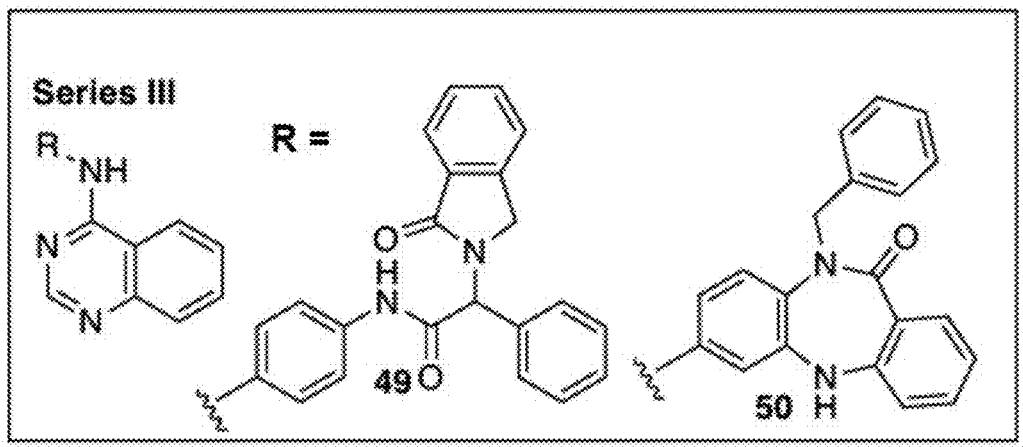
Figure 4D:
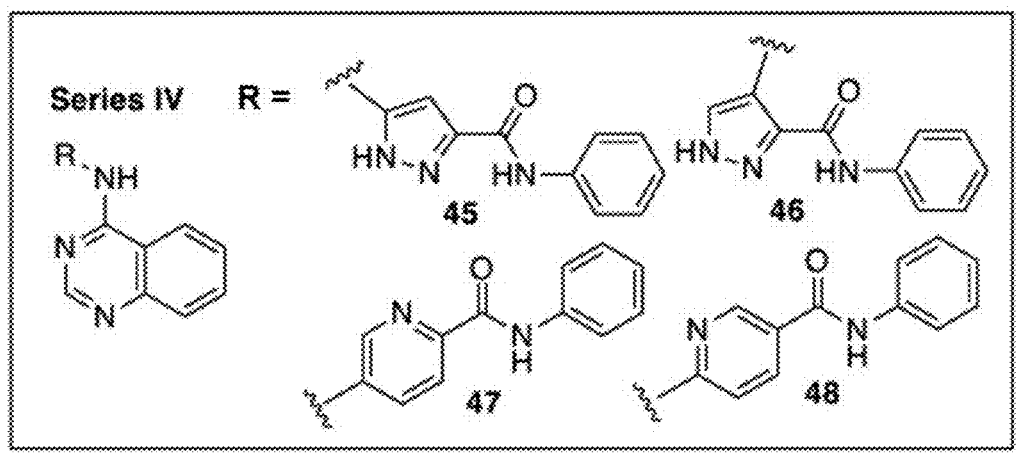
FIGS. 4D-4F are representations of chemical structures illustrating other non-limiting embodiments of the compound.
Figure 4E:
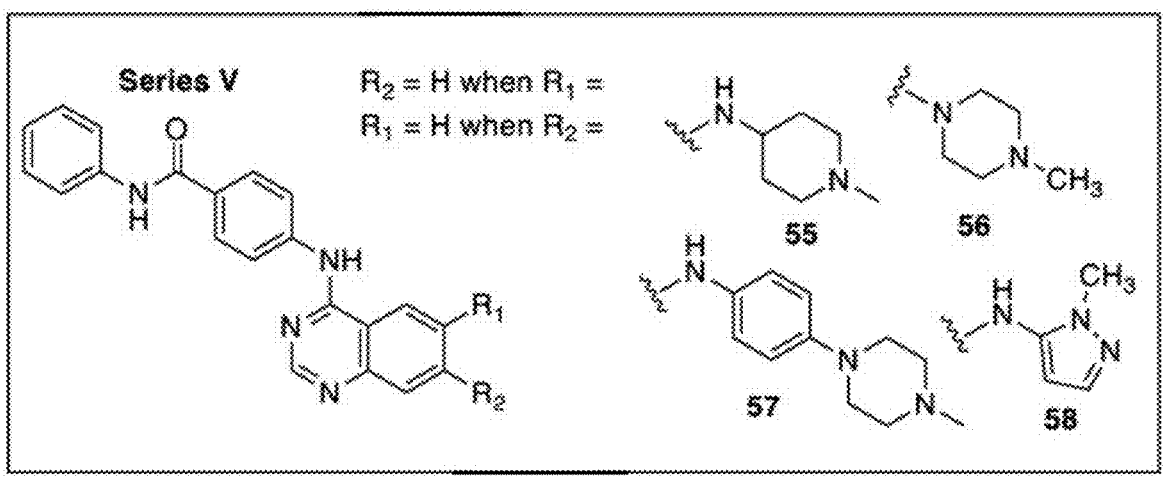
Figure 4F:
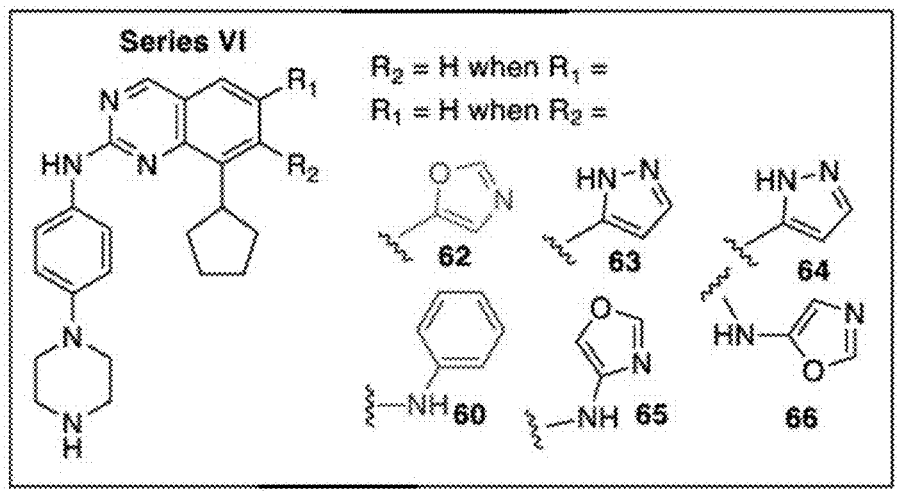
Figure 5A:
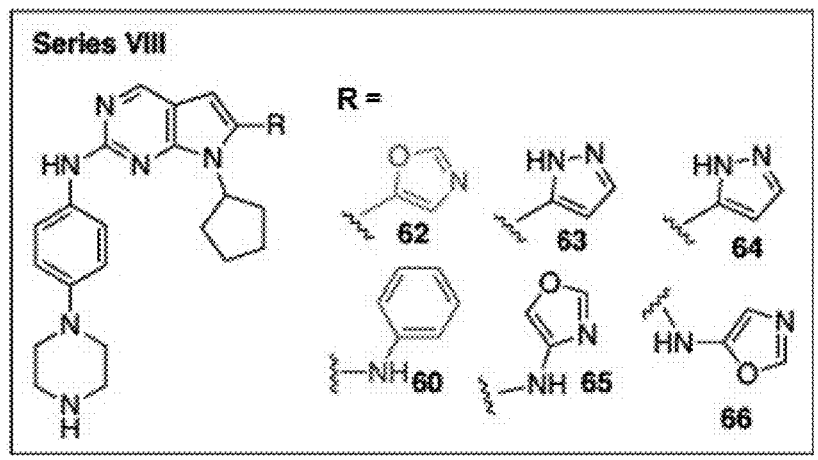
FIGS. 5A-5E are representations of chemical structures illustrating other non-limiting embodiments of the compound.
Figure 5B:
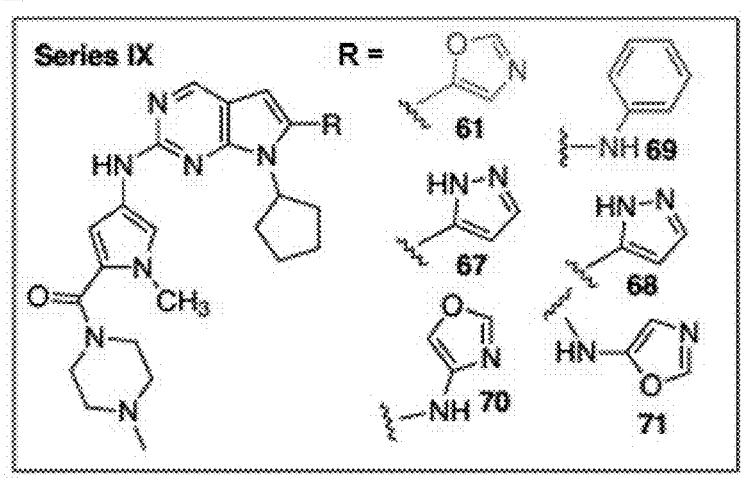
Figure 5C:
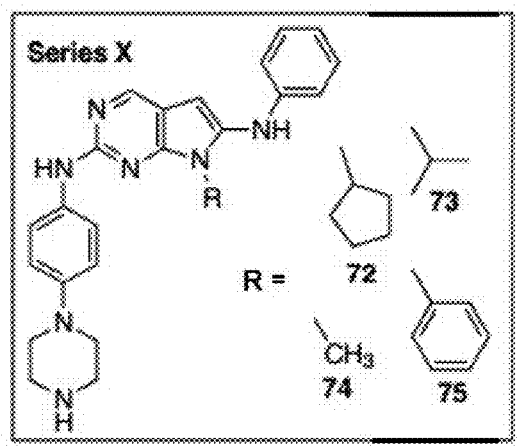
Figure 5D:
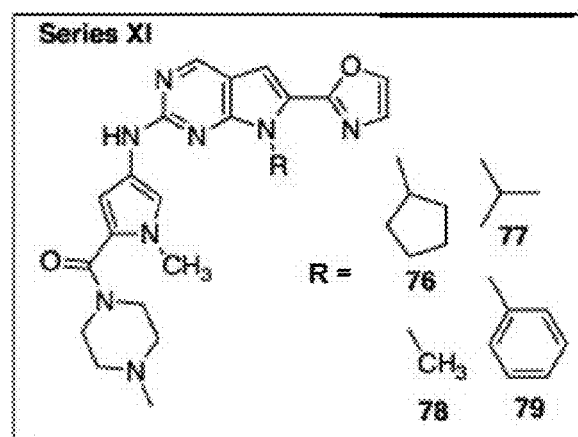
Figure 5E:
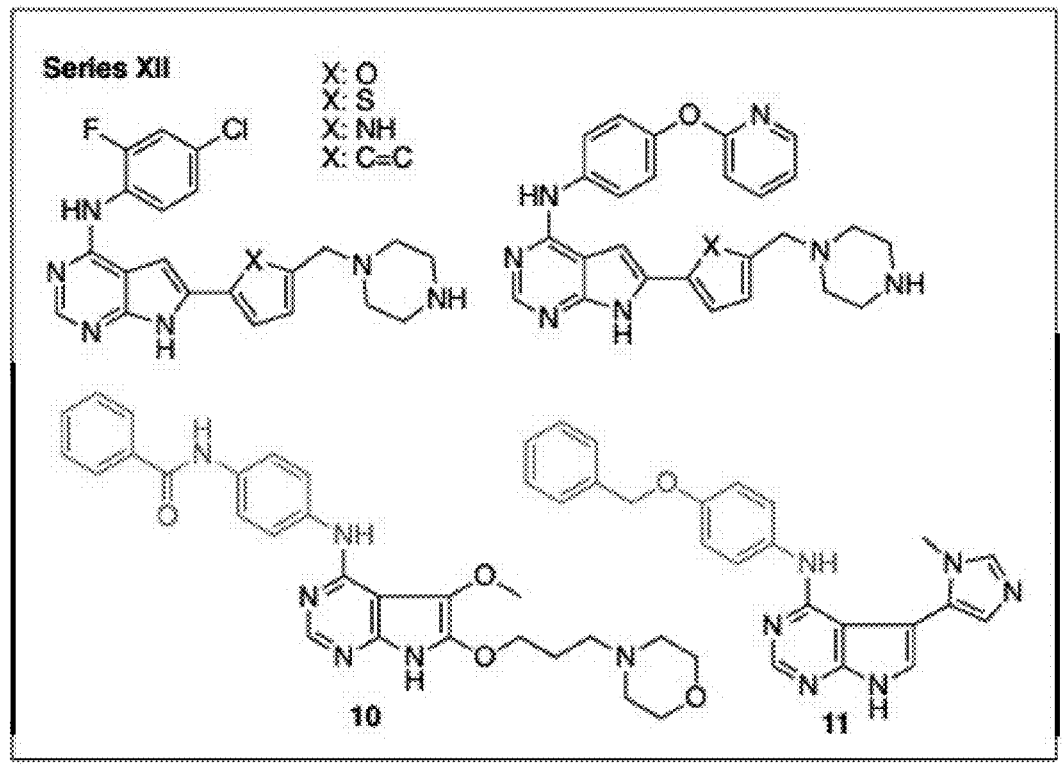

The following definitions should further assist in understanding the scope of the invention described herein.

The terms "cancer" and "cancerous" when used herein refer to or describe the physiological condition in mammals that is typically characterized by unregulated cell growth. Examples of cancer include, without limitation, carcinoma, lymphoma, sarcoma, blastoma and leukemia. More particular examples of such cancers include squamous cell carcinoma, lung cancer, non-small cell lung cancer, pancreatic cancer, cervical cancer, bladder cancer, hepatoma, breast cancer, colon cancer, and head and neck cancer. While the term "cancer" as used herein is not limited to any one specific form of the disease, it is believed that the compounds and related methods of the invention will be particularly effective for cancers which are found to be accompanied by unregulated levels of Aurora kinase(s) in the mammal.

The terms "treat", "treating" and "treatment" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The term "mammal" as used herein refers to any mammal classified as a mammal, including humans, cows, horses, dogs and cats. In one embodiment of the invention, the mammal is a human. The term "subject" can refer to such a mammal, e.g., a human.

A "pharmaceutically-acceptable derivative" denotes any salt (also referred to as "pharmaceutically-acceptable salt"), any prodrug such as a phosphate or an ester of a compound of this invention, or any other compound which upon administration to a patient is capable of providing (directly or indirectly) a compound of this invention, or a metabolite or residue thereof, characterized by the ability to inhibit Aurora kinase.

The phrase "therapeutically-effective" is intended to quantify the amount of each agent, which will achieve the goal of improvement in disorder severity and the frequency of incidence over treatment of each agent by itself, while avoiding adverse side effects typically associated with alternative therapies.

The terms "ring" and "ring system" refer to a one or more rings, fused where more than one ring, comprising the delineated number of atoms, said atoms being carbon or, where indicated, a heteroatom such as nitrogen, oxygen or sulfur. The ring itself, as well as any substituents thereon, may be attached at any atom that allows a stable compound to be formed. The term "nonaromatic" ring or ring system refers to the fact that at least one, but not necessarily all, rings in a bicyclic or tricyclic ring system is not fully unsaturated.

"Leaving groups" generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

Where the term "alkyl" is used, either alone or within other terms such as "haloalkyl" and "alkylamino", it embraces linear or branched radicals preferably having alpha to beta number of carbon atoms. For example a $C_1$-$C_{10}$ alkyl is an alkyl comprising 1 to 10 carbon atoms. Examples of such radicals include methyl, ethyl, n-propyl, isopropyl, n-butyl, isobutyl, sec-butyl, tert-butyl, pentyl, isoamyl, hexyl and the like. It is contemplated herein that alkyl radicals may be optionally substituted with various substituents, where indicated.

The term "alkenyl", alone or in combination, embraces linear or branched radicals having at least one carbon-carbon double bond and having two or more carbon atoms. Examples of alkenyl radicals include, without limitation, ethenyl, propenyl, allyl, propenyl, butenyl and 4-methylbutenyl. The term "alkenyl" embrace radicals having "cis" and "trans" orientations, or alternatively, "E" and "Z" orientations, as appreciated by those of ordinary skill in the art. It is contemplated herein that alkenyl radicals may be optionally substituted with various substituents, where indicated.

The term "alkynyl", alone or in combination, denotes linear or branched radicals having at least one carbon-carbon triple bond and having two or more carbon atoms. Examples of alkynyl radicals include, without limitation, ethynyl, propynyl (propargyl), butynyl, and the like. It is contemplated herein that alkynyl radicals may be optionally substituted with various substituents, where indicated.

The term "halo", alone or in combination, means halogens such as fluorine (F), chlorine (Cl), bromine (Br) or iodine (I) atoms.

The term "haloalkyl", alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "alkoxy", alone or in combination, embraces linear or branched oxy-containing radicals each having alkyl portions of alpha to beta number of carbon atoms. For example, a $C_{1-10}$alkoxy radical indicates an alkoxide having one to ten carbon atoms, arranged in a linear or branched fashion, attached to an oxygen atom. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals. Examples of such radicals include fluoromethoxy, chloromethoxy, trifluoromethoxy, trifluoroethoxy, fluoroethoxy and fluoropropoxy.

The term "a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S" is intended to encompass those mono- or multicyclic rings wherein the moiety is chemically stable and may be isolated in nature. Thus, rings wherein —O—O— or —S—S— or —N—O—S— type linkages are not stable, as appreciated by persons of ordinary skill in the art, and not intended to be within the scope of the invention.

The term "partially or fully saturated" as used herein, refers to a moiety, linear, branched or cyclic in nature, having no atom-atom double or triple bonds (fully saturated) or having one or more atom-atom double or triple bonds which are arranged such that where the structural moiety is cyclic, the cycle is not fully unsaturated (non-aromatic), as appreciated by those skilled in the art.

The term "fully unsaturated" as used herein, refers to a moiety having double or triple bonds, arranged in a manner such that the structure is aromatic in nature, as appreciated by those skilled in the art.

The term "aryl", alone or in combination, means a carbocyclic aromatic moiety containing one, two or even three rings wherein such rings may be attached together in a fused manner. Thus the term "aryl" embraces aromatic radicals such as phenyl, naphthyl, indenyl, tetrahydronaphthyl, anthracenyl, and indanyl. Said "aryl" group may have 1 or more substituents such as lower alkyl, hydroxyl, halo, haloalkyl, nitro, cyano, alkoxy and lower alkylamino, and the like. Phenyl substituted with —O—CH$_2$— forms an aryl benzodioxolyl substituent. Aryl as used herein, implies a fully unsaturated ring.

The term "heterocycles" or "heterocyclic radicals", alone or in combination, embraces saturated, partially saturated and partially unsaturated heteroatom-containing ring radicals, where the heteroatoms may be selected from nitrogen, sulfur and oxygen. This term does not include rings containing —O—O—, —O—S— or —S—S— portions. Said "heterocycle" may have 1 or more substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms (e.g. pyrrolidinyl, imidazolidinyl, piperidinyl, pyrrolinyl, piperazinyl); saturated 3 to 6-membered heteromonocyclic group containing 1 to 2 oxygen atoms and 1 to 3 nitrogen atoms (e.g. morpholinyl); saturated 3 to 6-membered heteromonocyclic group containing 1 to 2 sulfur atoms and 1 to 3 nitrogen atoms (e.g., thiazolidinyl). Examples of partially saturated (or partially unsaturated) heterocyclyl radicals include dihydrothienyl, dihydropyranyl, dihydrofuryl and dihydrothiazolyl.

The term "heteroaryl" radicals, alone or in combination, embraces fully unsaturated heteroatom-containing ring radicals, where the heteroatoms may be selected from nitrogen, sulfur and oxygen. Examples of heteroaryl radicals include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl (e.g., 4H-1,2,4-triazolyl, 1H-1,2,3-triazolyl, 2H-1,2,3-triazolyl); unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl); unsaturated 5 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl).

The terms "heterocycle" and "heteroaryl" also embraces radicals which are fused/condensed with aryl radicals: unsaturated condensed heterocyclic or heteroaryl groups containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl); unsaturated condensed heterocyclic group containing 1 to 2 oxygen atoms and 1 to 3 nitrogen atoms (e.g. benzoxazolyl, benzoxadiazolyl); unsaturated condensed heterocyclic group containing 1 to 2 sulfur atoms and 1 to 3 nitrogen atoms (e.g., benzothiazolyl, benzothiadiazolyl); and saturated, partially unsaturated and unsaturated condensed heterocyclic group containing 1 to 2 oxygen or sulfur atoms (e.g. benzofuryl, benzothienyl, 2,3-dihydro-benzo[1,4]dioxinyl and dihydrobenzofuryl). Examples of heterocyclic radicals include five to ten membered fused or unfused radicals. Further examples of heteroaryl radicals include quinolyl, isoquinolyl, imidazolyl, pyridyl, thienyl, thiazolyl, oxazolyl, furyl, and pyrazinyl. Other examples of heteroaryl radicals are 5- or 6-membered heteroaryl, containing one or two heteroatoms selected from sulfur, nitrogen and oxygen, such as thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl radicals.

Examples of non-nitrogen containing heteroaryl include, without limitation, pyranyl, 2-furyl, 3-furyl, 2-thienyl, 3-thienyl, benzofuryl, benzothienyl, and the like.

Examples of partially and fully saturated heterocyclyl include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "sulfonyl", whether used alone or linked to other terms such as alkylsulfonyl, denotes respectively divalent radicals —SO$_2$—.

The term "carbonyl", whether used alone or with other terms, such as "aminocarbonyl", denotes —(C=O)—.

The term "alkylthio" or "thioalkyl" embraces radicals containing a linear or branched alkyl radical, of one to ten carbon atoms, attached to a divalent sulfur atom. An example of "alkylthio" is methylthio, (CH$_3$S—).

The term "aminoalkyl" and "diaminoalkyl" embraces "N-alkylamino" and "N,N-dialkylamino", respectively, where amino groups are independently substituted with one alkyl radical and with two alkyl radicals, respectively.

Examples of alkylamino radicals include "lower alkylamino" radicals having one or two alkyl radicals of one to six carbon atoms, attached to a nitrogen atom. Suitable alkylamino radicals may be mono or dialkylamino such as N-methylamino, N-ethylamino, N,N-dimethylamino, N,N-diethylamino and the like.

The term "$C_{1-10}$alkyl-amino-" denotes amino groups, which have been substituted with one or two alkyl radicals, such as N-methylamino. The alkylamino radicals may be further substituted on the alkyl portion of the radical.

The term "aryl-alkyl-amino-" or "aralkylamino" denotes amino groups, which have been substituted with one or two aryl-substituted-alkyl radicals, such as benzyl-amino. The aralkyl-amino radicals may be further substituted on the aryl or alkyl portion of the radical.

The term "heterocyclyl-alkyl-amino-" denotes amino groups, which have been substituted with one or two heterocyclyl-substituted-alkyl radicals, such as piperidylmethyl-amino. The heterocyclyl-alkyl-amino radicals may be further substituted on the heterocycle or alkyl portion of the radical.

The term "heteroaryl-alkyl-amino-" or "heteroaralkylamino" denotes amino groups, which have been substituted with one or two heteroaryl-substituted-alkyl radicals, such as pyrimidyl-amino. The heteroaralkyl-amino radicals may be further substituted on the heteroaryl or alkyl portion of the radical.

The term "arylamino" denotes amino groups, which have been substituted with one or two aryl radicals, such as N-phenylamino. The arylamino radicals may be further substituted on the aryl ring portion of the radical.

The term "heteroarylamino" denotes amino groups, which have been substituted with one or two heteroaryl radicals, such as N-thienylamino. The "heteroarylamino" radicals may be further substituted on the heteroaryl ring portion of the radical.

The term "cycloalkyl" includes saturated carbocyclic groups. Examples of cycloalkyl groups include $C_3$-$C_6$ rings, such as compounds including, cyclopentyl, cyclopropyl, and cyclohexyl.

The term "cycloalkenyl" includes carbocyclic groups having one or more carbon-carbon double bonds including "cycloalkyldienyl" compounds. Examples of cycloalkenyl groups include $C_3$-$C_6$ rings, such as compounds including, without limitation, cyclopentenyl, cyclopentadienyl, cyclohexenyl and cycloheptadienyl.

DETAILED DESCRIPTION

Except in the examples, or where otherwise expressly indicated, all numerical quantities in this description indicating amounts of material or conditions of reaction and/or use are to be understood as modified by the word "about" in describing the broadest scope of the disclosure. In various embodiments, the terms "about" and "approximately", when referring to a specified, measurable value (such as a parameter, an amount, a temporal duration, and the like), is meant to encompass the specified value and variations of and from the specified value, such as variations of +/−10% or less, alternatively +1-5% or less, alternatively +/−1% or less, alternatively +/−0.1% or less of and from the specified value, insofar as such variations are appropriate to perform in the disclosed embodiments. Thus the value to which the modifier "about" or "approximately" refers is itself also specifically disclosed.

Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It must also be noted that, as used in the specification and the appended claims, the singular form "a," "an," and "the" comprise plural referents unless the context clearly indicates otherwise. For example, reference to a component in the singular is intended to comprise a plurality of components.

As used herein, an "embodiment" means that a particular feature, structure or characteristic is included in at least one or more manifestations, examples, or implementations of this invention. Furthermore, the particular features, structures or characteristics may be combined in any suitable manner, as would be apparent to a person skilled in the art. Combinations of features of different embodiments are all meant to be within the scope of the invention, without the need for explicitly describing every possible permutation by example. Thus, any of the claimed embodiments can be used in any combination.

As used herein, the term "weight percent" (and thus the associated abbreviation "wt. %") typically refers to a percent by weight expressed in terms of a weight of dry matter. As such, it is to be appreciated that a wt. % can be calculated on a basis of a total weight of a composition, or calculated from a ratio between two or more components/parts of a mixture (e.g. a total weight of dry matter).

Throughout this disclosure, where publications are referenced, the disclosures of these publications in their entireties are hereby incorporated by reference into this disclosure to more fully describe the state of the art to which this disclosure pertains.

The following detailed description is merely exemplary in nature and is not intended to limit the invention or the application and uses of the invention. Furthermore, there is no intention to be bound by any theory presented in the preceding background or the following detailed description.

In certain embodiments, compounds useful for treating, ameliorating, or preventing disorders relating to at least one of aurora kinase A (AURKA), aurora kinase B (AURKB), and epidermal growth factor (EGFR) are provided herein. In these and other embodiments, a method for inhibiting AURK A and/or AURK B activity—and EGFR activity—is provided herein. Further, a method of treating, ameliorating, or preventing cancer is also provided herein. The compounds are as described above, e.g. are of Formulas (I) to (III).

In various embodiments, the compounds provided herein are useful for treating, ameliorating, or preventing disorders, such as cancers, that are EGFR positive. The disorders, such as cancers, may exhibit over expression of wild-type EGFR, activated L858R, or del19 EGFR. It is believed that the compounds described herein are effective for inhibiting both AURK B activity and EGFR activity. Non-limiting examples of disorders suitable for treatment with the compounds described herein include, but are not limited to, lung cancer, prostate cancer, breast cancer, colon cancer, rectum cancer, head cancer, neck cancer, esophagogastric cancer, liver cancer, glioblastoma, melanoma, leukemias, lymphomas, sarcomas, fibrolamellar carcinoma, cervical cancer, ovarian cancer, bladder cancer, kidney cancer, pancreatic cancer, or combinations thereof.

Compounds and Related Methods

The present disclosure provides a compound. The compound is as introduced above, e.g. as described with Formulas (I), (II), and (III). In certain embodiments, $L_1$ is —$CR^4_2$—$R^1$, —$NR^4$—$R^1$, —$OR^1$, or —$SR^1$, and $L_2$ is H. In further embodiments, $L_1$ is —$NR^4$—$R^1$ and $L_2$ is H. In other embodiments, $L_2$ is —$CR^4_2$—$R^1$, —$NR^4$—$R^1$, —$OR^1$, or —$SR^1$, and $L_1$ is H. In further embodiments, $L_2$ is —$NR^4$—$R^1$ and $L_2$ is H.

In these embodiments, $NR^4$ and $R^1$ are as introduced above. For example, $R^4$ can be H, and $R^1$ can be other groups (or moieties) as described above or as specifically illustrated below or in the drawings.

In various embodiments, each of $X_1$ and $X_2$ is N. In these or other embodiments, $X_3$ is $NR^2$ where $R^2$ is H. In these or yet other embodiments, each of $X_4$ and $X_5$ is $CR^2$ where $R^2$ is H.

In various embodiments, each of the methods as introduced above includes administering (e.g. to a subject) an effective amount of the compound of Formula (I) or a pharmaceutically acceptable salt thereof, an effective amount of the compound of Formula (II) or a pharmaceutically acceptable salt thereof, an effective amount of compound of Formula (III) or a pharmaceutically acceptable salt thereof, or combinations of the compounds and/or salts thereof. The compound(s) and/or salt(s) thereof can be administered via methodologies understood in the art. Some examples of the same are described further below. In certain embodiments, the compound(s) and/or salt(s) thereof are utilized in treatment methods as described in U.S. Pat. No. 7,560,551 B2, U.S. Pat. No. 8,404,694 B2, or U.S. Pat. No. 9,126,935 B2, the disclosures of which are incorporated by reference in their entirety.

In various embodiments, $R^1$ is, or comprises:

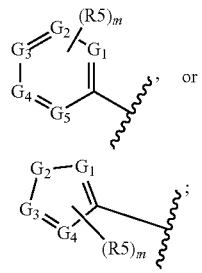

wherein each of G1, G2, G3, G4 and G5, independently, is CR5, N, NR5, O, or S.

One of skill in the art will understand that certain atoms or groups as described herein will be appropriate or not appropriate for a certain selection or location based on their valency. As just one example, oxygen (O) is suitable as G2 in the rightmost formula immediately above but is generally not suitable as G2 for the leftmost formula immediately above.

In various embodiments, R5 is H, halo, haloalkyl, haloalkoxyl, oxo, CN, OH, SH, $NO_2$, NH2, acetyl, C1-10-alkyl, C2-10-alkenyl, C2-10-alkynyl, C3-10-cycloalkyl, C4-10-cycloalkenyl, C1-10-alkylamino-, C1-10-dialkylamino-, C1-10-alkoxyl, C1-10-thioalkoxyl, $C(O)C_{1-6}$-alkyl, —$C(O)NHC_{1-6}$-alkyl, —$NHC(O)C_{1-6}$-alkyl, —$S(O)C_{1-6}$-alkyl, —$S(O)_2NHC_{1-6}$-alkyl, —$NHS(O)_2$C1-10-alkyl or a fully saturated or partially or fully unsaturated 3-8 membered monocyclic or 6-12 membered bicyclic ring system, the ring system formed of carbon atoms optionally including 1-3 heteroatoms if monocyclic or 1-6 heteroatoms if bicyclic, the heteroatoms selected from O, N, or S, wherein each of the C1-10-alkyl, C2-10-alkenyl, C2-10-alkynyl, C3-10-cycloalkyl, C4-10-cycloalkenyl, C1-10-alkylamino-, C1-10-dialkylamino-, C1-10-alkoxyl, C1-10-thioalkoxyl and ring of the ring system is optionally substituted independently with 1-5 substituents of halo, haloalkyl, haloalkoxyl, CN, NO2, NH2, OH, oxo, $C_{1-6}$-alkyl, $C_{1-6}$-alkoxyl, C3-6-cycloalkyl, C1-10-alkylamino-, C1-10-dialkylamino-, benzyl or phenyl, or is a multi-ring moiety comprising at least one substituted or unsubstituted aromatic ring and at least one substituted or unsubstituted nonaromatic ring, or comprises at least one substituted or unsubstituted heteroaromatic ring. Subscript "m" is 0 or 1, 2, 3, 4, or 5.

In some embodiments, R5 is, or comprises:

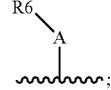

wherein A is a single bond, A is or comprises, or -A-R6 is or comprises, —$CH_2R6$, —CHR6R6, NHR6, O, S, alkenyl (—C=C—$R_6$), alkynyl-$R_6$ (—C≡C—$R_6$), —CONH—$R_6$; —NHCO—$R_6$; —$SO_2NH$—$R_6$; —$NHSO_2$—$R_6$; —NHCONH—$R_6$; O—$R_6$; or S—$R_6$.

In various embodiments, R6 is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $C(O)C_{1-6}$-alkyl, —$C(O)NHC_{1-6}$-alkyl, —$NHC(O)C_{1-6}$-alkyl, —$S(O)C_{1-6}$-alkyl, —$S(O)_2NHC_{1-6}$-alkyl, —$NHS(O)_2C_{1-10}$-alkyl or a fully saturated or partially or fully unsaturated 3-8 membered monocyclic or 6-12 membered bicyclic ring system, the ring system formed of carbon atoms optionally including 1-3 heteroatoms if monocyclic or 1-6 heteroatoms if bicyclic, the heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of the ring system is optionally substituted independently with 1-5 substituents of halo, haloalkyl, haloalkoxyl, CN, $NO_2$, $NH_2$, OH, oxo, $C_{1-6}$-alkyl, $C_{1-6}$-alkoxyl, $C_{3-6}$-cycloalkyl, $C_{1-10}$-alkylamino-, $C_{1-10}$-dialkylamino-, benzyl or phenyl, or is a multi-ring moiety comprising at least one substituted or unsubstituted aromatic ring and at least one substituted or unsubstituted nonaromatic ring, or comprises at least one substituted or unsubstituted heteroaromatic ring. Subscript "n" is 0 or 1, 2, 3, 4, or 5.

In various embodiments, A, or -A-R6, comprises:

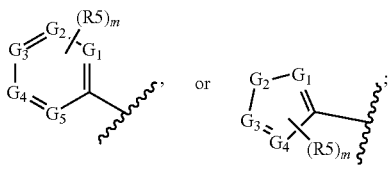

wherein, each of $G_1$, $G_2$, $G_3$, $G_4$ and $G_5$, independently, is CR5, N, NR5, O, or S;

In various embodiments, R5 is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $C(O)C_{1-6}$-alkyl, —C(O)NHC$_{1-6}$-alkyl, —NHC(O)C$_{1-6}$-alkyl, —S(O)C$_{1-6}$-alkyl, —S(O)$_2$NHC$_{1-6}$-alkyl, —NHS(O)$_2$C$_{1-10}$-alkyl or a fully saturated or partially or fully unsaturated 3-8 membered monocyclic or 6-12 membered bicyclic ring system, the ring system formed of carbon atoms optionally including 1-3 heteroatoms if monocyclic or 1-6 heteroatoms if bicyclic, the heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of the ring system is optionally substituted independently with 1-5 substituents of halo, haloalkyl, haloalkoxyl, CN, $NO_2$, $NH_2$, OH, oxo, $C_{1-6}$-alkyl, $C_{1-6}$-alkoxyl, $C_{3-6}$-cycloalkyl, $C_{1-10}$-alkylamino-, $C_{1-10}$-dialkylamino-, benzyl or phenyl, or is a multi-ring moiety comprising at least one substituted or unsubstituted aromatic ring and at least one substituted or unsubstituted nonaromatic ring, or comprises at least one substituted or unsubstituted heteroaromatic ring. Subscript "m" is 0 or 1, 2, 3, 4, or 5.

In various embodiments, R5 is, or comprises:

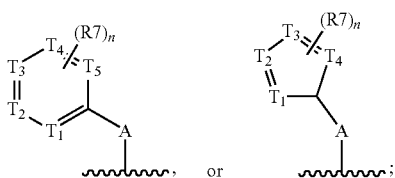

wherein, A is a single bond, or A comprises —CH$_2$R$_6$, —CHR$_6$—, NHR$_6$, O, S, alkenyl(—C═C—R$_6$), alkynyl-R$_6$, (———R$_6$), —CONH—R$_6$, —NHCO—R$_6$, —SO$_2$NH—R$_6$, —NHSO$_2$—R$_6$; —NHCONH—R$_6$, O—R$_6$, or S—R$_6$. Each of $T_1$, $T_2$, $T_3$, $T_4$ and $T_5$, independently, is CR6, N, NR6, O, or S.

In various embodiments, each of R6 and R7, independently, is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $C(O)C_{1-6}$-alkyl, —C(O)NHC$_{1-6}$-alkyl, —NHC(O)C$_{1-6}$-alkyl, —S(O)C$_{1-6}$-alkyl, —S(O)$_2$NHC$_{1-6}$-alkyl, —NHS(O)$_2$C$_{1-10}$-alkyl or a fully saturated or partially or fully unsaturated 3-8 membered monocyclic or 6-12 membered bicyclic ring system, the ring system formed of carbon atoms optionally including 1-3 heteroatoms if monocyclic or 1-6 heteroatoms if bicyclic, the heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of the ring system is optionally substituted independently with 1-5 substituents of halo, haloalkyl, haloalkoxyl, CN, $NO_2$, $NH_2$, OH, oxo, $C_{1-6}$-alkyl, $C_{1-6}$-alkoxyl, $C_{3-6}$-cycloalkyl, $C_{1-10}$-alkylamino-, $C_{1-10}$-dialkylamino-, benzyl or phenyl, or is a multi-ring moiety comprising at least one substituted or unsubstituted aromatic ring and at least one substituted or unsubstituted nonaromatic ring, or comprises at least one substituted or unsubstituted heteroaromatic ring. Subscript "n" is 0 or 1, 2, 3, 4, or 5.

In some embodiments, R5 is, or comprises:

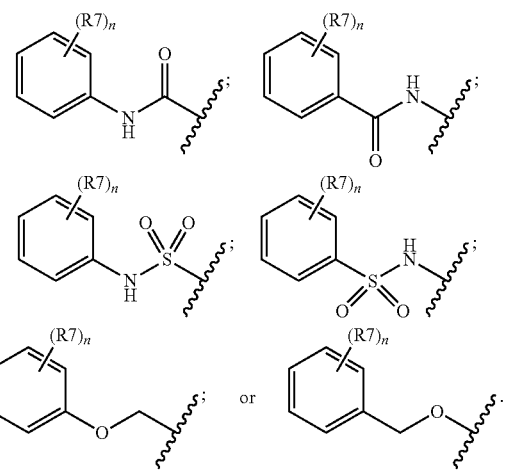

In various embodiments, R7 is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $C(O)C_{1-6}$-alkyl, —C(O)NHC$_{1-6}$-alkyl, —NHC(O)C$_{1-6}$-alkyl, —S(O)C$_{1-6}$-alkyl, —S(O)$_2$NHC$_{1-6}$-alkyl, —NHS(O)$_2$C$_{1-10}$-alkyl or a fully saturated or partially or fully unsaturated 3-8 membered monocyclic or 6-12 membered bicyclic ring system, the ring system formed of carbon atoms optionally including 1-3 heteroatoms if monocyclic or 1-6 heteroatoms if bicyclic, the heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of the ring system is optionally substituted independently with 1-5 substituents of halo, haloalkyl, haloalkoxyl, CN, $NO_2$, $NH_2$, OH, oxo, $C_{1-6}$-alkyl, $C_{1-6}$-alkoxyl, $C_{3-6}$-cycloalkyl, $C_{1-10}$-alkylamino-, $C_{1-10}$-dialkylamino-, benzyl or phenyl, or is a multi-ring moiety comprising at least one substituted or unsubstituted aromatic ring and at least one substituted or unsubstituted nonaromatic ring, or comprises at least one substituted or unsubstituted heteroaromatic ring. Subscript "n" is 0 or 1, 2, 3, 4, or 5.

In other embodiments, R5 of each of two of $G_1$, $G_2$, $G_3$, $G_4$, or $G_5$ taken together form a fully saturated or partially or fully unsaturated 3-8 membered monocyclic or 6-12 membered bicyclic ring system, the ring system formed of carbon atoms optionally including 1-3 heteroatoms if monocyclic or 1-6 heteroatoms if bicyclic, the heteroatoms selected from O, N, or S.

In various embodiments, the compound is a pyrrolo[2,3-d]pyrimidine. The pyrrolo[2,3-d]pyrimidine may be a compound of Formula (IV):

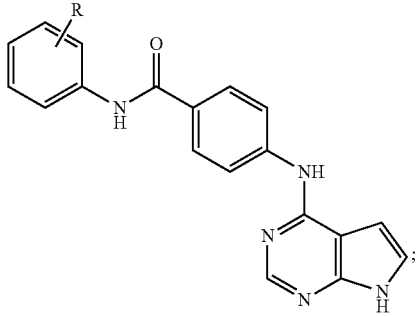
(IV)

wherein R is 2'-ClPh, 3'-ClPh, 4'-ClPh, 2'CH₃Ph, 3'CH₃Ph, 4'CH₃Ph, 2'-OCH₃Ph, 3'-OCH₃Ph, 4'-OCH₃Ph, 2'FPh, 3'FPh, 4'FPh, 2'-C₆H₅N, 3'-C₆H₅N, 4'-C₆H₅N, 2'-C₄H₆N₂, 3'-C₄H₆N₂, 4'-C₄H₆N₂, cyclohexyl, cyclopentyl, or tert-butyl. As used herein, "Ph" is phenyl.

The pyrrolo[2,3-d]pyrimidine may be a compound of Formula (V):

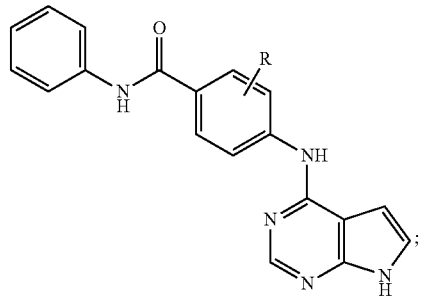
(V)

wherein R is 2-Cl, 3-Cl, 2-CH₃,3-CH₃, 2-F, 3-F, 2-OCH₃, or 3-OCH₃.

The pyrrolo[2,3-d]pyrimidine may be a compound of Formula (VI):

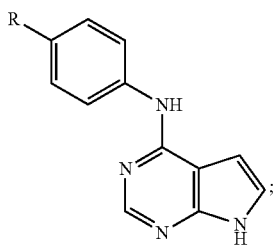
(VI)

wherein R is:

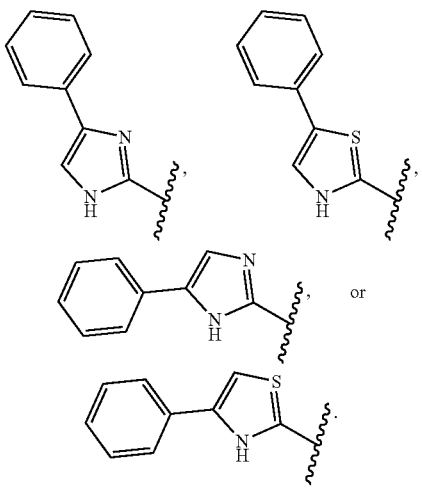

The pyrrolo[2,3-d]pyrimidine may be a compound of Formula (VII):

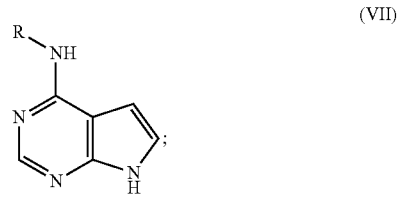
(VII)

wherein R is:

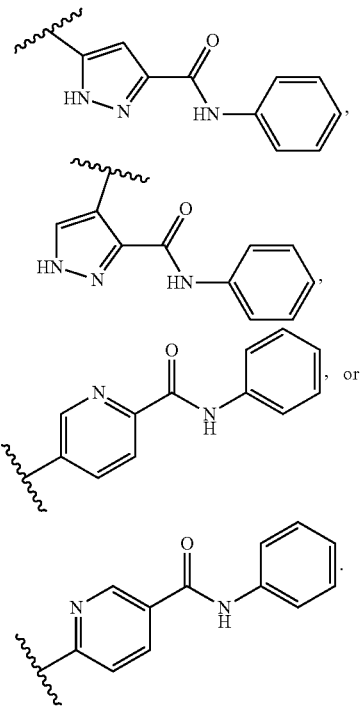

The pyrrolo[2,3-d]pyrimidine may be a compound of Formula (VIII):

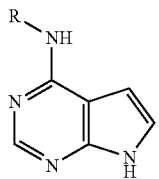
(VIII)

wherein R is:

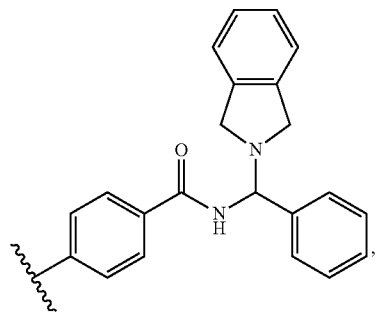

The pyrrolo[2,3-d]pyrimidine may be a compound of Formula (IX):

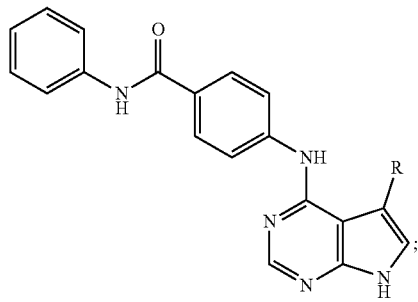
(IX)

wherein R is:

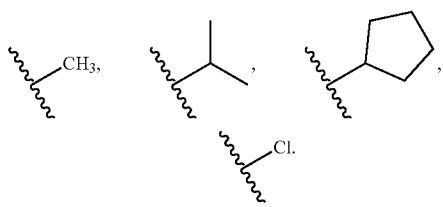

The pyrrolo[2,3-d]pyrimidine may be a compound of Formula (X):

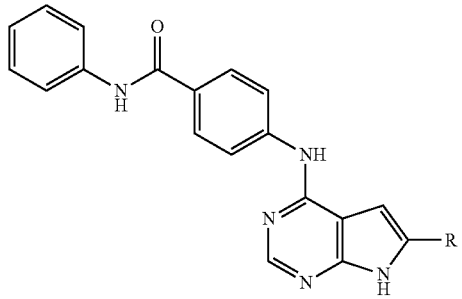
(X)

wherein R is:

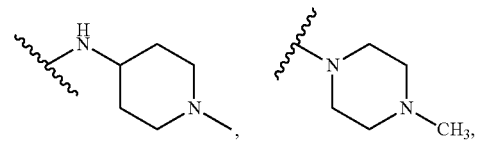

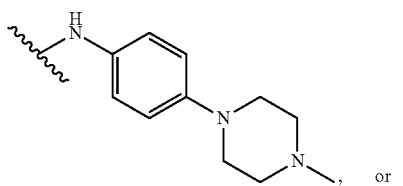, or

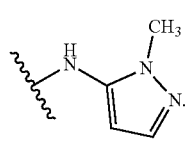

The pyrrolo[2,3-d]pyrimidine may be a compound of Formula (XI):

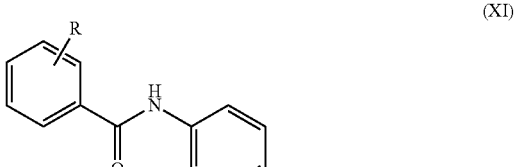
(XI)

wherein R is 2'-ClPh, 3'-ClPh, 4'-ClPh, 2'CH$_3$Ph, 3'CH$_3$Ph, 4'CH$_3$Ph, 2'-OCH$_3$Ph, 3'-OCH$_3$Ph, 4'-OCH$_3$Ph, 2'FPh, 3'FPh, 4'FPh, 2'-C$_6$H$_5$N, 3'-C$_6$H$_5$N, 4'-C$_6$H$_5$N, 2'-C$_4$H$_6$N$_2$, 3'-C$_4$H$_6$N$_2$, 4'-C$_4$H$_6$N$_2$, NHC$_6$H$_5$, CH$_2$C$_6$H$_5$, or CH$_2$CH$_2$C$_6$H$_5$.

The pyrrolo[2,3-d]pyrimidine may be a compound of Formula (XII):
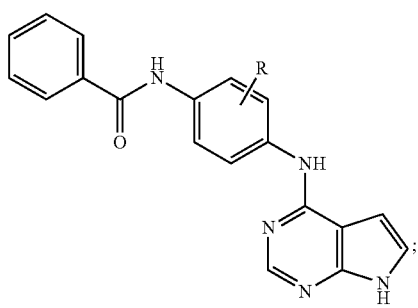
(XII)
wherein R is 2-Cl, 3-Cl, 2-CH₃, 3-CH₃, 2-F, 3-F, 2-OCH₃, or 3-OCH₃.
The pyrrolo[2,3-d]pyrimidine may be a compound of Formula (XIII):
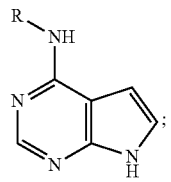
(XIII)
wherein R is:
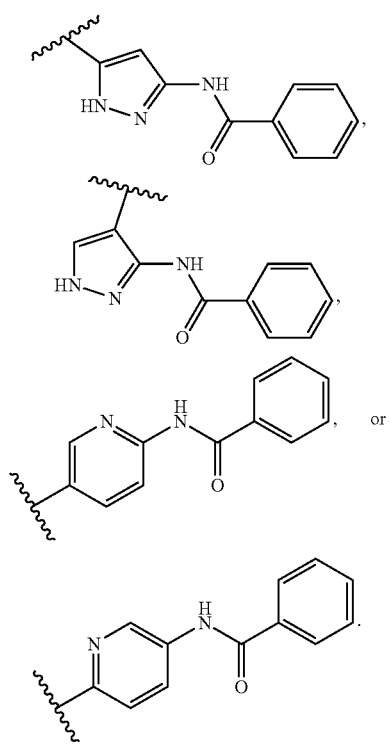
The pyrrolo[2,3-d]pyrimidine may be a compound of Formula (XIV):
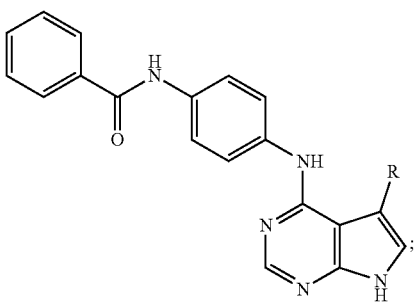
(XIV)
wherein R is:
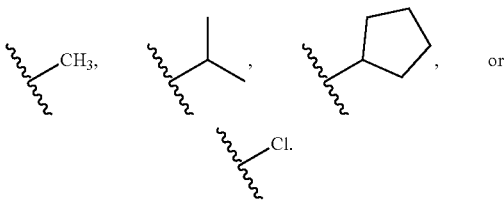
The pyrrolo[2,3-d]pyrimidine may be a compound of Formula (XV):
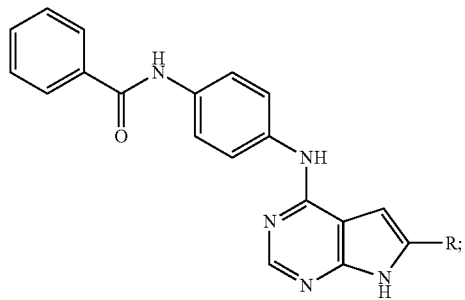
(XV)
wherein R is:
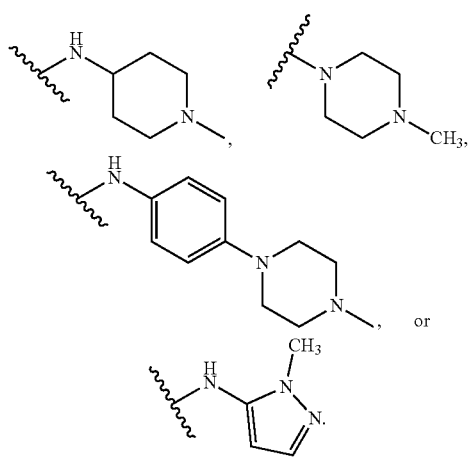

The pyrrolo[2,3-d]pyrimidine may be a compound of Formula (XVI):

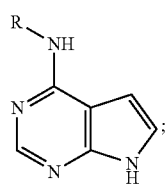
(XVI)

wherein R is:

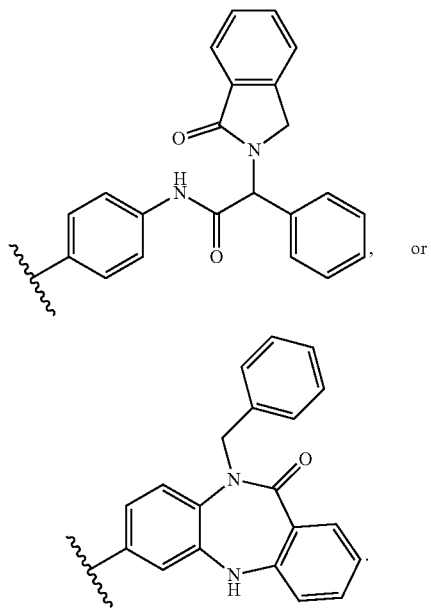

In various embodiments, the compound is a pyrazolopyrimidine. The pyrazolopyrimidines may be a compound of Formula (XVII):

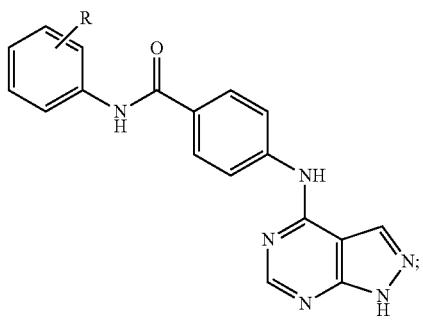
(XVII)

wherein R is 2'-ClPh, 3'-ClPh, 4'-ClPh, 2'CH₃Ph, 3'CH₃Ph, 4'CH₃Ph, 2'-OCH₃Ph, 3'-OCH₃Ph, 4'-OCH₃Ph, 2'FPh, 3'FPh, 4'FPh, 2'-C₆H₅N, 3'-C₆H₅N, 4'-C₆H₅N, 2'-C₄H₆N₂, 3'-C₄H₆N₂, 4'-C₄H₆N₂, cyclohexyl, cyclopentyl, or tert-butyl.

The pyrazolopyrimidine may be a compound of Formula (XVIII):

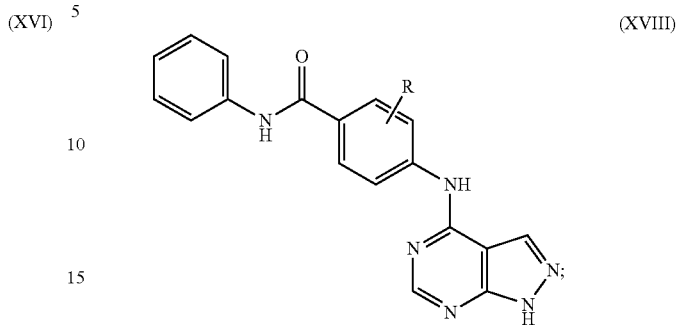
(XVIII)

wherein R is 2-Cl, 3-Cl, 2-CH3, 3-CH3, 2-F, 3-F, 2-OCH₃, or 3-OCH₃.

The pyrazolopyrimidine may be a compound of Formula (XIX):

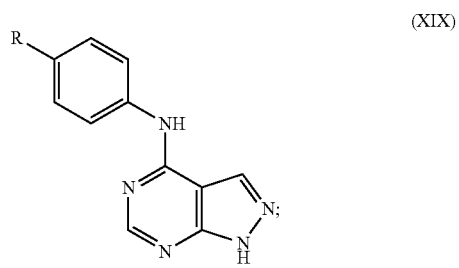
(XIX)

wherein R is:

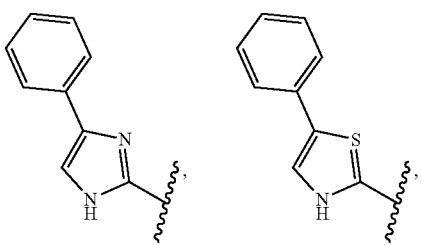

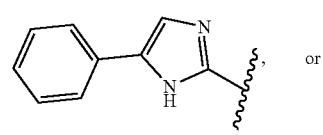, or

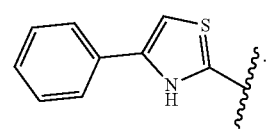

The pyrazolopyrimidine may be a compound of Formula (XX):
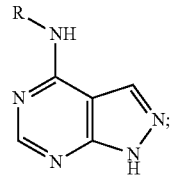
(XX)
wherein R is:
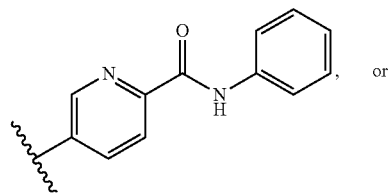, or
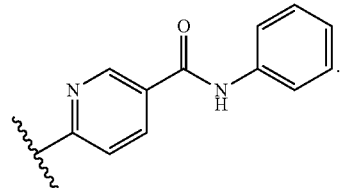.
The pyrazolopyrimidine may be a compound of Formula (XXI):
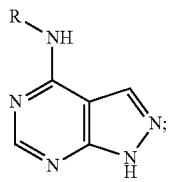
(XXI)
wherein R is:
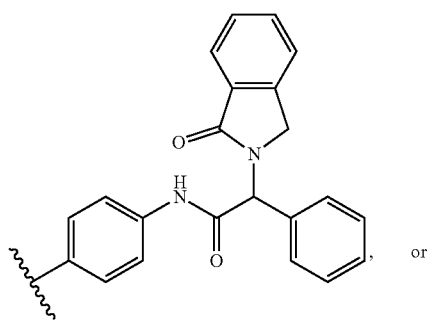, or
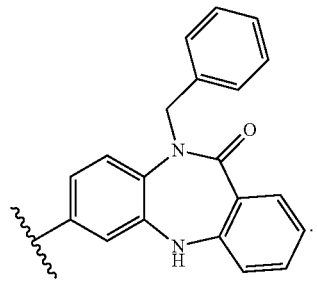
The pyrazolopyrimidine may be a compound of Formula (XXII):
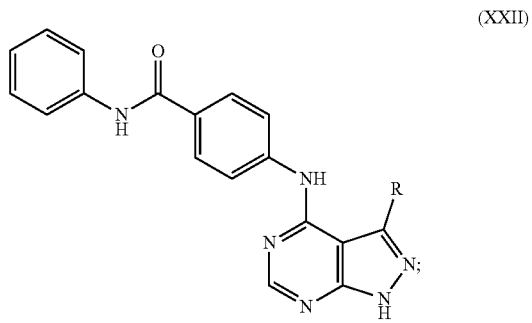
(XXII)
wherein R is:
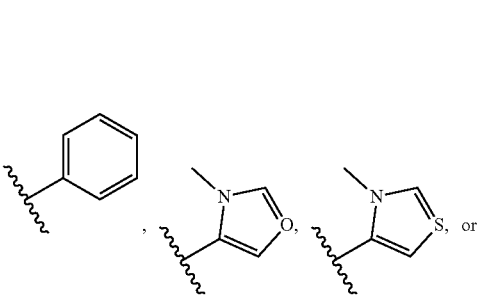
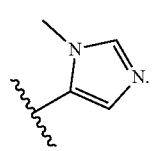

The pyrazolopyrimidine may be a compound of Formula (XXIII):

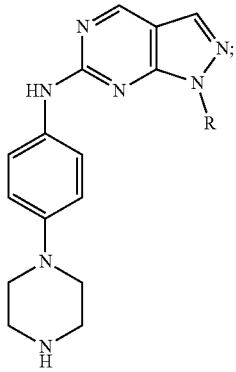
(XXIII)

wherein R is:

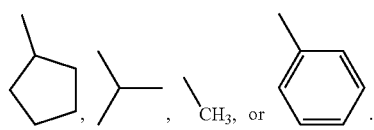

In some exemplary embodiments, the pyrazolopyrimidine is:

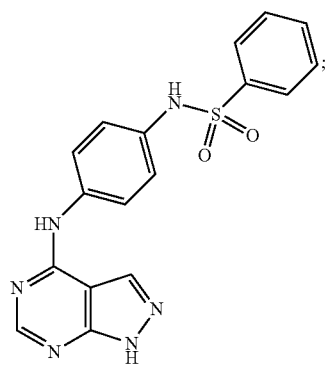

;

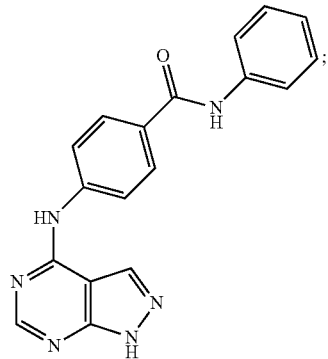

;

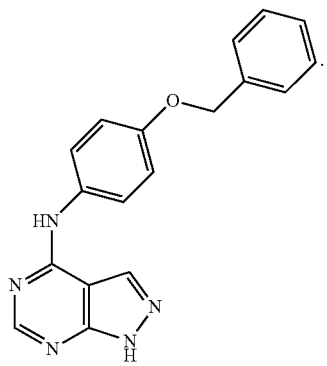

; or

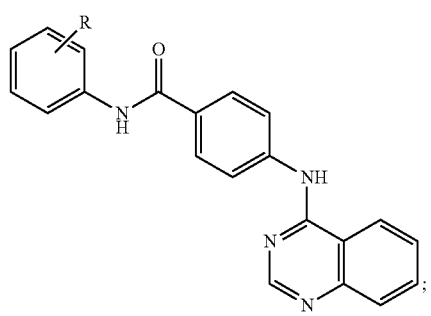

.

In various embodiments, the compound is a quinazolines. The quinazolines may be a compound of Formula (XXIV):

(XXIV)

wherein R is 2'-ClPh, 3'-ClPh, 4'-ClPh, 2'CH$_3$Ph, 3'CH$_3$Ph, 4'CH$_3$Ph, 2'-OCH$_3$Ph, 3'-OCH$_3$Ph, 4'-OCH$_3$Ph, 2'FPh, 3'FPh, 4'FPh, 2'-C$_6$H$_5$N, 3'-C$_6$H$_5$N, 4'-C$_6$H$_5$N, 2'-C$_4$H$_6$N$_2$, 3'-C$_4$H$_6$N$_2$, 4'-C$_4$H$_6$N$_2$, cyclohexyl, cyclopentyl, or tert-butyl.

The quinazolines may be a compound of Formula (XXV):
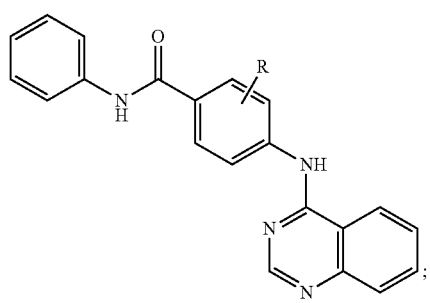
(XXV)
wherein R is 2-Cl, 3-Cl, 2-CH₃, 3-CH₃, 2-F, 3-F, 2-OCH₃, or 3-OCH₃.
The quinazolines may be a compound of Formula (XXVI):
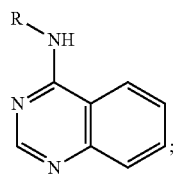
(XXVI)
wherein R is:
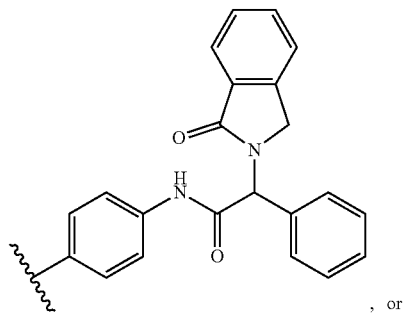
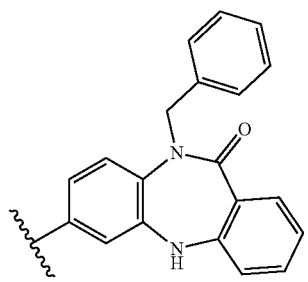
, or
.
The quinazolines may be a compound of Formula (XXVII):
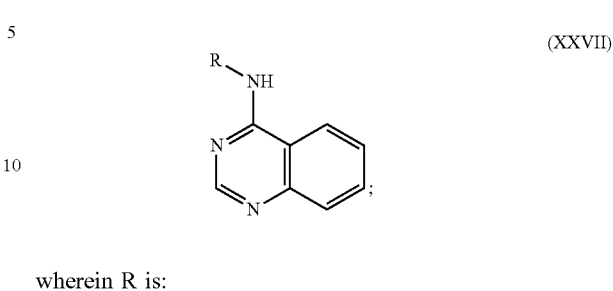
(XXVII)
wherein R is:
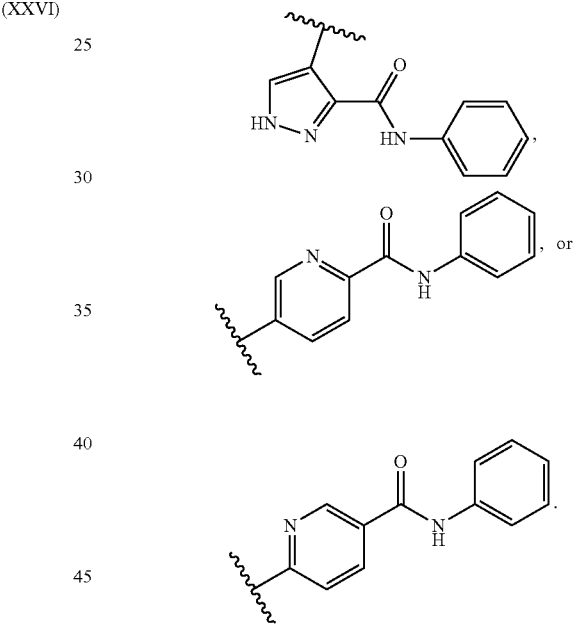
, or
.
The quinazolines may be a compound of Formula (XXVIII):
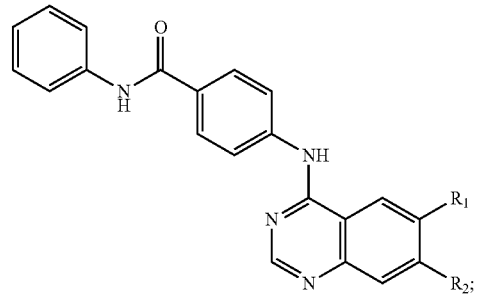
(XXVIII)

wherein one of R1 and R2 is:

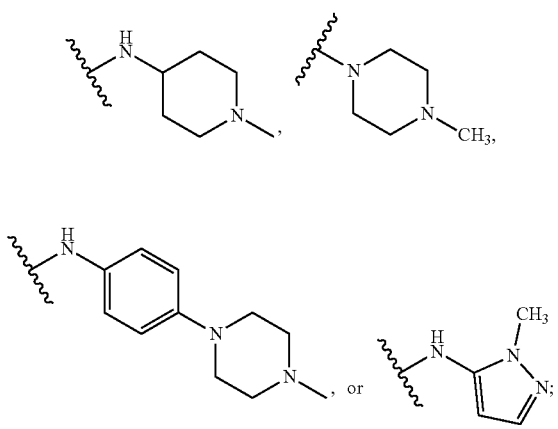

with the proviso that the other of R1 and R2 is H.

The quinazolines may be a compound of Formula (XXIX):

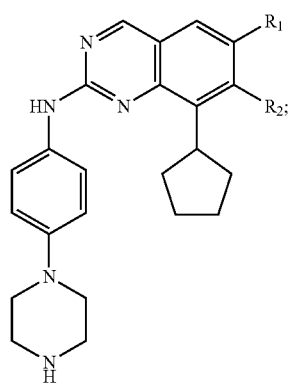

wherein one of R1 and R2 is:

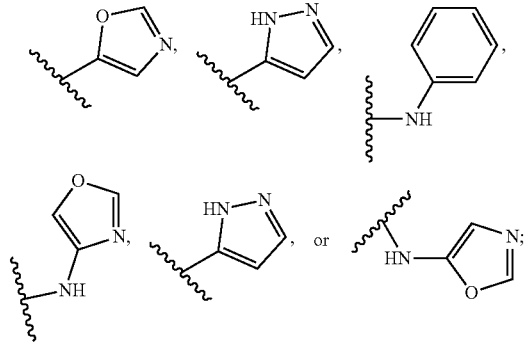

with the proviso that the other of R1 and R2 is H.

In various embodiments, the compound is a 2,6,7-trisubstituted pyrrolo[2,3-d]pyrimidines. The 2,6,7-trisubstituted pyrrolo[2,3-d]pyrimidines may be a compound of Formula (XXX):

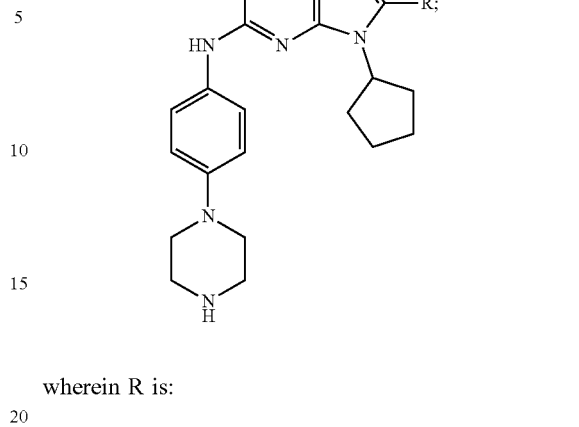

wherein R is:

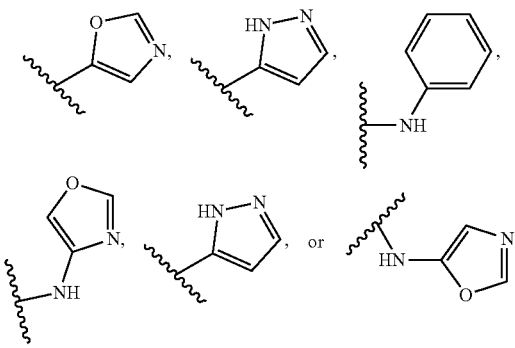

The 2,6,7-trisubstituted pyrrolo[2,3-d]pyrimidines may be a compound of Formula

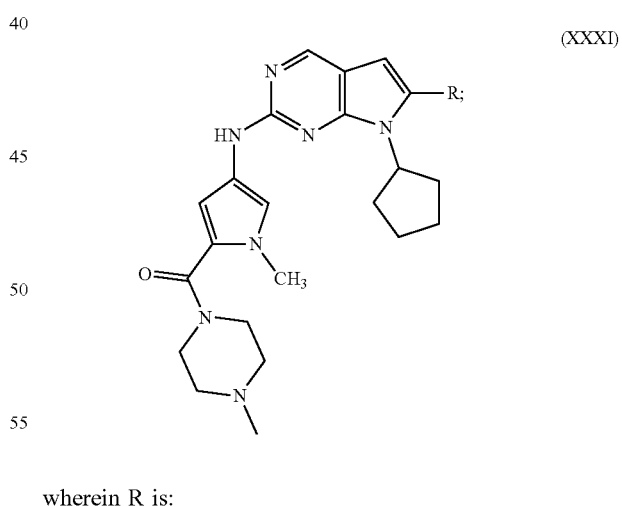

wherein R is:

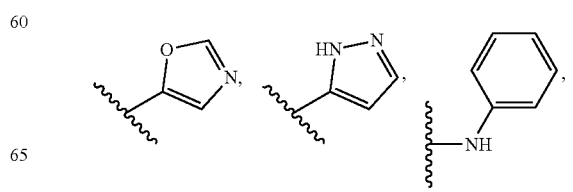

-continued

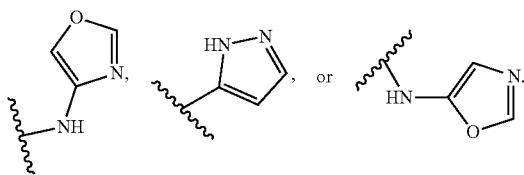

The 2,6,7-trisubstituted pyrrolo[2,3-d]pyrimidines may be a compound of Formula (XXXII):

(XXXII)

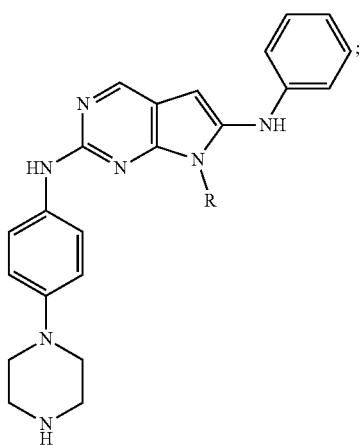

wherein R is:

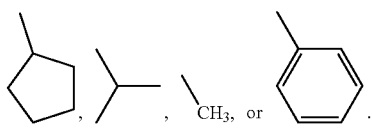

The 2,6,7-trisubstituted pyrrolo[2,3-d]pyrimidines may be a compound of Formula (XXXIII):

(XXXIII)

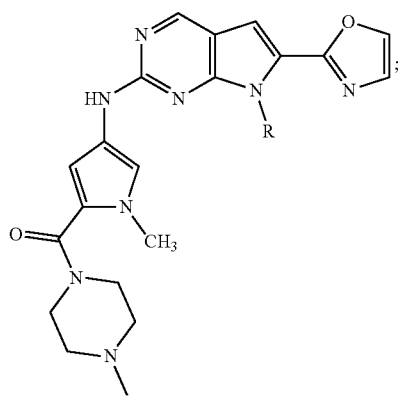

wherein R is:

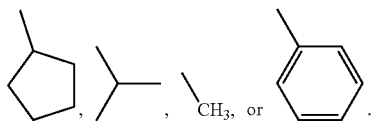

In other embodiments, the compound may be of Formula (XXXIV):

(XXXIV)

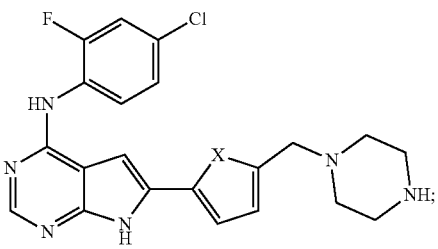

wherein X is O, S, NH, or C≡C.

The compound may be of Formula (XXXV):

(XXXV)

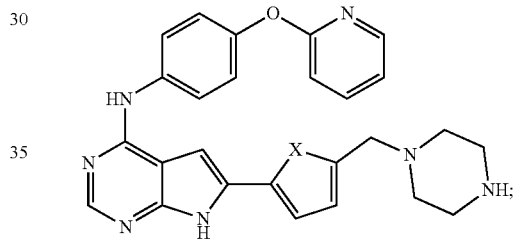

wherein X is O, S, NH, or C≡C.

In some exemplary embodiments, the compound is:

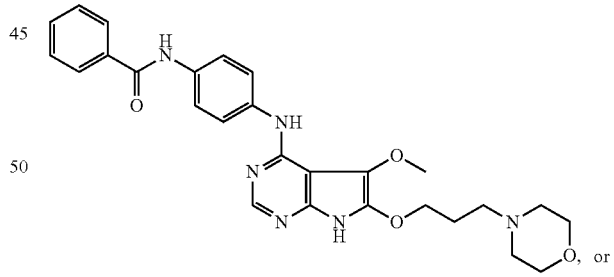

, or

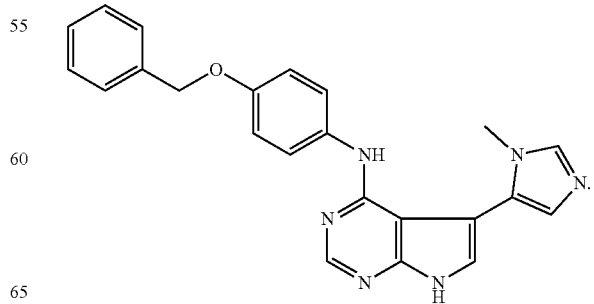

In various embodiments, the compound is a 2,4,7-trisubstituted pyrrolo[2,3-d]pyrimidines. The 2,4,7-trisubstituted pyrrolo[2,3-d]pyrimidines may be a compound of Formula (XXXVI):

(XXXVI)

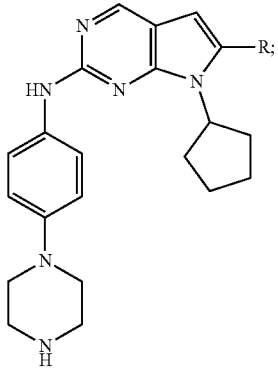

wherein R is:

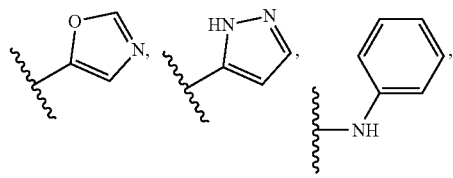

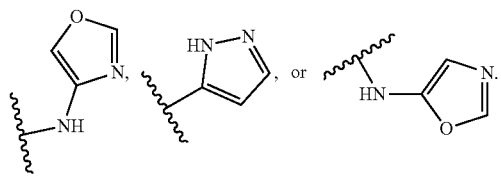

The 2,4,7-trisubstituted pyrrolo[2,3-d]pyrimidines may be a compound of Formula (XXXVII):

(XXXVII)

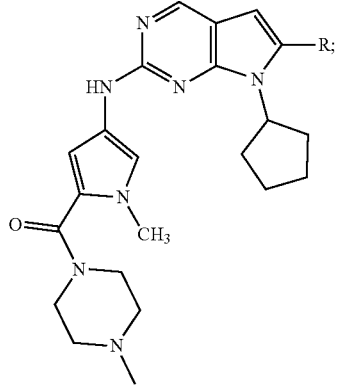

wherein R is:

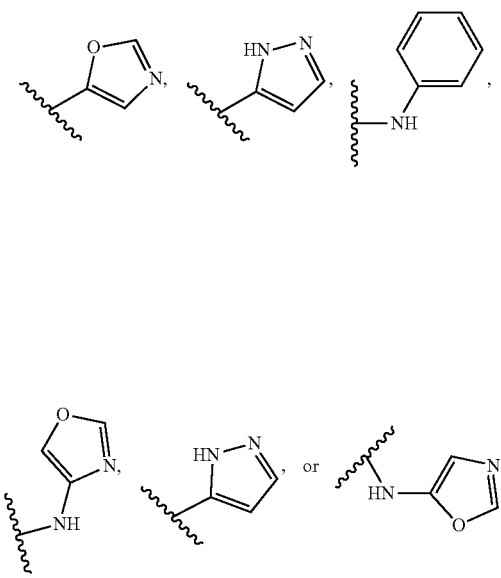

The 2,4,7-trisubstituted pyrrolo[2,3-d]pyrimidines may be a compound of Formula (XXXVIII):

(XXXVIII)

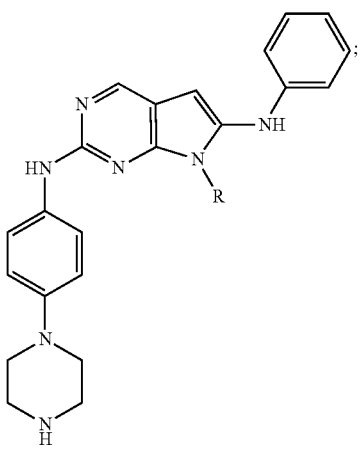

wherein R is:

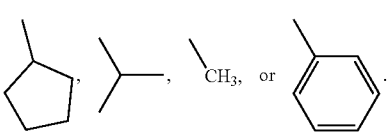

The 2,4,7-trisubstituted pyrrolo[2,3-d]pyrimidines may be a compound of Formula (XXXIX):
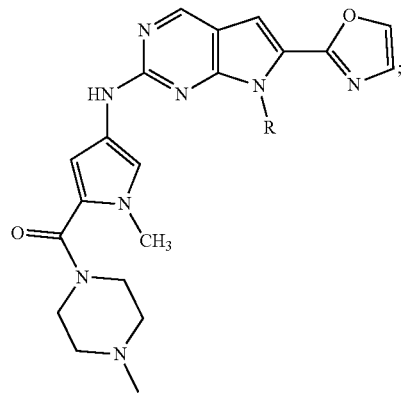
(XXXIX)
wherein R is:
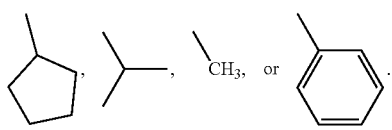
In various embodiments, the compound is a 2,7,8-trisubstituted quinazoline. The 2,7,8-trisubstituted quinazoline may be substituted as described in Formulas (I) to (XXXIX) above.
In some exemplary embodiments, the compound is:
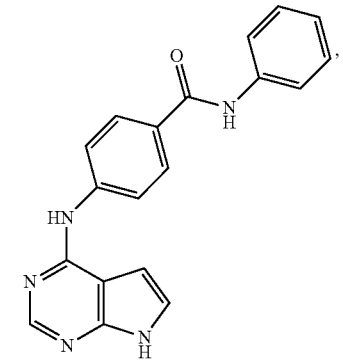
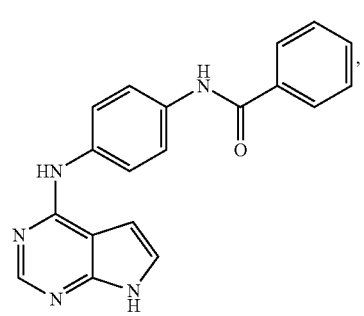
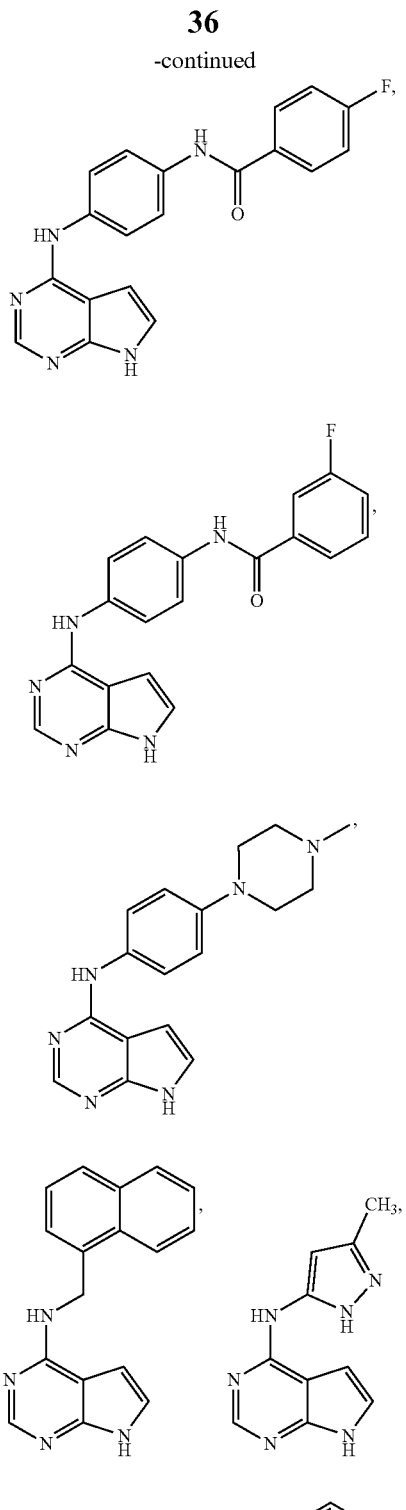

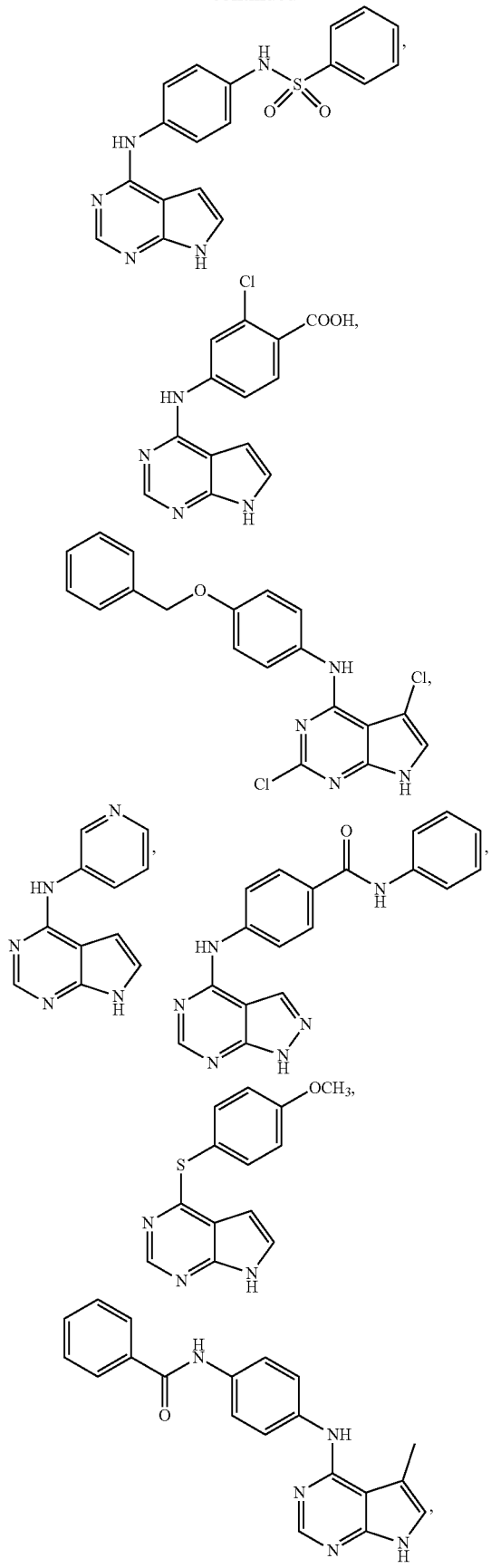

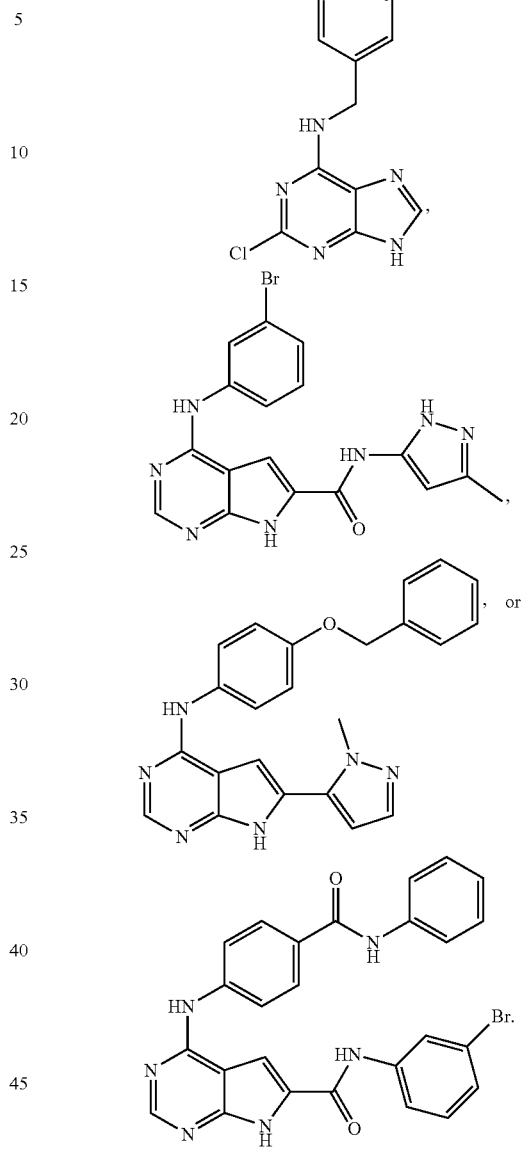

Also included in the family of compounds described herein, e.g. Formulas (I) to (III), are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of the compounds may be prepared from an inorganic acid or from an organic acid. Examples of such inorganic acids include, without limitation, hydrochloric, hydrobromic, hydroiodic, nitric, carbonic, sulfuric and phosphoric acid. Examples of organic acids include, without limitation, aliphatic, cycloaliphatic, aromatic, arylaliphatic, heterocyclic, carboxylic and sulfonic classes of organic acids, examples of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, p-hydroxybutyric, salicylic, galactaric and galacturonic acid.

Suitable pharmaceutically-acceptable base addition salts of the compounds include, without limitation, metallic salts such as salts made from aluminum, calcium, lithium, magnesium, potassium, sodium and zinc, or salts made from organic bases including primary, secondary, tertiary amines and substituted amines including cyclic amines such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of the salts contemplated herein may be prepared by conventional means from the corresponding compound by reacting, for example, the appropriate acid or base with the compound. When a basic group and an acid group are present in the same molecule, a compound may also form internal salts.

Method of Forming Compounds

With reference to FIGS. 1-5, the synthesis for various compounds of Series I-XII are described in Schemes 1-7 below. The synthetic procedures utilized are adapted from well documented protocols such as organometallic couplings and can be applied to the pyrrolo[2,3-d]pyrimidine scaffold. Synthetic routes that have been well established have been incorporated for compound synthesis. The reactions can be monitored via thin layer chromatography for reaction completion and purified using normal phase flash chromatography (Teledyne Isco) with gradient elution (10% methanol/chloroform). Percent yields can be determined for each reaction. To ensure rigor, compound identity can be confirmed by $^1H$, $^3C$, $^{19}F$ nuclear magnetic resonance (NMR) and LC-MS analysis using the Shimadzu research core. For accurate mass determination, high-resolution mass analysis (HRMS) can be utilized. Percent purity can be determined by analytical HPLC (Shimadzu Core). All synthetic reagents can be purchased, for example, from Millipore Sigma. The purchased chemicals can be authenticated in lab using NMR and mass analysis. All novel compounds and products of novel reactions can be authenticated using NMR, melting point determination, HRMS and elemental analysis.

Series I and II can be synthesized in two ways, as shown in Scheme 1 below. One approach may involve the nucleophilic displacement of 80 (commercially available from Millipore Sigma) with the amino substituted benzoic acid 81. The carboxylic acid 82 may be converted to the corresponding acid chloride 83 with thionyl chloride. Phosphorus oxychloride may also be used as an alternate for acid chloride synthesis. Displacement with the appropriate aniline under basic conditions may yield Series I and II. Another approach may involve the synthesis of the appropriate amino benzanilide, first followed by nucleophilic substitution of as shown in Scheme 1. In the event that nucleophilic displacement is not suitable, a palladium catalyzed Buchwald-Hartwig coupling protocol may be utilized. In the event that the acid chloride displacement between 83 and 84 is not suitable, a standard peptide coupling protocol may be utilized. The acid in 85 may be activated using hydroxybenzotriazole (HOBt), hexafluorophosphate benzotriazole tetramethyl uronium (HBTU) in dimethylformamide (DMF) as solvent followed by reaction with the appropriate aniline 84 in the presence of diethylamine to yield Series I and II.

Figure 15:
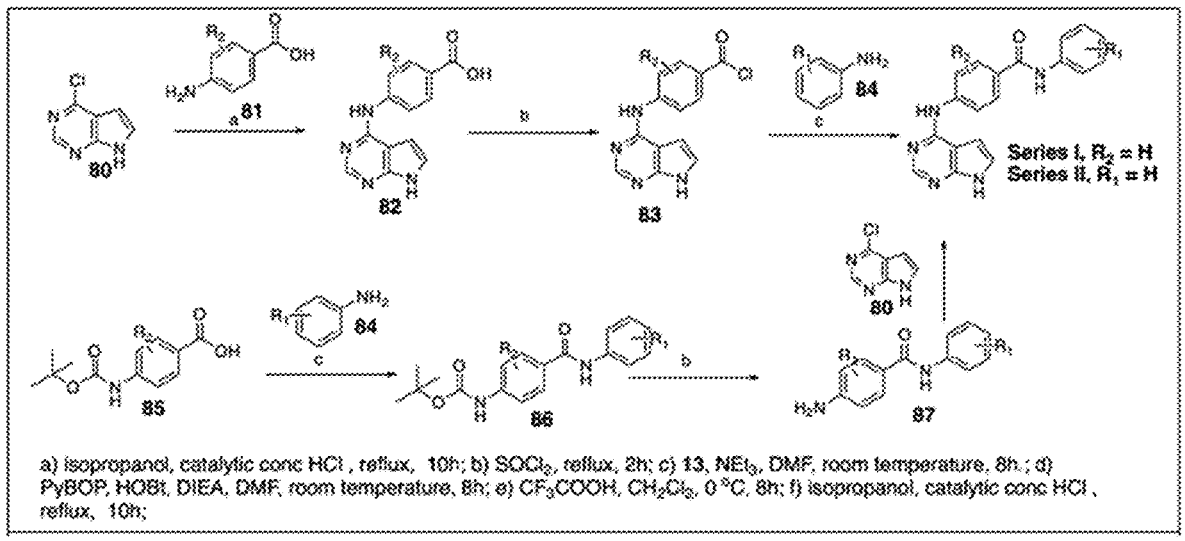
FIGS. 15-21 are synthesis schemes illustrating non-limiting embodiments of methods of forming compounds.

Scheme 1: Synthesis of Compounds in Series I and II. See FIG. 15.

Series III may be synthesized as described in Scheme 2 below using similar methods as described in Scheme 1 above. The appropriate heteroaromatic iodides may be purchased from Millipore Sigma. Reaction with bispinacolborane using the Miyaura borylation protocol may yield the corresponding boronates. Suzuki coupling with commercially available tert-butyloxycarbonyl (Boc) protected aryl bromide may yield 91.

Protection of the NH in 88 may be necessary to prevent side reactions and lower yields. The amine may be protected by 2-(trimethylsilyl)ethoxymethyl (SEM) chloride. Alternate bases, reaction conditions and palladium catalysts may be attempted. In the event that the Miyaura borylation or Suzuki coupling does not proceed as expected, one can attempt alternate direct coupling protocols such as Heck coupling or nickel catalyzed Negishi coupling. Deprotection of the Boc group in 91 under acidic conditions followed by nucleophilic substitution of 80 may yield Series III. Deprotection of 91 to yield 92, followed by nucleophilic substitution of 80 as described under preliminary studies should afford Series III.

Figure 16:
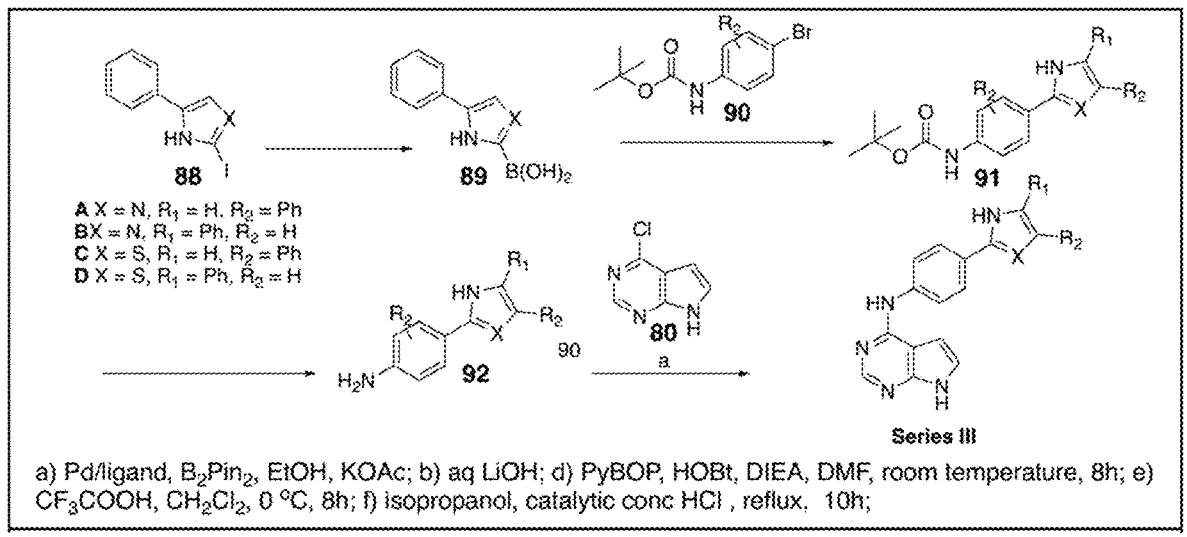

Scheme 2: Synthesis of Series III. See FIG. 16.

Series IV may be synthesized similar to Scheme 1 above using the appropriately substituted amino pyrazole or aminopyridine. A nucleophilic substitution reaction on 80 with 3-aminopyrazole may yield 94. The acid group may be further reacted with aniline, using 1-(3-dimethylaminopropyl)-3-ethylcarbodiimide hydrochloride (EDC) to give the corresponding acetanilide, or alternatively converted to the corresponding acid chloride using thionyl chloride followed by displacement by aniline in pyridine to 47. Aminopyrazole or aminopyridine may be utilized to synthesize 93-97 as described for 47.

Figure 17:
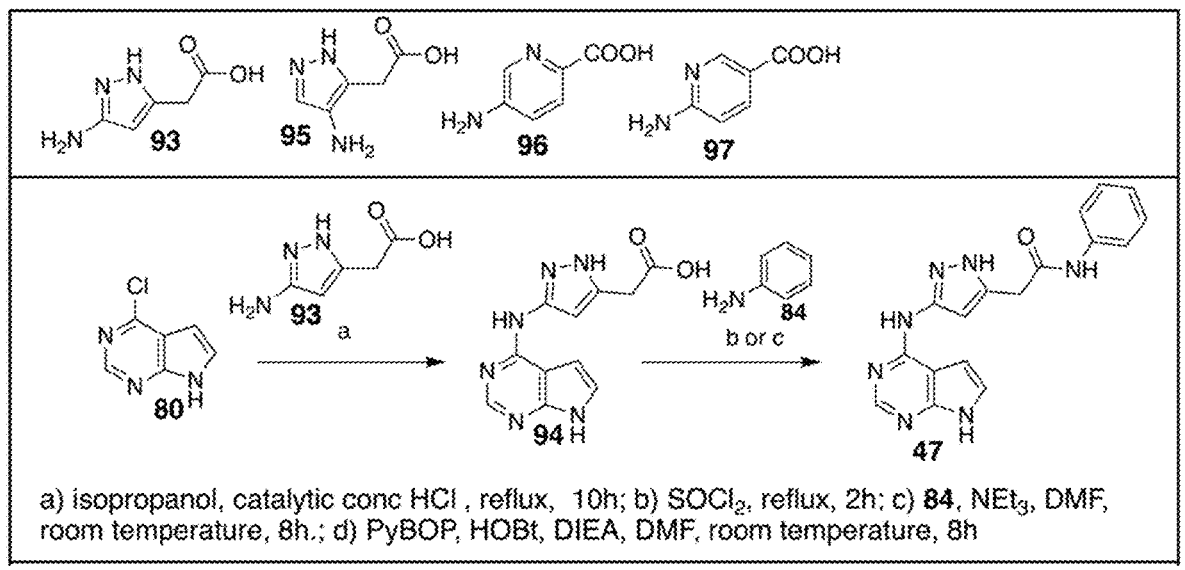

Scheme 3: Synthesis of Series IV. See FIG. 17.

Series V may be synthesized as described in Scheme 4 below. Synthesis of 51 may involve a nucleophilic displacement of 80 with the appropriately substituted amine 99. Starting material 80 for Series V may also be commercially available from Millipore Sigma.

Figure 18:
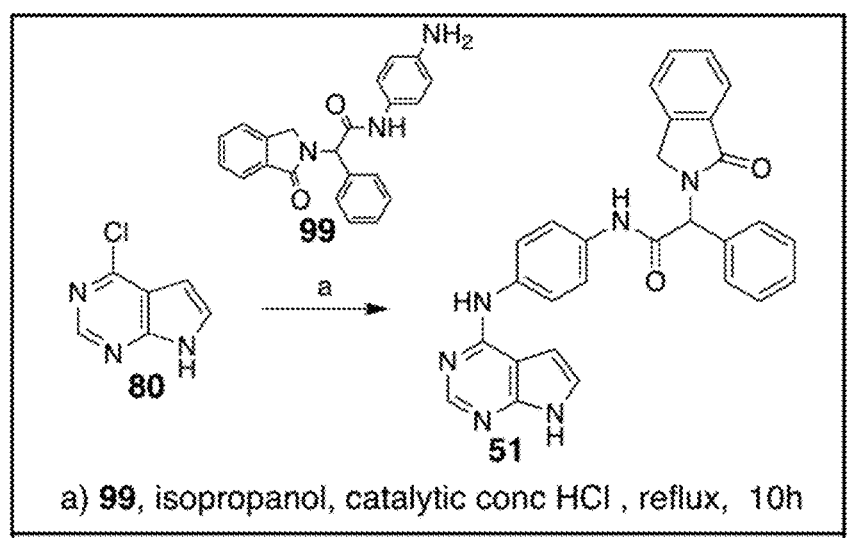

Scheme 4: Synthesis of Series V. See FIG. 18.

Series VI may be synthesized as described in Scheme 5 below. The reaction of starting material 100 with SEM chloride may yield 101. In the event that SEM chloride is not suitable, trityl chloride may be utilized. Suzuki coupling with the appropriate alkyl/aryl boronates may be utilized to yield 102. The protocol may involve reaction for 20 hours at 100° C. or reaction under microwave catalyzed conditions, such as microwave catalyzed organometallic coupling reactions.

Figure 19:
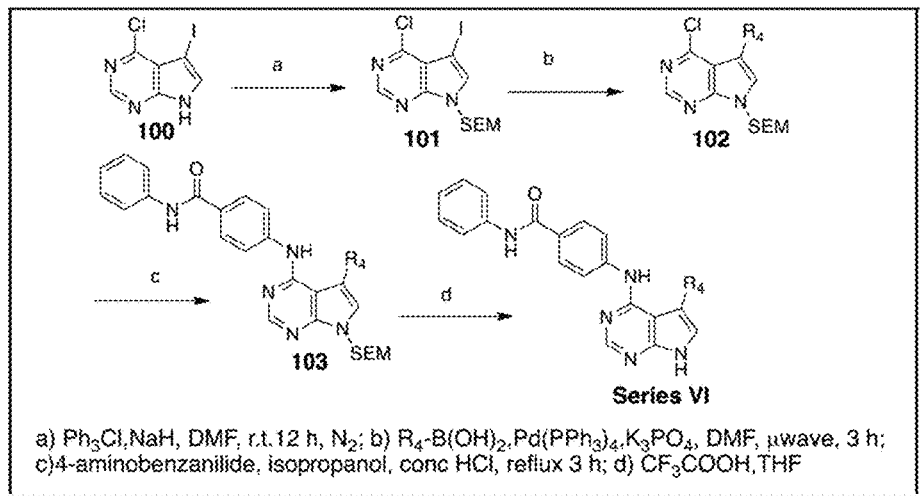

Scheme 5: Synthesis of Series VI. See FIG. 19.

Series VII may be synthesized similar to Series I using nucleophilic displacement of 102 with the appropriate aniline followed by acid catalyzed deprotection of the SEM group may be utilized to yield Series VII. Nucleophilic displacement with the appropriate aniline followed by SEM deprotection may be used to yield Series VII as shown in Scheme 6 below.

Figure 20:
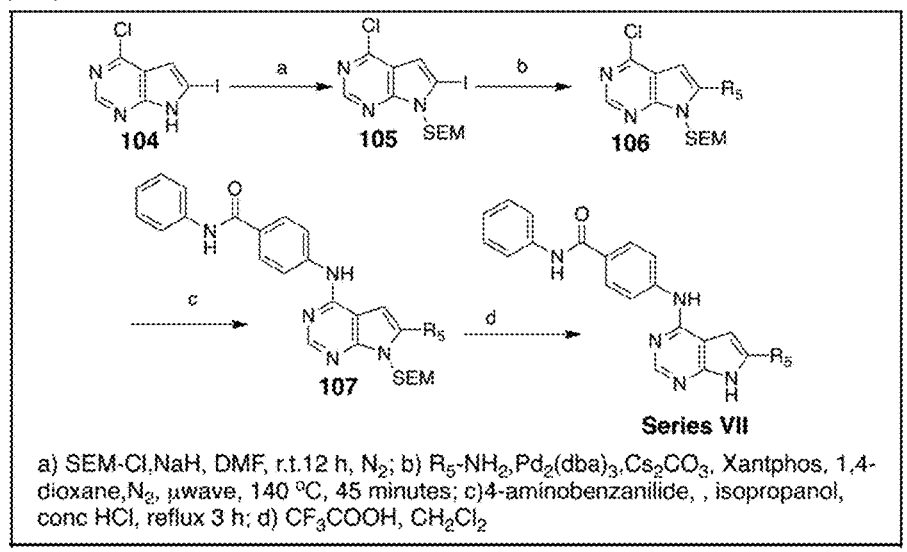

Scheme 6: Synthesis of Series VII. See FIG. 20.

Series VIII-XI may be synthesized as described in Scheme 7 below. For example, compounds in Series X and XI are close analogs of pyrrolopyrimidines reported by Le Brazidec et al. Structure-based design of 2,6,7-trisubstituted-7H-pyrrolo[2,3-d]pyrimidines as Aurora kinases inhibitors. *Bioorg Med Chem Lett* 2012, 22, 4033-4037, which is hereby incorporated by reference in its entirety, and can be synthesized as reported. An alternate synthetic protocol as described by Skelton et al. Preparation of bicyclic heteroaryl derivatives as AKT protein kinase inhibitors. World Intellectual Property Organization, WO2013078254 A1 (2013 May 30), which is hereby incorporated by reference in its entirety, could also be utilized as described in Scheme 7 starting from commercially available 108. Base catalyzed alkylation of the pyrrole nitrogen using the procedure described by Planken et al. Discovery of N-((3R, 4R)-4-Fluoro-1-(6-((3-methoxy-1-methyl-1H-pyrazol-4-yl)amino)-9-methyl-9H-purin-2-yl)pyrrolidine-3-yl) acrylamide (PF-06747775) through Structure-Based Drug Design: A High Affinity Irreversible Inhibitor Targeting Oncogenic EGFR Mutants with Selectivity over Wild-Type EGFR. *J. Med. Chem.* 2017, 60, 3002-3019, which is hereby incorporated by reference in its entirety, or using a Mitsunobu alkylation as an alternate route for N7 alkylation. Suzuki coupling of the 6-iodo followed by palladium catalyzed coupling of the 2-chloro under inert conditions will yield Series VIII-IX. This has been previously described by Miyaura et al. Palladium-Catalyzed Cross-Coupling Reactions of Organoboron Compounds. *Chem. Rev.* 1995, 95, 2457-2483 for aryl iodides, and Zhang et al. Palladium-Imidazol-2-ylidene Complexes as Catalysts for Facile and Efficient Suzuki Cross-Coupling Reactions of Aryl Chlorides with Arylboronic Acids. *J. Org. Chem.* 1999, 64, 3804-3805 for aryl chlorides, which are hereby incorporated by reference in their entirety.

Figure 21:
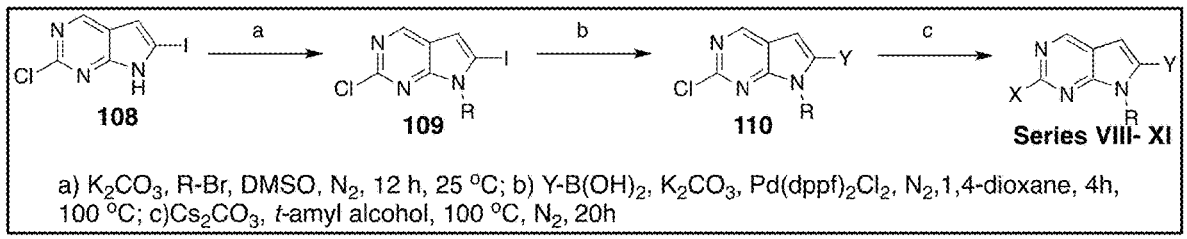

Scheme 7: Synthesis of Series VIII-XI. See FIG. 21.

Series XII may be synthesized similar to Scheme 6 described previously for Series VII using the appropriately substituted boronic acid and 105. Compound 11 of Series XII can be synthesized using modification of the protocol reported for Series VI. Other pyrazolopyrimidine-based compounds may be formed in accordance with Radi et al. *J. Med. Chem.* 2013, 56, 5382-5394 and Gehringer et al. *ChemMedChem* 2014, 9, 2516-2527, which are hereby incorporated by reference in their entirety. Tricyclic-based compounds may be formed in accordance with Gehringer et al. *ChemMedChem* 2014, 9, 2516-2527 and Zhang et al. Bioorganic & Medicinal Chemistry 19 (2011) 3585-3594, which are hereby incorporated by reference in their entirety.

Method of Identifying Compounds

Figure 6:
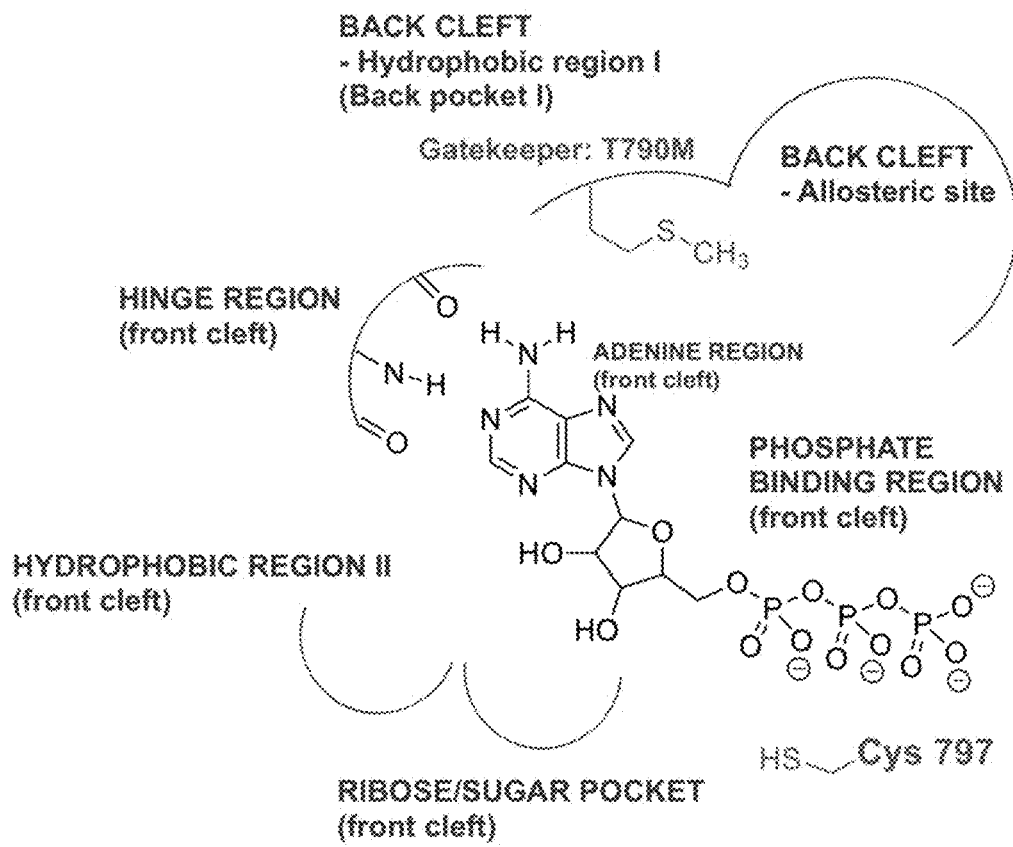
FIG. 6 is a representation of a chemical structure illustrating a non-limiting embodiment of the compound in a binding pocket.

With reference to FIG. 6, the ATP pocket of kinases may be made up of different regions. The first-generation EGFR inhibitors, erlotinib and gefitinib may be reversible. Type I inhibitors may bind to the active state of EGFR and interact with the ATP site and the smaller hydrophobic pocket (hydrophobic region I) of the back cleft. Afatinib and osimertinib may bind within the ATP pocket of EGFR similar to Type I inhibitors and may target a cysteine residue adjacent to the ATP site. Type II EGFR inhibitors, lapatinib and neratinib are also EGFR inhibitors. These Type II EGFR inhibitors may demonstrate allosteric as well as ATP-competitive kinase inhibition. These Type II EGFR include long hydrophobic sidechains that extend deep within hydrophobic pocket of the back cleft accessing the allosteric site.

Figure 7:
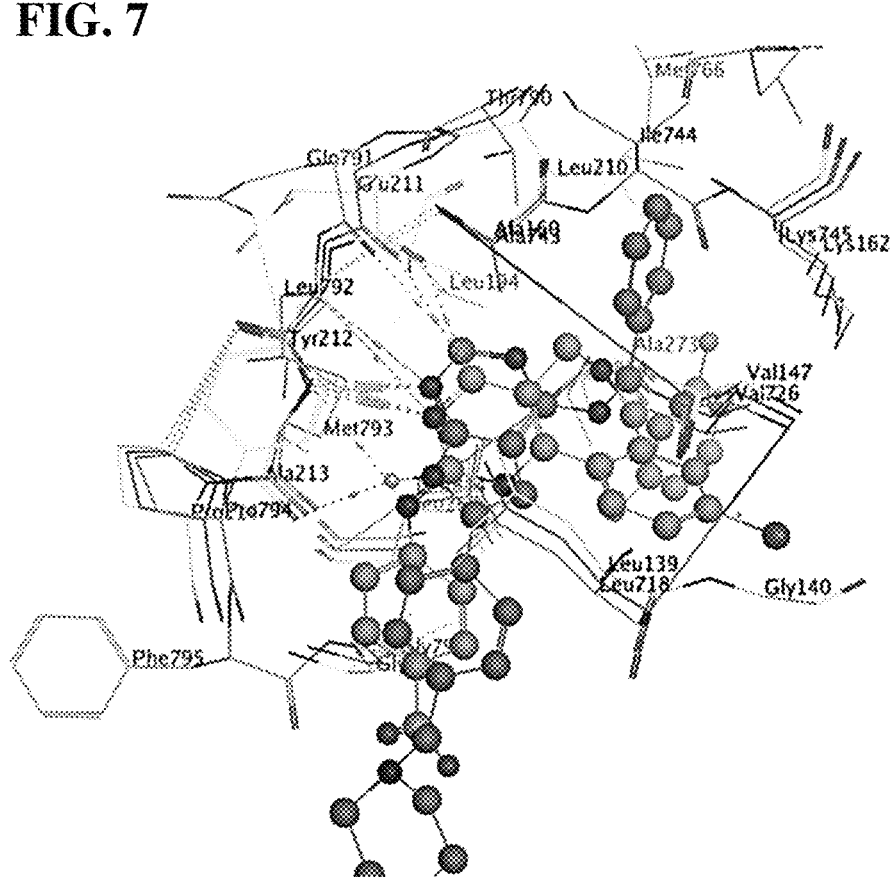
FIG. 7 is another representation of a chemical structure illustrating a non-limiting embodiment of the compound in a binding pocket.
Figure 8:
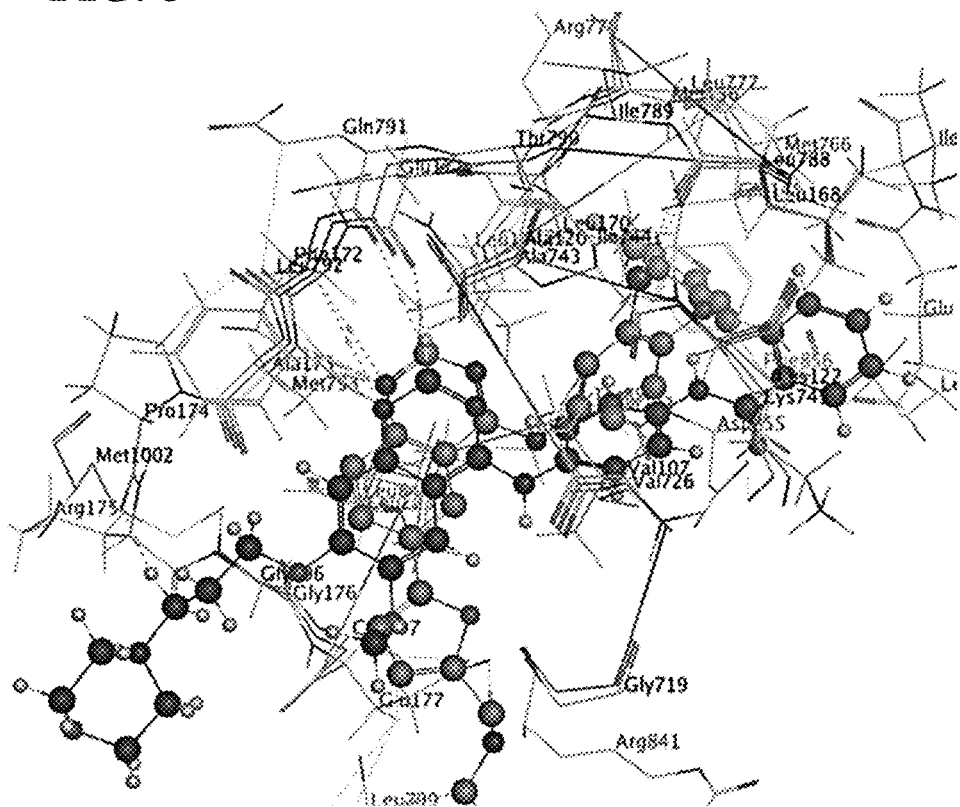
FIG. 8 is another representation of a chemical structure illustrating a non-limiting embodiment of the compound in a binding pocket.

With reference to FIGS. 7 and 8, the AURK inhibitors may be ATP-competitive with distinct modes of binding to the ATP pocket of AURKA and AURKB. Alisertib, a selective AURKA inhibitor, may bind predominantly in the front cleft with interactions observed with the hinge region residues, Ala 213 and Met 793 and interactions within the ribose pocket, adenine region and phosphate binding region, and minimal interactions in Hydrophobic region I and the back pocket. Selective AURKB inhibitors such as barasertib and ZM 447439 may bind within the hinge region, adenine region and incorporate sidechains that interact within hydrophobic region I and extend further into the back cleft of AURKB.

The ATP binding site from reported crystal structures of EGFR in the inactive Type II conformation (PDB code: 2JIV), EGFR in the Type I active conformation (PDB code: 1M17), L858R EGFR (PDB code: 2ITT), AURKA from (PDB code: 3E5A) and AURKB (PDB code: 2VRX) and the computational software, Molecular Operating Environment (MOE 2019.10) suite may be utilized as starting points for modeling experiments. Alignment may be conducted using the Align/minimize feature in MOE to determine similarities and differences in the pockets. Aligned poses may be viewed to note any major geometrical changes and deviations from the crystallized pose.

With particular reference to FIG. 7, the ATP pocket of EGFR (active conformation) overlapped with the ATP pocket of AURKA is shown. With particular reference to FIG. 8, the ATP pocket of EGFR in the inactive conformation overlapped with AURKB is shown. In various embodiments, the pockets show several similarities among the different regions both based on size and sequence homology. The sequence similarity between the ATP pockets of EGFR and AURK may be calculated using the program in MOE and root mean square deviation (rmsd) may be 0.87 for EGFR in the inactive conformation and AURKB and may be 0.83 for EGFR in the active conformation and AURKA. In certain embodiments, values of rmsd<1 indicate high similarity. The amino acids in the hydrophobic region I and ribose pocket may largely overlap between EGFR and AURK. The allosteric pocket shown in FIG. 8 having the inactive conformation of EGFR may overlay on the back pocket of AURKB.

Variations may be found in the amino acids of the hinge region of EGFR and AURKs, however the hinge region amino acids may interact through their common peptide backbone and may be found to overlay in their interaction pattern of one hydrogen bond donor and one hydrogen bond acceptor. This may be seen through the backbone carbonyl and amide NH for AURKA (through Ala 213), EGFR (through Met793 and Leu 792) and AURKB (through Ala 173). As a result, variations in binding may not be expected for the hinge region of EGFR and AURK. To ensure rigor, the alignment protocols may be repeated with different reported crystal structures for EGFR including (1XKK, 3W33), AURKA (4DHF), and AURKB (4AF3, 5EYK) and may yield similar results for sequence similarity and orientation of residues in the ATP pocket.

Salts, Pro-Drugs, Etc.

The invention further includes salt forms of the compounds. Salts of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Suitable acid and base addition salts are further described in the Definition Section herein.

The invention further encompasses pro-drugs of the compounds. For example, a phosphate group may be a pro-drug derivative of an alcohol group or an amine group, or an ester may be a pro-drug of a carboxylic acid functional group. Phosphate groups may be incorporated into desired compounds in order to improve upon in-vivo bioavailability and/or other pharmacokinetic (pK) or pharmacodynamic (PD) properties of the compound.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with chiral reagents, such as an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may also be represented in multiple tautomeric forms. The invention expressly includes all tautomeric forms of the compounds described herein. The compounds may also occur in cis- or trans- or E- or Z-double bond isomeric forms. All such isomeric forms of such compounds are expressly included in the present invention. All crystal forms of the compounds described herein are expressly included in the present invention.

Formulations

Also embraced within this invention is a class of pharmaceutical compositions, also referred to as medicaments, comprising the (active) compounds in association with one or more non-toxic, pharmaceutically-acceptable excipients and/or carriers, diluents and/or adjuvants (collectively referred to herein as "excipient" materials) and, if desired, other active ingredients. The pharmaceutically active compounds of this invention can be processed in accordance with conventional methods of pharmacy to produce medicinal agents for administration to patients, including humans and other mammals.

The compounds of the present invention may be administered to a subject by any suitable route, preferably in the form of a pharmaceutical composition, adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable excipients, including carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, and typically from about 1 to 500 mg. A suitable daily dose for a human or other mammal may vary widely depending on the condition of the patient and other factors, but, once again, can be determined using routine methods and practices.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, and more advantageously about 0.01 and about 30 mg/kg body weight may be appropriate. The daily dose can be administered in one to four doses per day.

For therapeutic purposes, the active compounds of this invention are ordinarily combined with one or more "excipients" appropriate to the indicated route of administration. If administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, pastes, suspensions and the like) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include, for example, Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable excipient, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the excipients, carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (e.g., Captisol), cosolvent solubilization (e.g., propylene glycol) or micellar solubilization (e.g., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of cancer, such as with radiation therapy or with neoplastic or cytotoxic agents.

If formulated as a fixed dose, such combination products employ the compounds of this invention within the accepted dosage ranges. Compounds may also be administered sequentially with known anticancer or cytotoxic agents when a combination formulation is inappropriate. The invention is not limited in the sequence of administration; compounds of the invention may be administered either prior to, simultaneously with or after administration of the known anticancer or cytotoxic agent.

There are large numbers of anti-neoplastic agents available in commercial use, in clinical evaluation and in pre-clinical development, which would be selected for treatment of neoplasia by combination drug chemotherapy. Such anti-neoplastic agents fall into several major categories, namely, antibiotic-type agents, alkylating agents, anti-metabolite agents, hormonal agents, immunological agents, interferon-type agents and a category of miscellaneous agents.

Alternatively, the compounds of the invention may also be used in co-therapies with other anti-neoplastic agents, such as other kinase inhibitors including angiogenic agents such as VEGFR inhibitors, p38 inhibitors and CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors.

Although the invention has been described in connection with specific preferred embodiments, it should be understood that the invention as claimed should not be unduly limited to these specific embodiments. While at least one exemplary embodiment has been presented in the foregoing detailed description of the disclosure, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the disclosure as set forth in the appended claims.

EXAMPLES

The following examples are included to demonstrate various embodiments as contemplated herein. It should be appreciated by those of skill in the art that the techniques disclosed in the examples which follow represent techniques discovered by the inventor(s) to function well in the practice of the invention, and thus can be considered to constitute desirable modes for its practice. However, those of skill in the art should, in light of the present disclosure, appreciate that many changes can be made in the specific embodiments which are disclosed and still obtain a like or similar result without departing from the spirit and scope of the invention. All percentages are in wt. % and all measurements are conducted at 23° C. unless indicated otherwise.

The pyrrolo[2,3-d]pyrimidine heterocycle is a scaffold that may exhibit varied kinase inhibition. In various embodiments, a 4,6-disubstituted pyrrolo[2,3-d]pyrimidines may be a multi-targeted kinase inhibitors of EGFR, platelet derived growth factor receptor kinase b (PDGFRb) and vascular endothelial growth factor receptor kinase (VEGFR). Additionally, a 2,4,7-trisubstituted pyrrolo[2,3-d]pyrimidines may be a dual checkpoint kinase and aurora kinase inhibitors.

Figure 9:
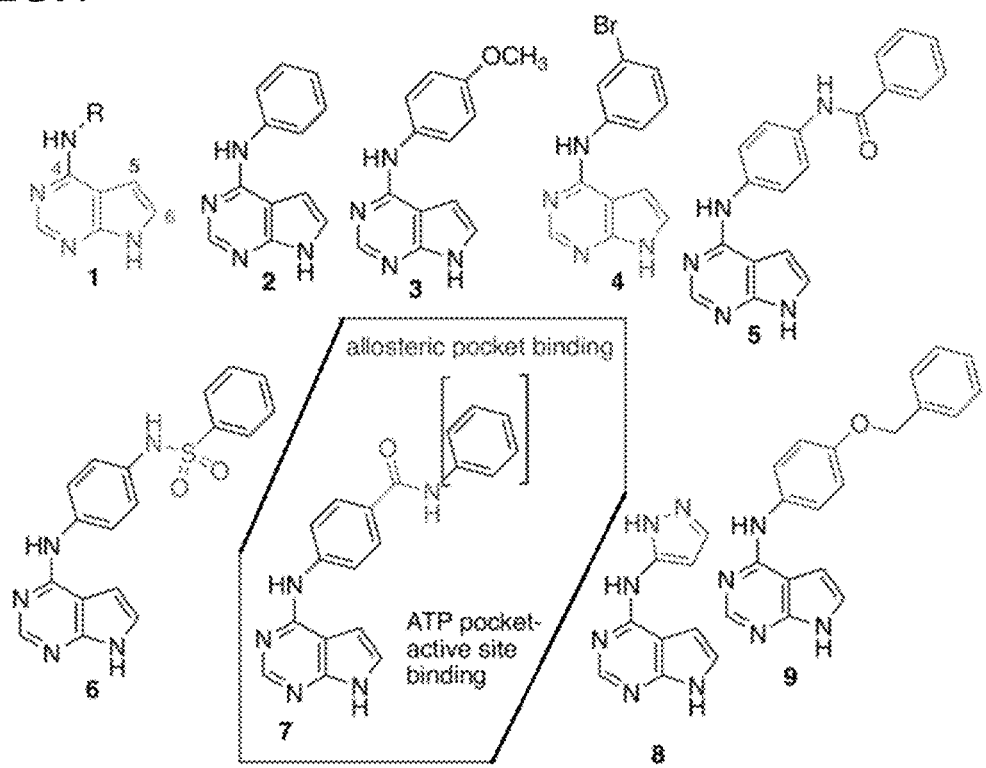
FIG. 9 are representation of chemical structures illustrating a non-limiting embodiment of the compound in a binding pocket.

With reference to FIG. 9, compounds having the general structure 1 may be effective as dual EGFR/AURK inhibitors. Compound 3 may be a micromolar EGFR/AURKA inhibitor, while compound 4 may be a nanomolar EGFR and micromolar AURKA inhibitor. While nanomolar EGFR inhibition was seen for multiple compounds, AURKA inhibition remained in the micromolar range for several compounds of general structure 1.

To improve aurora kinase inhibition, pharmacophoric fragments (shown in blue) may be combined using a molecular hybridization approach from aurora kinase inhibitor, ZM 447439 with structure 1 of the initial series of pyrrolo[2,3-d]pyrimidines to yield compound 5. Compounds 6 and 7 may be synthesized as analogs of compound 5 with varied linkers. Compounds 8 and 9 include side chains seen in AURK inhibitors and Type II EGFR inhibitors respectively. Compounds 2-9 were evaluated in an ADP detection assay externally using the Kinomescan KdELECT platform from Discover X.

With reference to Table 1 below, compound 6 exhibits AURKB inhibition followed by compound 5. Compound 7 exhibits dual EGFR/AURKB inhibition with sub-micromolar EGFR and single-digit micromolar AURKB inhibition. Compound 7 exhibits a preference for AURKB over AURKA. Compounds 5, 6 and 8 were dual AURKB/AURKA inhibitors with no EGFR inhibition. Compound 9 retained potent EGFR inhibition with modest AURKB inhibition.

TABLE 1

Enzymatic inhibition and predicted compound properties

| Compound | EGFR $K_d$ (µM) | L858R EGFR $K_d$ (µM) | AURKA $K_d$ (µM) | AURKB $K_d$ (µM) | MW (g/mol) | clogP |
|---|---|---|---|---|---|---|
| 3 | 3 | 2.8 | 3.5 | 12 | 240.27 | 2.23 |
| 4 | 0.067 | 0.05 | 3.4 | 4.8 | 289.14 | 3.02 |
| 5 | 30 | 30 | 1.6 | 0.47 | 329.26 | 3.44 |

TABLE 1-continued

Enzymatic inhibition and predicted compound properties

| Compound | EGFR $K_d$ (µM) | L858R EGFR $K_d$ (µM) | AURKA $K_d$ (µM) | AURKB $K_d$ (µM) | MW (g/mol) | clogP |
|---|---|---|---|---|---|---|
| 6 | 15 | 0.71 | 2.1 | 0.24 | 365.42 | 2.59 |
| 7 | 0.44 | 0.90 | 16 | 1.5 | 329.26 | 3.44 |
| 8 | 18 | 14 | 1.2 | 1.5 | 200.21 | 0.54 |
| 9 | 0.087 | 0.68 | >30 | 9.8 | 316.36 | 3.6 |
| Staurosporine | 0.12 | | 0.24 | 0.44 | | |

Figure 10:
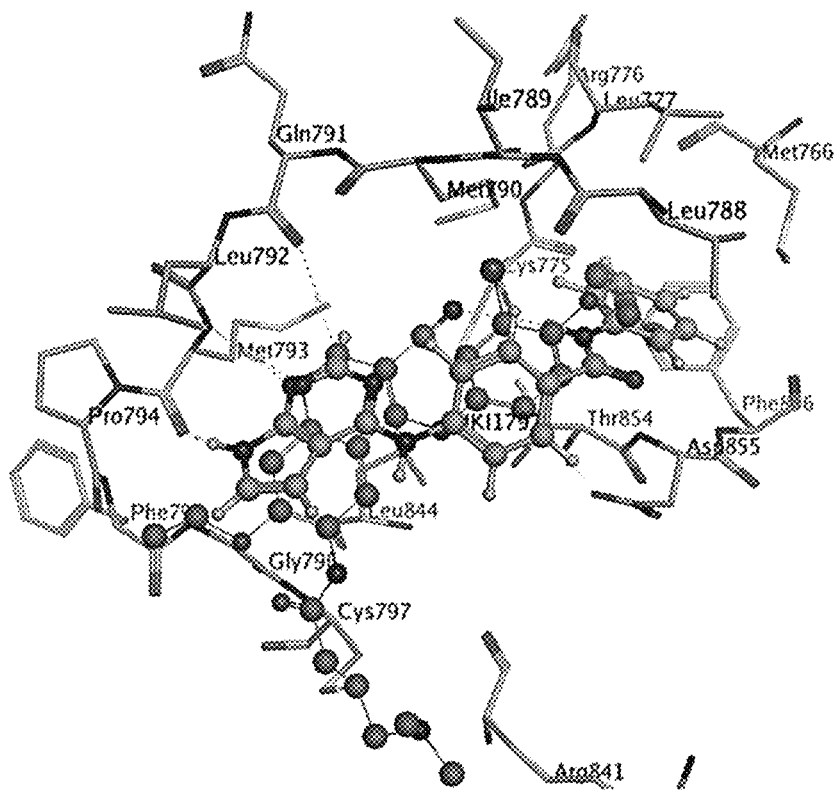
FIG. 10 is another representation of a chemical structure illustrating a non-limiting embodiment of the compound in a binding pocket.
Figure 11:
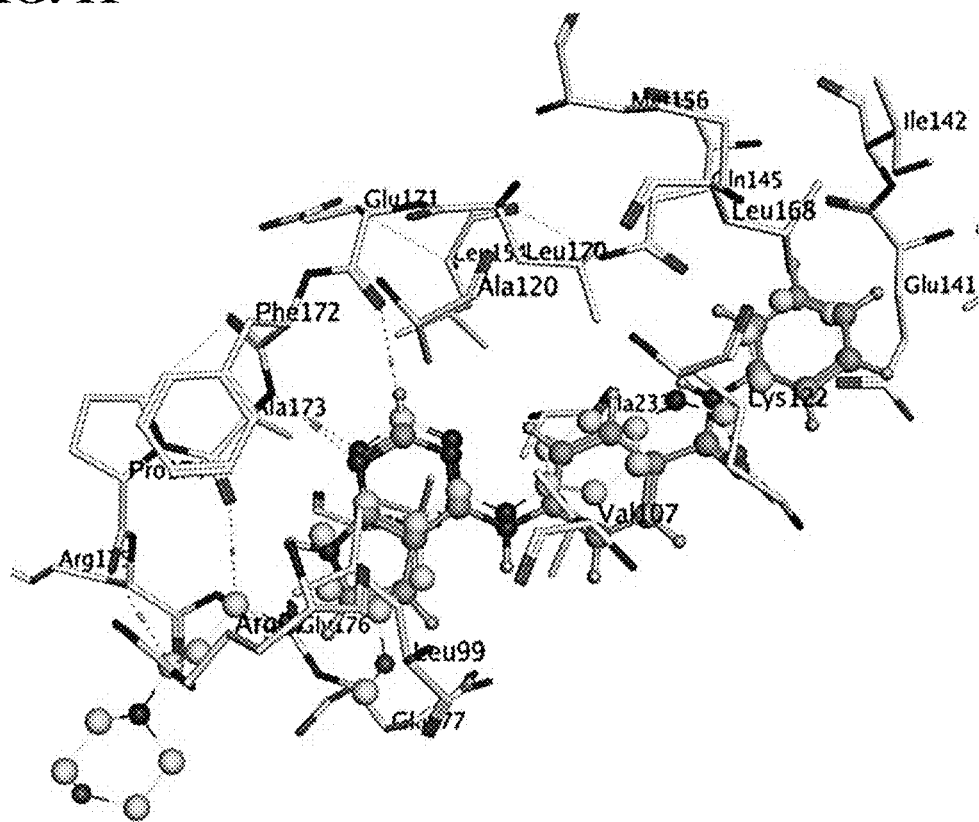
FIG. 11 is another representation of a chemical structure illustrating a non-limiting embodiment of the compound in a binding pocket.

With reference to FIGS. 10 and 11, molecular modeling for compound 7 within EGFR (PDB: 2JIV; Yun, C. H.; Mengwasser, K. E.; Toms, A. V.; Woo, M. S.; Greulich, H.; Wong, K. K.; Meyerson, M.; Eck, M. J. The T790M mutation in EGFR kinase causes drug resistance by increasing the affinity for ATP. *Proc Natl Acad Sci USA* 2008, 105, 2070-2075) and AURKB (PDB: 2VRX; Girdler, F.; Sessa, F.; Patercoli, S.; Villa, F.; Musacchio, A.; Taylor, S. Molecular basis of drug resistance in AURKs. *Chem Biol* 2008, 15, 552-562) showed that it interacted through two hydrogen bonds to the hinge region of both EGFR and AURK. Compound 7 was found to bind deep within the hydrophobic pocket of EGFR and to overlay on a type II EGFR inhibitor, neratinib. Within AURKB, the 4-benzanilido sidechain overlays on the sidechain of ZM 447439 extending into hydrophobic region I and the deep back pocket. The docking protocol used for molecular modeling has been developed in the inventor's lab, and is described in, e.g., Kurup, S.*; McCallister, B.; Liskova, P.; Mistry, T.; Fanizzi, A.; Stanford, D.; Keller, U.; Hoellein•A. Synthesis and biological activity of $N^4$-phenylsubstituted-7H-pyrrolo[2,3-d]pyrimidin-4-amines as dual inhibitors of aurora kinase A and epidermal growth factor receptor kinase. *Journal of Enzyme Inhibition and Medicinal Chemistry* 2018, 1, 74-84. The docking model was validated based on rmsd for the crystallized ligand in its original pose versus the docked pose. The docked poses were examined for fit and interactions within the binding pocket and binding energies were calculated using LigX within Molecular Operating Environment (MOE 2011.10; Molecular Operating Environment (MOE 201.10), Chemical Computing Group, Inc, 1255 University St., Suite 1600, Quebec, Canada, H3B3X3). Rigor was established by performing three iterations and using varied crystal structures. Modeling within AURKA (PDB code: 3E5A; Zhao, B.; Smallwood, A.; Yang, J.; Koretke, K.; Nurse, K.; Calamari, A.; Kirkpatrick, R. B.; Lai, Z. Modulation of kinase-inhibitor interactions by auxiliary protein binding: crystallography studies on Aurora A interactions with VX-680 and with TPX2. *Protein Sci* 2008, 17, 1791-1797) showed that compound 7 was oriented toward solvent within the phosphate binding region of the kinase explaining the poor AURKA inhibition observed. Pharmacokinetic properties and toxicity were calculated for target compounds using the program, DataWarrior (Table 1). Compounds 2-9 were smaller than standards with molecular weights <400, while standards, gefitinib, alisertib and barasertib were much larger in 450-600 range, clog P<5. Lipophilic ligand efficiency (LLE) is drug discovery parameter that correlates potency to lipophilicity of the molecule. The LLE for compound 7 is 0.51 and for gefitinib is 0.46 suggesting that compound 7 is more efficient (a small size and greater contribution to potency). Additionally, no toxicity/mutagenic risks were identified, suggesting that compound 7 provides a good lead for further study.

Figure 12:
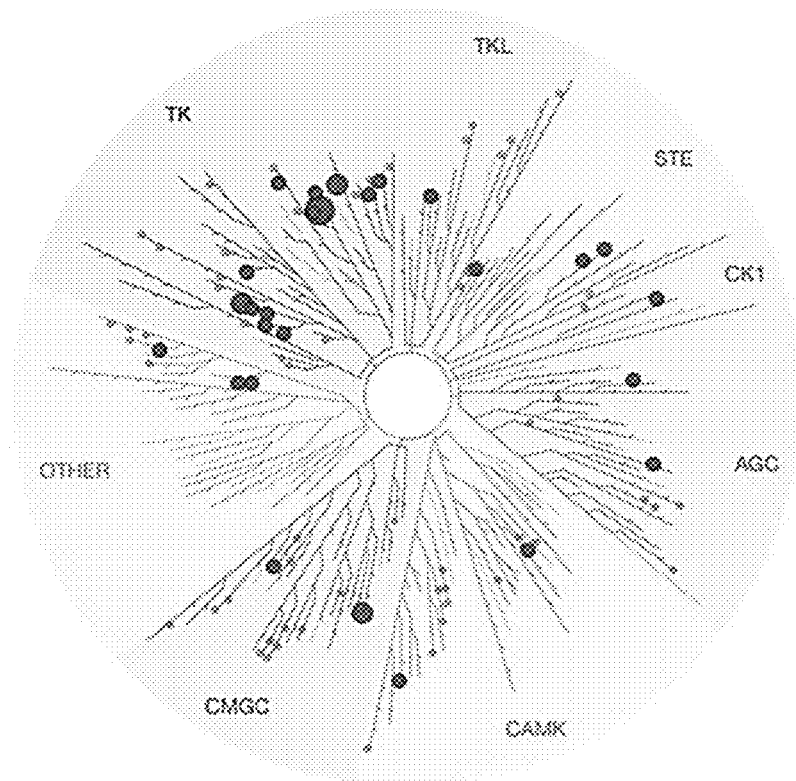
FIG. 12 is a graphical representation illustrating a non-limiting embodiment of an assessment for selectivity of the compound against various kinases.
Figure 13:
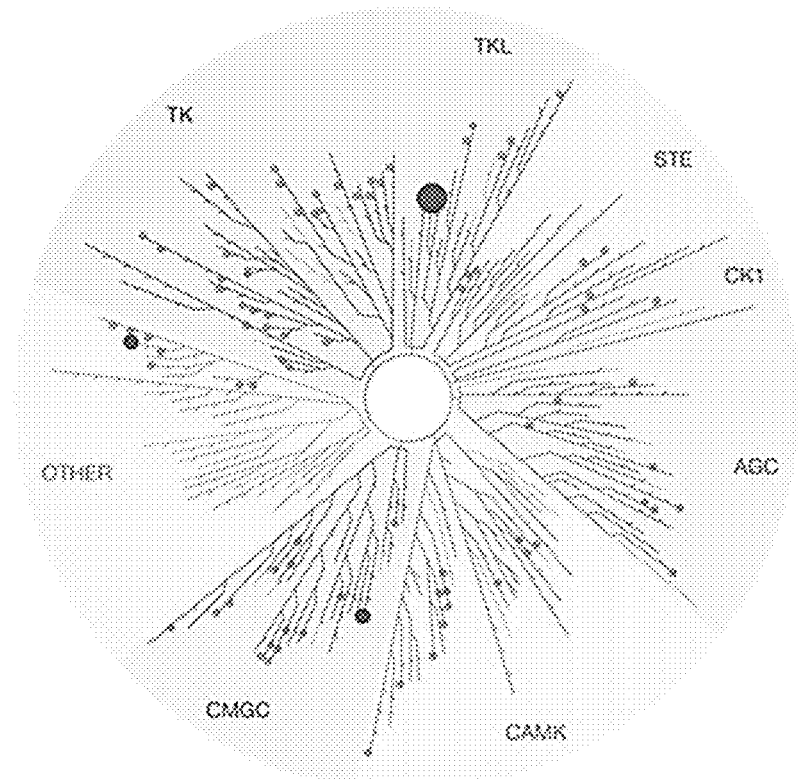
FIG. 13 is another graphical representation illustrating a non-limiting embodiment of an assessment for selectivity of the compound against various kinases.
Figure 14:
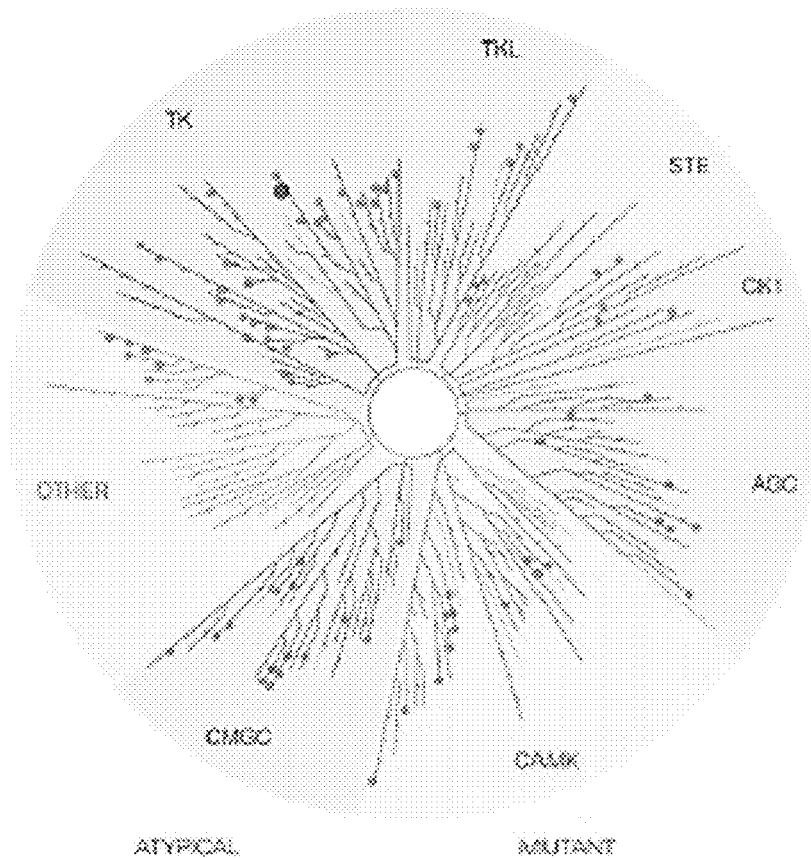
FIG. 14 is another graphical representation illustrating a non-limiting embodiment of an assessment for selectivity of the compound against various kinases.

With reference to FIGS. 12-14, compound 3 (micromolar, dual EGFR/AURKA inhibitor), compound 5 (sub-micromolar, dual AURKA/AURKB inhibitor) and compound 7 (sub-micromolar, dual EGFR/AURKB inhibitor) were evaluated externally for selectivity against 97-different kinases of the scanEDGE platform of DiscoverX. This is a reliable platform that has been used to assess selectivity for most approved kinase inhibitors. Selectivity scores were calculated that allow a comparison of different compound selectivity. The selectivity score, S(35) was calculated by dividing the kinases inhibited by >35% with the total number of kinases tested in the panel. Smaller scores indicate higher selectivity. Compound 7 was highly selective compared to compound 3 further validating it as a lead molecule for dual EGFR/AURKB inhibition.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, different, special, and/or unexpected results may be obtained from each member of the respective Markush group independent from all other Markush members. Each member of a Markush group may be relied upon individually and or in combination and provides adequate support for specific embodiments within the scope of the appended claims.

Further, any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The present invention has been described herein in an illustrative manner, and it is to be understood that the terminology which has been used is intended to be in the nature of words of description rather than of limitation. Many modifications and variations of the present invention are possible in light of the above teachings. The present invention may be practiced otherwise than as specifically described within the scope of the appended claims. The subject matter of all combinations of independent and dependent claims, both single and multiple dependent, is herein expressly contemplated.

What is claimed is:

1. A compound of Formula (I):

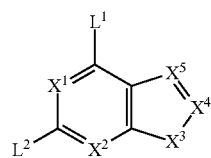
(I)

or a pharmaceutically acceptable salt thereof, wherein:
$X^1$ is N;
$X^2$ is N;
$X^3$ is —NH—;
$X^4$ is $CR^2$ or N;
$R^2$ is a 5-membered heteroaryl;
  wherein the 5-membered heteroaryl contains 1 N heteroatom and 1 additional heteroatom selected from the group consisting of N, O, and S; and
  wherein the 5-membered heteroaryl is optionally substituted with 1, 2, or 3 substituents independently selected from the group consisting of halo, CN, $NO_2$, $C_{1-6}$ alkyl, $C_{1-6}$ haloalkyl, $CH_2$-phenyl, $NH_2$, $NHC_{1-10}$ alkyl, $N(C_{1-10}$ alkyl$)_2$, OH, $OC_{1-6}$ alkyl, $OC_{1-6}$ haloalkyl, $C_{3-6}$ cycloalkyl, and phenyl;
$X^5$ is CH or $C(CH_3)$;
L is —$NR^4$—$R^1$;
$R^1$ is

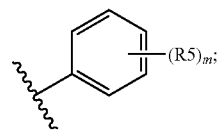

$R^4$ is H;
$L^2$ is H or $NH_2$;
(i) each R5 is independently $CH_2$-phenyl, $C_{3-6}$ cycloalkyl, or phenyl; or
(ii) each R5 is independently:

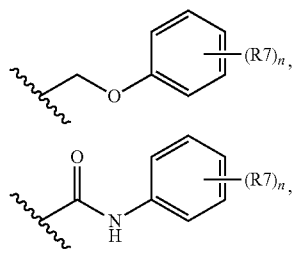

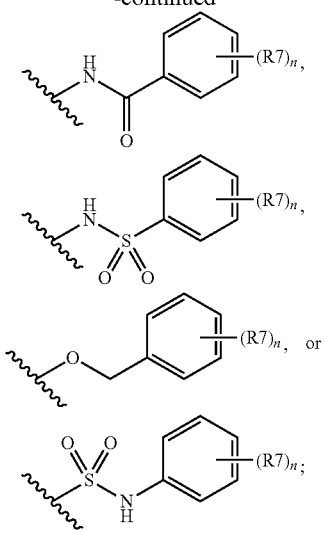

each R7 is independently H, halo, CN, $NO_2$, $C_{1-10}$ alkyl, $C_{1-10}$ haloalkyl, $C_{2-10}$ alkenyl, $C_{2-10}$ alkynyl, $C(O)C_{1-6}$ alkyl, $C(O)NHC_{1-6}$ alkyl, $NH_2$, $NHC_{1-10}$ alkyl, $N(C_{1-10}$ alkyl$)_2$, $NHC(O)C_{1-6}$ alkyl, $NHS(O)_2$ $C_{1-10}$ alkyl, OH, $OC_{1-10}$ alkyl, $OC_{1-10}$ haloalkyl, SH, $SC_{1-10}$ alkyl, $S(O)C_{1-6}$ alkyl, $S(O)_2NHC_{1-6}$ alkyl, $C_{3-10}$ cycloalkyl, $C_{4-10}$ cycloalkenyl, a monocyclic 3- to 8-membered ring, or a bicyclic 6- to 12-membered ring;
  wherein each monocyclic 3- to 8-membered ring or bicyclic 6- to 12-membered ring is fully saturated, partially unsaturated, or fully unsaturated;
  wherein each monocyclic 3- to 8-membered ring independently contains carbon atoms and optionally and independently contains 1, 2, or 3 heteroatoms independently selected from the group consisting of N, O, and S;
  wherein each bicyclic 6- to 12-membered ring independently contains carbon atoms and optionally and independently contains 1, 2, 3, 4, 5, or 6 heteroatoms independently selected from the group consisting of N, O, and S;
  wherein each $C_{1-10}$ alkyl, $C_{2-10}$ alkenyl, $C_{2-10}$ alkynyl, $NHC_{1-10}$ alkyl, $N(C_{1-10}$ alkyl$)_2$, $OC_{1-10}$ alkyl, and $SC_{1-10}$ alkyl is optionally and independently substituted with 1, 2, 3, 4, or 5 substituents independently selected from the group consisting of halo, CN, $NO_2$, $CH_2$-phenyl, $NH_2$, $NHC_{1-10}$ alkyl, $N(C_{1-10}$ alkyl$)_2$, OH, $OC_{1-6}$ alkyl, $OC_{1-10}$ haloalkyl, =O, $C_{3-6}$ cycloalkyl, phenyl, and a multicyclic ring system;
  wherein each $C_{3-10}$ cycloalkyl, $C_{4-10}$ cycloalkenyl, monocyclic 3- to 8-membered ring, or bicyclic 6- to 12-membered ring is optionally and independently substituted with 1, 2, 3, 4, or 5 substituents independently selected from the group consisting of halo, CN, $NO_2$, $C_{1-6}$ alkyl, $C_{1-10}$ haloalkyl, $CH_2$-phenyl, $NH_2$, $NHC_{1-10}$ alkyl, $N(C_{1-10}$ alkyl$)_2$, OH, $OC_{1-6}$ alkyl, $OC_{1-10}$ haloalkyl, =O, $C_{3-6}$ cycloalkyl, phenyl, and a multicyclic ring system; and
  wherein each multicyclic ring system contains at least one nonaromatic ring and at least one aromatic ring; or wherein each multicyclic ring system contains at least one heteroaromatic ring;
m is 1, 2, 3, 4, or 5; and
each n is independently 1, 2, 3, 4, or 5.

2. The compound of claim 1, or a pharmaceutically acceptable salt thereof, wherein $X^4$ is $CR^2$.

3. The compound of claim 1, or a pharmaceutically acceptable salt thereof, wherein $X^4$ is N.

4. The compound of claim 1, or a pharmaceutically acceptable salt thereof, wherein $L^2$ is H.

5. The compound of claim 1, or a pharmaceutically acceptable salt thereof, wherein $L^2$ is $NH_2$.

6. The compound of claim 1, wherein the compound is:

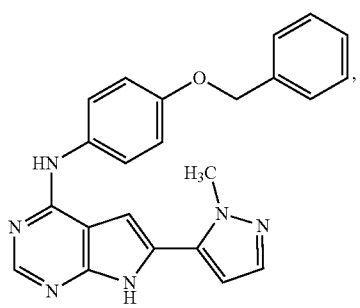 [SMILES: Cn1nccc1-c1cc2c(Nc3ccc(OCc4ccccc4)cc3)ncnc2[nH]1]

or a pharmaceutically acceptable salt thereof.

7. The compound of claim 1, wherein the compound is:

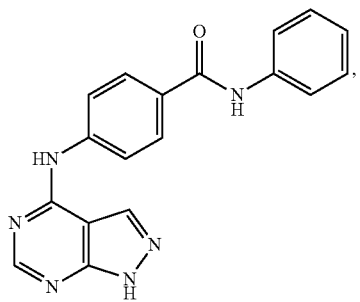 [SMILES: O=C(Nc1ccccc1)c1ccc(Nc2ncnc3[nH]ncc23)cc1]

or a pharmaceutically acceptable salt thereof.

8. A compound, wherein the compound is:

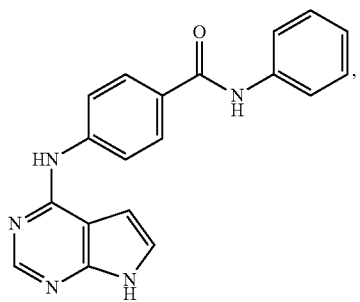 [SMILES: O=C(Nc1ccccc1)c1ccc(Nc2ncnc3[nH]ccc23)cc1]

or a pharmaceutically acceptable salt thereof.

9. A method for inhibiting aurora kinase A, aurora kinase B, and/or epidermal growth factor activity in a subject, wherein the method comprises administering to the subject in need thereof a therapeutically effective amount of a compound of Formula (I):

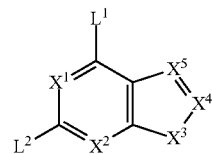

(I)

or a pharmaceutically acceptable salt thereof,
wherein:
$X^1$ is N;
$X^2$ is N;
$X^3$ is —NH—;
$X^4$ is $CR^2$ or N;
$R^2$ is a 5-membered heteroaryl;
  wherein the 5-membered heteroaryl contains 1 N heteroatom and 1 additional heteroatom selected from the group consisting of N, O, and S; and
  wherein the 5-membered heteroaryl is optionally substituted with 1, 2, or 3 substituents independently selected from the group consisting of halo, CN, $NO_2$, $C_{1-4}$ alkyl, $C_{1-4}$ haloalkyl, $CH_2$-phenyl, $NH_2$, $NHC_{1-10}$ alkyl, $N(C_{1-10}$ alkyl$)_2$, OH, $OC_{1-6}$ alkyl, $OC_{1-6}$ haloalkyl, $C_{3-6}$ cycloalkyl, and phenyl;
$X^5$ is CH or $C(CH_3)$;
$L^1$ is $—NR^4—R^1$;
$R^1$ is

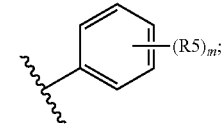

$R^4$ is H;
$L^2$ is H or $NH_2$;
(i) each R5 is independently $CH_2$-phenyl, $C_{3-6}$ cycloalkyl, or phenyl; or
(ii) each R5 is independently:

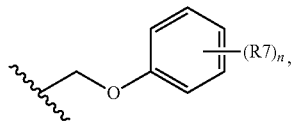

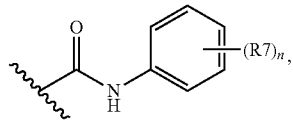

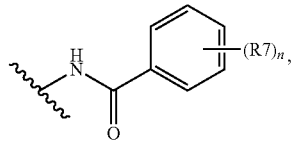

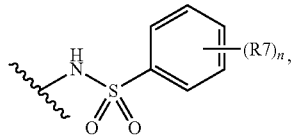

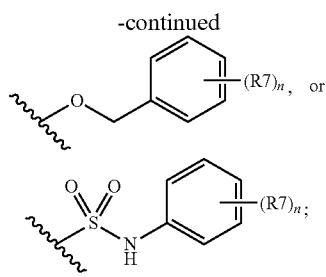

each R7 is independently H, halo, CN, $NO_2$, $C_{1-10}$ alkyl, $C_{1-10}$ haloalkyl, $C_{2-10}$ alkenyl, $C_{2-10}$ alkynyl, $C(O)C_{1-6}$ alkyl, $C(O)NHC_{1-6}$ alkyl, $NH_2$, $NHC_{1-10}$ alkyl, $N(C_{1-10}$ alkyl$)_2$, $NHC(O)C_{1-6}$ alkyl, $NHS(O)_2$ $C_{1-10}$ alkyl, OH, $OC_{1-10}$ alkyl, $OC_{1-10}$ haloalkyl, SH, $SC_{1-10}$ alkyl, $S(O)C_{1-6}$ alkyl, $S(O)_2NHC_{1-6}$ alkyl, $C_{3-10}$ cycloalkyl, $C_{4-10}$ cycloalkenyl, a monocyclic 3- to 8-membered ring, or a bicyclic 6- to 12-membered ring;

wherein each monocyclic 3- to 8-membered ring or bicyclic 6- to 12-membered ring is fully saturated, partially unsaturated, or fully unsaturated;

wherein each monocyclic 3- to 8-membered ring independently contains carbon atoms and optionally and independently contains 1, 2, or 3 heteroatoms independently selected from the group consisting of N, O, and S;

wherein each bicyclic 6- to 12-membered ring independently contains carbon atoms and optionally and independently contains 1, 2, 3, 4, 5, or 6 heteroatoms independently selected from the group consisting of N, O, and S;

wherein each $C_{1-10}$ alkyl, $C_{2-10}$ alkenyl, $C_{2-10}$ alkynyl, $NHC_{1-10}$ alkyl, $N(C_{1-10}$ alkyl$)_2$, $OC_{1-10}$ alkyl, and $SC_{1-10}$ alkyl is optionally and independently substituted with 1, 2, 3, 4, or 5 substituents independently selected from the group consisting of halo, CN, $NO_2$, $CH_2$-phenyl, $NH_2$, $NHC_{1-10}$ alkyl, $N(C_{1-10}$ alkyl$)_2$, OH, $OC_{1-6}$ alkyl, $OC_{1-10}$ haloalkyl, $=O$, $C_{3-6}$ cycloalkyl, phenyl, and a multicyclic ring system;

wherein each $C_{3-10}$ cycloalkyl, $C_{4-10}$ cycloalkenyl, monocyclic 3- to 8-membered ring, or bicyclic 6- to 12-membered ring is optionally and independently substituted with 1, 2, 3, 4, or 5 substituents independently selected from the group consisting of halo, CN, $NO_2$, $C_{1-6}$ alkyl, $C_{1-10}$ haloalkyl, $CH_2$-phenyl, $NH_2$, $NHC_{1-10}$ alkyl, $N(C_{1-10}$ alkyl$)_2$, OH, $OC_{1-6}$ alkyl, $OC_{1-10}$ haloalkyl, $=O$, $C_{3-6}$ cycloalkyl, phenyl, and a multicyclic ring system; and wherein each multicyclic ring system contains at least one nonaromatic ring and at least one aromatic ring; or wherein each multicyclic ring system contains at least one heteroaromatic ring:

m is 1, 2, 3, 4, or 5; and each n is independently 1, 2, 3, 4, or 5.

10. The method of claim 9, wherein the subject has cancer.

11. The method of claim 9, wherein the subject is a mammal.

12. The method of claim 9, wherein $X^4$ is $CR^2$.

13. The method of claim 9, wherein $X^4$ is N.

14. The method of claim 8, wherein $L^2$ is H.

15. The method of claim 9, wherein $L^2$ is $NH_2$.

* * * * *

UNITED STATES PATENT AND TRADEMARK OFFICE
CERTIFICATE OF CORRECTION

| | | |
|---|---|---|
| PATENT NO. | : 11,814,388 B1 | Page 1 of 1 |
| APPLICATION NO. | : 17/459558 | |
| DATED | : November 14, 2023 | |
| INVENTOR(S) | : Sonali Raghavan Kunjunni Karup | |

It is certified that error appears in the above-identified patent and that said Letters Patent is hereby corrected as shown below:

In the Specification

On Column 1, Line 15, before the "TECHNICAL FIELD", please insert the following paragraph:
-- STATEMENT REGARDING FEDERALLY SPONSORED RESEARCH OR DEVELOPMENT
This invention was made by government support under grant number 1R15CA246256-01A1 awarded by the National Institutes of Health. The government has certain rights in the invention. --

Signed and Sealed this
Twenty-fifth Day of June, 2024

Katherine Kelly Vidal
*Director of the United States Patent and Trademark Office*